US012650430B2

(12) United States Patent
Mittal et al.

(10) Patent No.: US 12,650,430 B2
(45) Date of Patent: Jun. 9, 2026

(54) QUANTITATIVE CENTROSOMAL AMPLIFICATION SCORE TO PREDICT LOCAL RECURRENCE OF DUCTAL CARCINOMA IN SITU

(71) Applicant: Georgia State University Research Foundation, Inc., Atlanta, GA (US)

(72) Inventors: Karuna Mittal, Atlanta, GA (US); Padmashree Rida, Atlanta, GA (US); Ritu Aneja, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 1372 days.

(21) Appl. No.: 17/311,067

(22) PCT Filed: Dec. 6, 2019

(86) PCT No.: PCT/US2019/065057
§ 371 (c)(1),
(2) Date: Jun. 4, 2021

(87) PCT Pub. No.: WO2020/118245
PCT Pub. Date: Jun. 11, 2020

(65) Prior Publication Data
US 2022/0042999 A1     Feb. 10, 2022

Related U.S. Application Data

(60) Provisional application No. 62/776,144, filed on Dec. 6, 2018.

(51) Int. Cl.
| | |
|---|---|
| *G01N 33/575* | (2026.01) |
| *G01N 33/50* | (2006.01) |
| *G01N 33/57515* | (2026.01) |
| *G01N 33/68* | (2006.01) |
| *G16H 30/40* | (2018.01) |
| *G16H 50/30* | (2018.01) |

(52) U.S. Cl.
CPC ... *G01N 33/57595* (2026.01); *G01N 33/5026* (2013.01); *G01N 33/5091* (2013.01); *G01N 33/57515* (2026.01); *G01N 33/6875* (2013.01); *G16H 30/40* (2018.01); *G16H 50/30* (2018.01)

(58) Field of Classification Search
CPC ......... G01N 33/57496; G01N 33/5026; G01N 33/5091; G01N 33/57415; G01N 33/6875; G01N 33/5005; G01N 2800/54; G01N 33/574; G16H 30/40; G16H 50/30
See application file for complete search history.

(56) References Cited

U.S. PATENT DOCUMENTS 9,589,100 B2 *   3/2017  Aneja .................. A61K 31/343
2017/0067118 A1   3/2017  Dartmann et al.

FOREIGN PATENT DOCUMENTS

WO      WO2013077859      5/2013

OTHER PUBLICATIONS

Pujana et al. (2007): Network modeling links breast cancer susceptibility and centrosome dysfunction. Nature genetics 39.11: 1338-134.*
Patel N et al. (Mar. 2018): Integrated genomics and functional validation identifies malignant cell specific dependencies in triple negative breast cancer. Nature communications 9:11044, 16 pages.*
International Search Report and Written Opinion of the International Searching Authority in International Application No. PCT/US2019/065057 dated Mar. 3, 2020; 6 pages.
Ogden, et al., "Prognostic value of CA20, a score based on centrosome amplification-associated genes, in breast tumors," Sci Rep, Mar. 21, 2017, vol. 7, No. 262, pp. 1-11.
Pannu, et al., "Rampant centrosome amplification underlies more aggressive disease course of triple negative breast cancers," Oncotarget, Apr. 30, 2015, vol. 6, pp. 10487-10497.
Mittal, et al., "Abstract P5-18-02: A quantitative centrosomal amplification score (CAS) predicts local recurrence in ductal carcinoma in situ," Cancer Research, Feb. 15, 2019, vol. 79, Iss. 4, Suppl. pp. 1 of 1; entire document.
Mittal, et al., "A quantitative centrosomal amplification score predicts local recurrence in ductal carcinoma in situ," Clinical Cancer Research, Jan. 14, 2020, pp. 1-22; entire document.

* cited by examiner

*Primary Examiner* — Mary K Zeman
*Assistant Examiner* — Vy Rossi
(74) *Attorney, Agent, or Firm* — Smith Gambrell & Russell LLP

(57)          ABSTRACT

Embodiments may provide capability to predict the 10-year risk of local recurrence of ductal carcinoma in situ (DCIS) conditions or other non-invasive carcinomas in situ. Embodiments may evaluate the severity and frequency of numerical and structural CA present within DCIS, and may assign a quantitative centrosomal amplification score (CAS) to each sample. For example, a method of determining the risk profile of a carcinoma in situ in a patient may comprise determining severity and frequency of numerical and structural centrosome amplification present within a sample of a carcinoma in situ from the patient and determining at least one centrosome amplification score (CAS) value for the sample based on the determined severity and frequency of numerical and structural centrosome amplification in the sample, wherein the determined at least one CAS value provides a measure of a level of a 10-year risk of local recurrence associated with the carcinoma in situ.

20 Claims, 51 Drawing Sheets

DCIS/IBC Tissue

Normal Tissue

ALGORITHM-BASED ANALYTICS

CASi + CASm = CAStotal

$$CASi = Average\left(\frac{N_i - R_{th}}{R}\right) * \frac{percentage(N_i > R_{th})}{scaling\ factor\ \beta_i}$$

$$= \left(\frac{\sum_{i=1,N_i>2}^{N}(N_i - 2)}{\sum_{i=1}^{N} I(N_i > 2)} * \frac{1}{R}\right) * \frac{p_i}{\beta_i}$$

$$CASm = Average\left(\frac{V_{im} - V_{th}}{\sigma_{V_{im}}}\right) * \frac{percentage(V_{im} > V_{th})}{scaling\ factor\ \beta_m}$$

$$= \frac{\sum_{i=1}^{N}\sum_{m=1}^{N_i}(V_{im} - 0.735) * I((V_{im} > 0.735)}{\sigma_{V_{im}}} * \frac{p_m}{\beta_m}$$

Fig. 3a

| Discovery Cohort Overall Clinical Characteristics | | | |
|---|---|---|---|
| Baseline Characteristics | Recurrence-Free | Local Recurrence | p-value |
| Patient Age, n(%) | | | |
| Age>50 | 87 (82.86) | 22 (78.57) | 0.6003 |
| Age<=50 | 18 (17.14) | 6 (21.43) | |
| Tumor Size, n(%) | | | |
| Size>16 | 51 (48.57) | 15 (53.57) | 0.6382 |
| Size<=16 | 54 (51.43) | 13 (46.43) | |
| Grade, n(%) | | | |
| High | 97 (92.38) | 21 (75.00) | 0.0098 |
| Mid and Low | 8 (7.62) | 7 (25.00) | |
| Comedo Necrosis, n(%) | | | |
| No | 14 (13.33) | 8 (28.57) | 0.0538 |
| Yes | 91 (86.67) | 20 (71.43) | |
| Radiotherapy, n(%) | | | |
| No | 57 (54.29) | 21 (75.00) | 0.0480 |
| Yes | 48 (45.71) | 7 (25.00) | |
| Receptor Status, n(%) | | | |
| ER/PR/HER2-Positive | 3 (2.86) | 2 (7.14) | 0.6826 |
| ER/PR-Positive and HER2-Negative | 20 (19.05) | 7 (25.00) | |
| HER2-Positive | 8 (7.62) | 2 (7.14) | |
| TNBC | 9 (8.57) | 1 (3.57) | |
| Missing | 65 (61.90) | 16 (57.14) | |

Fig. 3b

| Validation Cohort Overall Clinical Characteristics | | | |
|---|---|---|---|
| Baseline Characteristics | Recurrence-Free | Local Recurrence | p-value |
| Patient Age, n(%) | | | |
| Age>50 | 68 (71.58) | 12 (50.00) | 0.0442 |
| Age<=50 | 27 (28.42) | 12 (50.00) | |
| Tumor Size, n(%) | | | |
| Size>16 | 81 (85.26) | 9 (37.50) | <0.0001 |
| Size<=16 | 14 (14.74) | 15 (62.50) | |
| Grade, n(%) | | | |
| High | 47 (49.47) | 12 (50.00) | 0.9632 |
| Mid and Low | 48 (50.53) | 12 (50.00) | |
| Comedo Necrosis, n(%) | | | |
| No | 37 (38.95) | 16 (66.67) | 0.0146 |
| Yes | 58 (61.05) | 8 (33.33) | |
| Radiotherapy, n(%) | | | |
| No | 83 (87.37) | 22 (91.67) | 0.5593 |
| Yes | 12 (12.63) | 2 (8.33) | |
| Receptor Status, n(%) | | | |
| ER/PR/HER2-Positive | 9 (9.78) | 4 (14.81) | 0.4706 |
| ER/PR-Positive and HER2-Negative | 37 (40.22) | 15 (55.56) | |
| HER2-Positive | 13 (14.13) | 2 (7.41) | |
| TNBC | 6 (6.52) | 1 (3.70) | |
| Missing | 27 (29.35) | 5 (18.52) | |

Fig. 4a

| Discovery Cohort Cox Regression | | Univariate Analysis | | | | Multivariate Analysis | | | |
|---|---|---|---|---|---|---|---|---|---|
| Variables | | p-value | Hazard Ratio | 95% Hazard Ratio Confidence Limits | | p-value | Hazard Ratio | 95% Hazard Ratio Confidence Limits | |
| Recurrence-Free Survival | | | | | | | | | |
| CAStotal | High vs Low | <0.001 | 6.337 | 2.196 | 18.287 | <0.001 | 7.869 | 2.709 | 22.857 |
| Age | >50 years vs <=50 years | 0.437 | 0.697 | 0.280 | 1.733 | 0.599 | 0.767 | 0.284 | 2.068 |
| Grade | High vs intermediate/ low | 0.009 | 0.317 | 0.134 | 0.752 | 0.022 | 0.257 | 0.081 | 0.823 |
| Comedo Necrosis | Present vs absent | 0.088 | 2.043 | 0.899 | 4.640 | 0.271 | 1.635 | 0.681 | 3.926 |
| Radiotherapy | No vs yes | 0.128 | 1.946 | 0.826 | 4.583 | 0.403 | 1.470 | 0.596 | 3.628 |
| Receptor status | ER/PR positive HER2 negative | 0.194 | 1.719 | 0.759 | 3.893 | 0.163 | 2.044 | 0.748 | 5.581 |
| | ER/PR/HER2 negative | 0.663 | 0.638 | 0.084 | 4.821 | 0.977 | 0.969 | 0.120 | 7.835 |
| | ER/PR/HER2 positive | 0.240 | 2.425 | 0.553 | 10.640 | 0.323 | 2.329 | 0.435 | 12.456 |
| | HER2 positive | 0.534 | 1.480 | 0.430 | 5.089 | 0.214 | 2.458 | 0.595 | 10.151 |

Fig. 4b

| Validation Cohort Cox Regression | | Univariate Analysis | | | Multivariate Analysis | | |
|---|---|---|---|---|---|---|---|
| Variables | | p-value | Hazard Ratio | 95% Hazard Ratio Confidence Limits | p-value | Hazard Ratio | 95% Hazard Ratio Confidence Limits |
| Recurrence-Free Survival | | | | | | | |
| CAStotal | High vs Low | <0.001 | 4.820 | 2.041 | 11.384 | <0.001 | 5.569 | 2.310 | 13.427 |
| Age | >50 years vs <=50 years | 0.154 | 0.535 | 0.227 | 1.263 | 0.011 | 0.328 | 0.138 | 0.776 |
| Grade | High vs intermediate/ low | 0.954 | 0.976 | 0.430 | 2.216 | 0.461 | 1.404 | 0.569 | 3.464 |
| Comedo Necrosis | Present vs absent | 0.026 | 2.652 | 1.123 | 6.259 | 0.008 | 5.817 | 1.590 | 21.283 |
| Radiotherapy | No vs yes | 0.853 | 1.148 | 0.268 | 4.916 | 0.923 | 0.925 | 0.191 | 4.483 |
| Receptor status | ER/PR positive HER2 negative | 0.312 | 1.686 | 0.612 | 4.646 | 0.330 | 0.518 | 0.138 | 1.947 |
| | ER/PR/HER2 negative | 0.881 | 0.848 | 0.099 | 7.275 | 0.347 | 3.018 | 0.302 | 30.159 |
| | ER/PR/HER2 positive | 0.286 | 2.047 | 0.549 | 7.641 | 0.913 | 0.921 | 0.212 | 4.006 |
| | HER2 positive | 0.667 | 0.697 | 0.135 | 3.608 | 0.664 | 1.464 | 0.262 | 8.171 |

Survival Probability

Recurrence-Free Survival (Months)

CAStotal —— High —— Low

| Mean Values | Discovery Cohort | | |
| | Local Recurrence | Recurrence-Free | p-value |
| --- | --- | --- | --- |
| CASi | 1.30 | 0.73 | <0.01 |
| CASm | 1.09 | 0.81 | 0.04 |
| CAStotal | 2.41 | 1.54 | <0.01 |

Fig. 21

| Groups | p-value | Hazard Ratio |
|---|---|---|
| CASi severity | 0.120 | 2.77 |
| CASi frequency | <0.001 | 4.77 |
| CASm severity | 0.006 | 5.40 |
| CASm frequency | 0.072 | 2.44 |

Fig. 24

Discovery Cohort Cox Regression

| Variables | p-value | Hazard Ratio | 95% Hazard Ratio Confidence Limits | |
|---|---|---|---|---|
| CASi | High | <0.001 | 5.811 | 2.465 | 13.699 |

Discovery Cohort Cox Regression

| Variables | p-value | Hazard Ratio | 95% Hazard Ratio Confidence Limits | |
|---|---|---|---|---|
| CASm | High | 0.051 | 2.207 | 0.997 | 4.885 |

Validation Cohort Cox Regression

| Variables | p-value | Hazard Ratio | 95% Hazard Ratio Confidence Limits | |
|---|---|---|---|---|
| CASi | High | <0.001 | 6.222 | 2.469 | 15.685 |

Validation Cohort Cox Regression

| Variables | p-value | Hazard Ratio | 95% Hazard Ratio Confidence Limits | |
|---|---|---|---|---|
| CASm | High | 0.001 | 4.024 | 1.719 | 9.420 |

Fig. 25

Ai — Discovery Cohort CASi Cox Regression

| Variables | | p-value | Multivariate Analysis Hazard Ratio | 95% Hazard Ratio Confidence Limits | |
|---|---|---|---|---|---|
| Recurrence-Free Survival | | | | | |
| CASi | High vs Low | <0.001 | 4.968 | 2.052 | 12.029 |
| Age | >50 years vs <=50 years | 0.771 | 1.188 | 0.430 | 3.116 |
| Grade | High vs intermediate/low | 0.088 | 0.358 | 0.110 | 1.163 |
| Comedo Necrosis | Present vs absent | 0.661 | 1.237 | 0.479 | 3.194 |
| Radiotherapy | No vs yes | 0.512 | 1.379 | 0.527 | 3.608 |
| Receptor status | ER/PR positive HER2 negative | 0.345 | 1.654 | 0.582 | 4.702 |
| | ER/PR negative | 0.823 | 1.271 | 0.155 | 10.415 |
| | ER/PR/HER2 positive | 0.399 | 2.031 | 0.391 | 10.547 |
| | HER2 positive | 0.206 | 2.465 | 0.609 | 9.975 |

Aii — Discovery Cohort CASm Cox Regression

| Variables | | p-value | Multivariate Analysis Hazard Ratio | 95% Hazard Ratio Confidence Limits | |
|---|---|---|---|---|---|
| Recurrence-Free Survival | | | | | |
| CASm | High vs Low | 0.005 | 3.559 | 1.457 | 8.695 |
| Age | >50 years vs <=50 years | 0.466 | 0.676 | 0.236 | 1.937 |
| Grade | High vs intermediate/low | 0.013 | 0.226 | 0.070 | 0.732 |
| Comedo Necrosis | Present vs absent | 0.792 | 1.135 | 0.442 | 2.919 |
| Radiotherapy | No vs yes | 0.114 | 2.240 | 0.823 | 6.100 |
| Receptor status | ER/PR positive HER2 negative | 0.152 | 2.151 | 0.755 | 6.127 |
| | ER/PR negative | 0.828 | 0.791 | 0.096 | 6.522 |
| | ER/PR/HER2 positive | 0.435 | 1.973 | 0.358 | 10.868 |
| | HER2 positive | 0.210 | 2.476 | 0.599 | 10.233 |

Bi — Validation Cohort CASi Cox Regression

| Variables | | p-value | Multivariate Analysis Hazard Ratio | 95% Hazard Ratio Confidence Limits | |
|---|---|---|---|---|---|
| Recurrence-Free Survival | | | | | |
| CASi | High vs Low | <0.001 | 6.812 | 2.385 | 19.453 |
| Age | >50 years vs <=50 years | 0.051 | 0.408 | 0.166 | 1.003 |
| Grade | High vs intermediate/low | 0.476 | 1.443 | 0.526 | 3.692 |
| Comedo Necrosis | Present vs absent | 0.011 | 6.469 | 1.536 | 27.237 |
| Radiotherapy | No vs yes | 0.628 | 0.677 | 0.140 | 3.279 |
| Receptor status | ER/PR positive HER2 negative | 0.199 | 0.407 | 0.103 | 1.608 |
| | ER/PR negative | 0.179 | 5.195 | 0.470 | 57.412 |
| | ER/PR/HER2 positive | 0.279 | 0.383 | 0.067 | 2.177 |
| | HER2 positive | 0.485 | 1.849 | 0.328 | 10.430 |

Bii — Validation Cohort CASm Cox Regression

| Variables | | p-value | Multivariate Analysis Hazard Ratio | 95% Hazard Ratio Confidence Limits | |
|---|---|---|---|---|---|
| Recurrence-Free Survival | | | | | |
| CASm | High vs Low | 0.002 | 4.297 | 1.731 | 10.670 |
| Age | >50 years vs <=50 years | 0.021 | 0.344 | 0.139 | 0.848 |
| Grade | High vs intermediate/low | 0.495 | 1.420 | 0.518 | 3.894 |
| Comedo Necrosis | Present vs absent | 0.006 | 6.074 | 1.666 | 22.114 |
| Radiotherapy | No vs yes | 0.649 | 0.702 | 0.152 | 3.233 |
| Receptor status | ER/PR positive HER2 negative | 0.302 | 0.532 | 0.161 | 1.763 |
| | ER/PR negative | 0.773 | 1.404 | 0.140 | 14.049 |
| | ER/PR/HER2 positive | 0.423 | 0.533 | 0.112 | 2.540 |
| | HER2 positive | 0.784 | 1.276 | 0.224 | 7.282 |

Fig. 26

| Variables | | Univariate Analysis | | | Multivariate Analysis | | |
|---|---|---|---|---|---|---|---|
| | | p-value | Mean Hazard Ratio | 95% Hazard Ratio Confidence Limits | p-value | Mean Hazard Ratio | 95% Hazard Ratio Confidence Limits |
| CAStotal | High vs Low | <0.0001 | 5.2279 | 5.1152   5.3405 | <0.0001 | 6.5879 | 6.4381   6.7377 |

Fig. 27
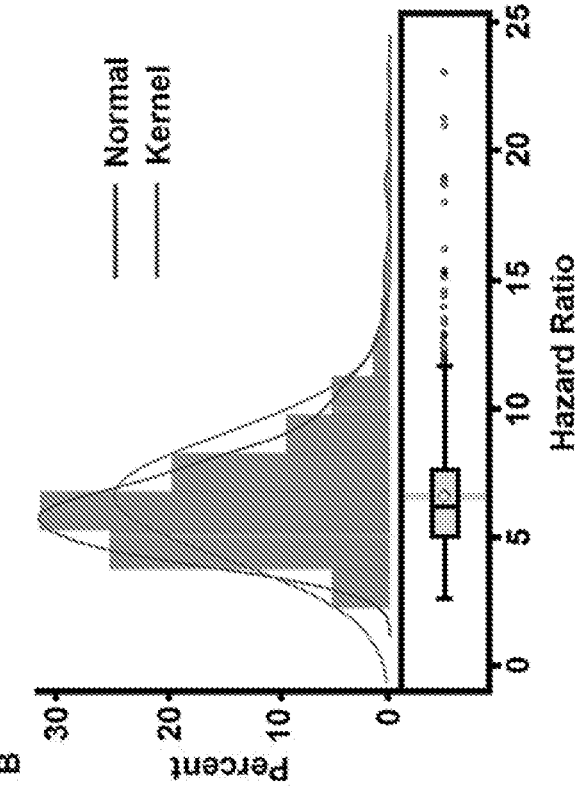
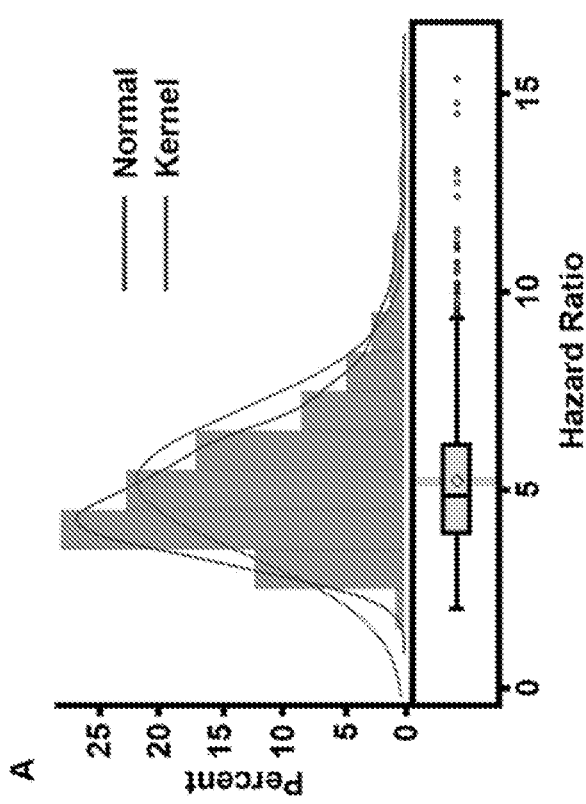

Fig. 28

A — Discovery Cohort patients with recurrence as DCIS

| Baseline Characteristics | Recurrence-Free | Local Recurrence | p-value |
|---|---|---|---|
| CAStotal, n(%) | | | |
| High | 49 (46.67) | 8 (80.00) | 0.044 |
| Low | 56 (53.33) | 2 (20.00) | |
| Patient Age, n(%) | | | |
| Age>50 | 87 (82.86) | 7 (70.00) | 0.315 |
| Age<=50 | 18 (17.14) | 3 (30.00) | |
| Tumor Size, n(%) | | | |
| Size>16 | 51 (48.57) | 7 (70.00) | 0.195 |
| Size<=16 | 54 (51.43) | 3 (30.00) | |
| Grade, n(%) | | | |
| High | 97 (92.38) | 9 (90.00) | 0.789 |
| Mid and Low | 8 (7.62) | 1 (10.00) | |
| Comedo Necrosis, n(%) | | | |
| No | 14 (13.33) | 1 (10.00) | 0.765 |
| Yes | 91 (86.67) | 9 (90.00) | |
| Radiotherapy, n(%) | | | |
| No | 57 (54.29) | 7 (70.00) | 0.339 |
| Yes | 48 (45.71) | 3 (30.00) | |
| Receptor Status, n(%) | | | |
| ER/PR/HER2-Positive | 3 (2.86) | 1 (10.00) | 0.138 |
| ER/PR-Positive and HER2-Negative | 19 (18.10) | 2 (20.00) | |
| HER2-Positive | 9 (8.57) | 3 (30.00) | |
| TNBC | 9 (8.57) | 1 (10.00) | |
| Missing | 65 (61.90) | 3 (30.00) | |

B — Discovery Cohort patients with recurrence as IBC

| Baseline Characteristics | Recurrence-Free | Local Recurrence | p-value |
|---|---|---|---|
| CAStotal, n(%) | | | |
| High | 49 (46.47) | 16 (88.89) | <0.001 |
| Low | 56 (53.33) | 2 (11.11) | |
| Patient Age, n(%) | | | |
| Age>50 | 87 (82.86) | 15 (83.33) | 0.960 |
| Age<=50 | 18 (17.14) | 3 (16.67) | |
| Tumor Size, n(%) | | | |
| Size>16 | 51 (48.57) | 8 (44.44) | 0.748 |
| Size<=16 | 54 (51.43) | 10 (55.56) | |
| Grade, n(%) | | | |
| High | 97 (92.38) | 12 (66.67) | 0.001 |
| Mid and Low | 8 (7.62) | 6 (33.33) | |
| Comedo Necrosis, n(%) | | | |
| No | 14 (13.33) | 7 (38.89) | 0.008 |
| Yes | 91 (86.67) | 11 (61.11) | |
| Radiotherapy, n(%) | | | |
| No | 57 (54.29) | 14 (77.78) | 0.062 |
| Yes | 48 (45.71) | 4 (22.22) | |
| Receptor Status, n(%) | | | |
| ER/PR/HER2-Positive | 3 (2.86) | 1 (5.56) | 0.376 |
| ER/PR-Positive and HER2-Negative | 19 (18.10) | 5 (27.78) | |
| HER2-Positive | 9 (8.57) | 0 (0.00) | |
| TNBC | 9 (8.57) | 0 (0.00) | |
| Missing | 65 (61.90) | 12 (66.67) | |

Validation Cohort patients and patients 45 DCIS

| Baseline Characteristics | Recurrence-Free | Local Recurrence | p-value |
|---|---|---|---|
| CAS total, n(%) | | | |
| High | 21 (22.11) | 10 (90.91) | <0.001 |
| Low | 74 (77.89) | 1 (9.09) | |
| Patient Age, n(%) | | | |
| Age>50 | 68 (71.58) | 4 (36.36) | 0.018 |
| Age<=50 | 27 (28.42) | 7 (63.64) | |
| Tumor Size, n(%) | | | |
| Size>16 | 81 (85.26) | 3 (27.27) | <0.001 |
| Size<=16 | 14 (14.74) | 8 (72.73) | |
| Grade, n(%) | | | |
| High | 47 (49.47) | 4 (36.36) | 0.410 |
| Mid and Low | 48 (50.53) | 7 (63.64) | |
| Comedo Necrosis, n(%) | | | |
| No | 37 (38.95) | 8 (72.73) | 0.032 |
| Yes | 58 (61.05) | 3 (27.27) | |
| Radiotherapy, n(%) | | | |
| No | 83 (87.37) | 9 (81.82) | 0.607 |
| Yes | 12 (12.63) | 2 (18.18) | |
| Receptor Status, n(%) | | | |
| ER/PR/HER2-Positive | 10 (10.53) | 1 (9.09) | 0.343 |
| ER/PR-Positive and HER2-Negative | 39 (41.05) | 8 (72.73) | |
| HER2-Positive | 13 (13.68) | 1 (9.09) | |
| TNBC | 6 (6.32) | 0 (0.00) | |
| Missing | 27 (28.42) | 1 (9.09) | |

B

Validation Cohort patients with radiation (n=96)

| Baseline Characteristics | Recurrence-Free | Local Recurrence | p-value |
|---|---|---|---|
| CAS total, n(%) | | | |
| High | 21 (22.11) | 6 (46.15) | 0.080 |
| Low | 74 (77.89) | 7 (53.85) | |
| Patient Age, n(%) | | | |
| Age>50 | 68 (71.58) | 8 (61.54) | 0.457 |
| Age<=50 | 27 (28.42) | 5 (38.46) | |
| Tumor Size, n(%) | | | |
| Size>16 | 81 (85.26) | 6 (46.15) | <0.001 |
| Size<=16 | 14 (14.74) | 7 (53.85) | |
| Grade, n(%) | | | |
| High | 47 (49.47) | 8 (61.54) | 0.414 |
| Mid and Low | 48 (50.53) | 5 (38.46) | |
| Comedo Necrosis, n(%) | | | |
| No | 58 (61.05) | 5 (38.46) | 0.121 |
| Yes | 37 (38.95) | 8 (61.54) | |
| Radiotherapy, n(%) | | | |
| No | 83 (87.37) | 13 (100.00) | 0.174 |
| Yes | 12 (12.63) | 0 (0.00) | |
| Receptor Status, n(%) | | | |
| ER/PR/HER2-Positive | 10 (10.53) | 2 (15.38) | 0.959 |
| ER/PR-Positive and HER2-Negative | 39 (41.05) | 5 (38.46) | |
| HER2-Positive | 13 (13.68) | 1 (7.69) | |
| TNBC | 6 (6.32) | 1 (7.69) | |
| Missing | 27 (28.42) | 4 (30.77) | |

Discovery Cohort DCIS Cox Regression

| Variables | | Multivariate Analysis | | 95% Hazard Ratio Confidence Limits | |
|---|---|---|---|---|---|
| | | p-value | Hazard Ratio | | |
| Recurrence-Free Survival | | | | | |
| CAStotal | High vs Low | 0.044 | 5.224 | 1.043 | 26.154 |
| Age | >50 years vs <=50 years | 0.353 | 0.484 | 0.105 | 2.239 |
| Grade | High vs intermediate/low | 0.825 | 0.758 | 0.066 | 8.743 |
| Comedo Necrosis | Present vs absent | 0.818 | 0.778 | 0.092 | 6.586 |
| Radiotherapy | No vs yes | 0.280 | 2.177 | 0.530 | 8.939 |

Aii

Discovery Cohort Invasive Cox Regression

| Variables | | Multivariate Analysis | | 95% Hazard Ratio Confidence Limits | |
|---|---|---|---|---|---|
| | | p-value | Hazard Ratio | | |
| Recurrence-Free Survival | | | | | |
| CAStotal | High vs Low | 0.001 | 11.050 | 2.459 | 49.659 |
| Age | >50 years vs <=50 years | 0.646 | 0.740 | 0.204 | 2.681 |
| Grade | High vs intermediate/low | 0.024 | 0.276 | 0.090 | 0.845 |
| Comedo Necrosis | Present vs absent | 0.102 | 2.353 | 0.844 | 6.559 |
| Radiotherapy | No vs yes | 0.568 | 1.430 | 0.418 | 4.890 |

Bi

Validation Cohort DCIS Cox Regression

| Variables | | Multivariate Analysis | | 95% Hazard Ratio Confidence Limits | |
|---|---|---|---|---|---|
| | | p-value | Hazard Ratio | | |
| Recurrence-Free Survival | | | | | |
| CAStotal | High vs Low | 0.002 | 26.771 | 3.366 | 212.920 |
| Age | >50 years vs <=50 years | 0.022 | 0.229 | 0.065 | 0.812 |
| Grade | High vs intermediate/low | 0.908 | 1.088 | 0.259 | 4.569 |
| Comedo Necrosis | Present vs absent | 0.072 | 5.582 | 0.860 | 36.241 |
| Radiotherapy | No vs yes | 0.570 | 0.576 | 0.086 | 3.870 |

Bii

Validation Cohort Invasive Cox Regression

| Variables | | Multivariate Analysis | | 95% Hazard Ratio Confidence Limits | |
|---|---|---|---|---|---|
| | | p-value | Hazard Ratio | | |
| Recurrence-Free Survival | | | | | |
| CAStotal | High vs Low | 0.165 | 2.361 | 0.703 | 7.931 |
| Age | >50 years vs <=50 years | 0.432 | 0.616 | 0.184 | 2.063 |
| Grade | High vs intermediate/low | 0.282 | 2.052 | 0.553 | 7.608 |
| Comedo Necrosis | Present vs absent | 0.090 | 3.068 | 0.839 | 11.218 |
| Radiotherapy | No vs yes | N/A | N/A | N/A | N/A |

Discovery cohort — Status at 10 years

| Variables | Censored | Recurred | Acc | Sn/Sp | PPV/NPV/OR |
|---|---|---|---|---|---|
| CAS | | | | | |
| High CAS | 49 | 24 | Acc 0.602 | Sn 0.857 | PPV 0.328 |
| Low CAS | 56 | 4 | Sp 0.533 | NPV 0.857 | OR 6.857 |
| Patient Age | | | | | |
| Age>50 | 87 | 22 | Acc 0.301 | Sn 0.786 | PPV 0.202 |
| Age<=50 | 18 | 6 | Sp 0.171 | NPV 0.750 | OR 0.758 |
| Tumor Size | | | | | |
| Size>16 | 51 | 15 | Acc 0.519 | Sn 0.536 | PPV 0.227 |
| Size<=16 | 54 | 13 | Sp 0.514 | NPV 0.806 | OR 1.222 |
| Grade | | | | | |
| High | 97 | 21 | Acc 0.218 | Sn 0.750 | PPV 0.178 |
| Low | 8 | 7 | Sp 0.076 | NPV 0.533 | OR 0.247 |
| Comedo Necrosis | | | | | |
| Absent | 14 | 8 | Acc 0.744 | Sn 0.286 | PPV 0.364 |
| Present | 91 | 20 | Sp 0.867 | NPV 0.819 | OR 2.600 |
| Radiotherapy | | | | | |
| No | 57 | 21 | Acc 0.519 | Sn 0.750 | PPV 0.269 |
| Yes | 48 | 7 | Sp 0.457 | NPV 0.873 | OR 2.526 |

B

Validation cohort — Status at 10 years

| Variables | Censored | Recurred | Acc | Sn/Sp | PPV/NPV/OR |
|---|---|---|---|---|---|
| CAS | | | | | |
| High CAS | 21 | 16 | Acc 0.756 | Sn 0.867 | PPV 0.432 |
| Low CAS | 74 | 8 | Sp 0.779 | NPV 0.902 | OR 7.048 |
| Patient Age | | | | | |
| Age>50 | 68 | 12 | Acc 0.328 | Sn 0.500 | PPV 0.150 |
| Age<=50 | 27 | 12 | Sp 0.284 | NPV 0.692 | OR 0.397 |
| Tumor Size | | | | | |
| Size>16 | 81 | 9 | Acc 0.193 | Sn 0.375 | PPV 0.100 |
| Size<=16 | 14 | 15 | Sp 0.147 | NPV 0.483 | OR 0.104 |
| Grade | | | | | |
| High | 47 | 12 | Acc 0.504 | Sn 0.500 | PPV 0.203 |
| Low | 48 | 12 | Sp 0.505 | NPV 0.800 | OR 1.021 |
| Comedo Necrosis | | | | | |
| Absent | 37 | 16 | Acc 0.622 | Sn 0.667 | PPV 0.302 |
| Present | 58 | 8 | Sp 0.611 | NPV 0.879 | OR 3.135 |
| Radiotherapy | | | | | |
| No | 83 | 22 | Acc 0.286 | Sn 0.917 | PPV 0.209 |
| Yes | 12 | 2 | Sp 0.126 | NPV 0.857 | OR 1.590 |

Fig. 39A

10 year recurrence rate with 95%
CI under different risk categories

Recurrence rates based on
CAStotal high/low risk subcategory

All patients 118
Comedo No 14
High CAStotal 8
Low CAStotal 6
Comedo Yes 104
High CAStotal 59
Low CASt0total 45
Age High 100
High CAStotal 57
Low CAStotal 43
Age Low 18
High CAStotal 10
Low CAStotal 8
Size High 54
High CAStotal 30
Low CAStotal 24
Size Low 64
High CAStotal 37
Low CAStotal 27
Radiotherapy No 64
High CAStotal 35
Low CAStotal 29
Radiotherapy Yes 54
High CAStotal 32
Low CAStotal 22

10 year recurrence rate with 95% under different risk categories

Recurrence rates based on CAStotal high/low risk subcategory

Fig. 40

| Variables | Univariate Analysis | | | |
|---|---|---|---|---|
| | p-value | Hazard Ratio | 95% Hazard Ratio Confidence Limits | |
| Recurrence-Free Survival | | | | |
| CAStotal | <0.001 | 5.602 | 2.173 | 14.441 |
| VNPI | 0.312 | 0.708 | 0.362 | 1.383 |

Fig. 41

| Recurrence-Free Survival | Multivariate Analysis | | | |
|---|---|---|---|---|
| Variables | p-value | Hazard Ratio | 95% Hazard Ratio Confidence Limits | |
| CAStotal | <0.001 | 6.867 | 2.594 | 18.177 |
| VNPI | 0.025 | 0.381 | 0.164 | 0.884 |
| Age | <0.001 | 0.227 | 0.102 | 0.502 |
| Size | 0.238 | 1.556 | 0.747 | 3.239 |
| Comedo necrosis | 0.067 | 2.060 | 0.951 | 4.465 |
| Radiotherapy | 0.046 | 3.261 | 1.022 | 10.406 |

228

Fig. 43b
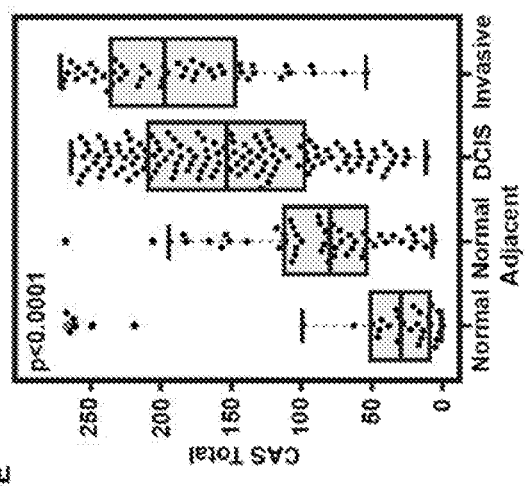
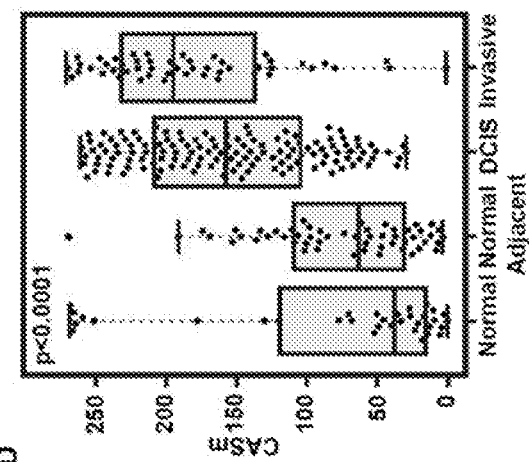
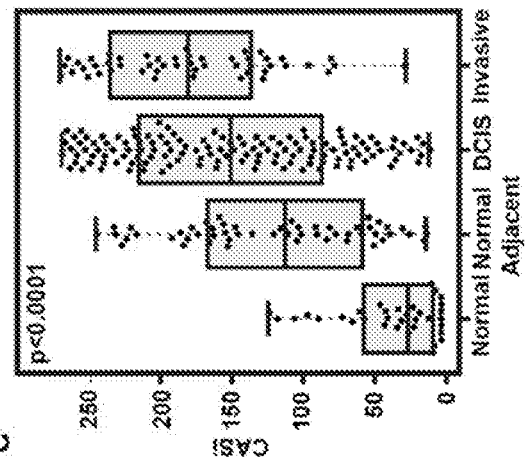

QUANTITATIVE CENTROSOMAL AMPLIFICATION SCORE TO PREDICT LOCAL RECURRENCE OF DUCTAL CARCINOMA IN SITU

CROSS-REFERENCE TO RELATED APPLICATIONS

This application claims the benefit of U.S. Provisional Application No. 62/776,144, filed Dec. 6, 2018, the contents of which are incorporated herein in their entirety.

BACKGROUND

The present invention relates to techniques that provide improved capability to predict the risk of recurrence of DCIS and other non-invasive carcinomas in situ cancer conditions using a quantitative centrosomal amplification score.

Approximately 20% of screen-detected breast cancers (BC) are Ductal Carcinoma In Situ (DCIS), a pre-invasive form of BC wherein malignant epithelial cells are confined to the lumen of a mammary duct and do not invade into the adjacent stroma. Notably, 20-53% of women with untreated DCIS progress to invasive BC over a period of ≥10 years. Since the progressive potential of a DCIS lesion cannot be reliably determined, local control via surgical excision with or without local radiotherapy is the mainstay strategy, with addition of endocrine blockade in some cases. Unfortunately, 10-35% of DCIS patients treated with lumpectomy or breast conservation surgery (BCS) later present with a local recurrence (LR) and about half of all recurrences occur in the form of invasive breast cancer (IBC). A major challenge is to avoid under- or over-treatment by developing prognostic biomarkers that can stratify patients diagnosed with DCIS or other non-invasive carcinomas in situ based on their recurrence risk.

Current predictors of recurrence risk for DCIS such as the Van Nuys Prognostic Index (VNPI) and the Memorial Sloan Kettering DCIS nomogram are based on routinely-used clinicopathological parameters but lack consistency and reproducibility in risk prediction. In addition, these tools do not integrate prognostically-informative molecular predictors, and underestimate DCIS heterogeneity. While Oncotype Dx Breast DCIS score, a commercially-available gene-expression based assay, has some value in predicting LR, it has only been validated in two cohorts (ECOG E5194 and Ontario DCIS). The poor stratification of high/intermediate-risk patients in these two cohorts has called into question the prognostic value of this tool.

Extensive genetic and phenotypic intratumoral heterogeneity (ITH) characterizes DCIS. In a pre-invasive lesion, higher ITH predicts greater likelihood of LR and invasive BC. Amplified centrosomes underlie erroneous mitoses and fuel chromosomal instability (CIN), which is a well-recognized driver of ITH. Although normal cells have one centrosome pre-S-phase and two centrosomes post-S-phase, cancer cells invariably display centrosome amplification (CA); an abnormal increase in the number (i.e., numerical amplification) and/or volume (i.e., structural amplification) of centrosomes.

Accordingly, a need arises for techniques that provide improved capability to predict the risk of recurrence of DCIS or other non-invasive carcinomas in situ, as well as to provide more personalized therapy and reduce the risk of over-treatment or under-treatment.

SUMMARY

Embodiments of the present systems and methods may provide improved capability to predict the risk of recurrence of ductal carcinoma in situ (DCIS) conditions or other non-invasive carcinoma in situ. Embodiments may utilize differences in in the extent and/or type of CA to distinguish recurrent and non-recurrent DCIS. Embodiments may provide a methodology for the rigorous quantitation of CA phenotypes, as well as using the prognostic value of numerical and/or structural CA. Embodiments may utilize the two features of CA-frequency (i.e., percentage of cells showing amplified centrosomes), and/or severity (i.e., how abnormal the number/volume of centrosomes is in a given sample) for prognostic purposes.

Embodiments may provide a methodology for centrosomal phenotyping to quantitate both numerical and structural centrosomal aberrations in clinical tissue samples. Centrosomes may be immunofluorescently stained using an antibody against γ-tubulin, and nuclei may be co-stained with Hoechst. Embodiments of the analytical procedure may provide robust interrogation of the capacity of centrosomal overload to predict the risk of LR after a lumpectomy. Embodiments may provide an algorithm that quantitates the frequency/prevalence and severity of CA (both numerical and structural) in formalin-fixed paraffin-embedded (FFPE) clinical samples, and computes a centrosome amplification score (CAS) for each sample. Embodiments may use CAS as a metric that may improve treatment recommendations and allow identification of patients at low risk of recurrence for whom adjuvant radiotherapy (RT) may not be required. CAS demonstrates the highest concordance among the known prognostic models such as VNPI and commonly used clinicopathological variables such as grade, age, and comedo necrosis.

Embodiments may utilize FFPE full-face sections, tissue microarrays, biopsies, fresh frozen sections and sections fixed with a variety of other fixation protocols, cells in culture, fine needle aspirates, circulating tumor cells, or tumor cells dislodged (from tumor) or isolated or cultured using any other means (including patient-derived xenografts or primary cultures). Likewise, embodiments may utilize staining the nucleus, staining cell boundaries, or otherwise visualizing cell boundaries. Further, embodiments may determine the normal 3-D volume range by staining any component of the pericentriolar material (using a procedure similar to that used in herein) or staining individual centrioles, as long as an appropriate volume range/cutoff for normal tissue is used to define iCTRs vs mCTRs. In embodiments, centrosomes may also be labelled using immunohistochemistry and appropriate volumes may be determined. Similarly, transmission electron microscopy may be utilized. Further, centrosome volumes may also be determined if the tumor cells are transfected with plasmids or viruses expressing epitope-tagged or fluorescently-tagged proteins that are PCM or centriole components and would localize to centrosomes.

For example, in an embodiment, a method of determining a 10 year risk of local recurrence of a patient diagnosed with a carcinoma in situ may comprise determining severity and frequency of numerical and structural centrosome amplification present within a sample of a carcinoma in situ from the patient, and determining at least one centrosome amplification score (CAS) value for the sample based on the determined severity and frequency of numerical and structural centrosome amplification in the sample, wherein the determined at least one CAS value provides a measure of a level of a 10 year risk of local recurrence associated with the carcinoma in situ.

In embodiments, determining severity and frequency may comprise (a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei, (b) determining a volume of each iCTR and mCTR in the ROI, and (c) determining numbers of iCTRs and mCTRs associated with each cell nucleus in the ROI, wherein a centrosome is categorized as an iCTR when the volume of the centrosome is within a range of volumes found in normal tissue, and a centrosome is categorized as an mCTR when the volume the centrosome is greater than the range of volumes found in normal tissue. The range of volumes found in normal tissue may be about 0.20-0.74 cubic microns for breast tissue stained to visualize gamma-tubulin distribution. Determining at least one CAS value may comprise (d) calculating at least one structural CAS value for the sample based on the determined volumes of each iCTR and mCTR in the ROI, wherein the total structural CAS value is an aggregate value of both frequency and severity of structural centrosome amplification, (e) calculating at least one numerical CAS value for the sample based on the determined numbers of iCTRs and mCTRs associated with each cell nucleus in the ROI, wherein the total numerical CAS value is an aggregate value of both frequency and severity of numerical centrosome amplification, and (f) calculating at least one total CAS value for the sample based the at least one structural CAS value and the at least one numerical CAS value, wherein the at least one structural CAS value, the at least one numerical CAS value, and the at least one total CAS value provides a measure of a level of a 10 year risk of local recurrence associated with the carcinoma in situ.

In embodiments, an above-threshold CAS value may indicate a greater risk of local recurrence of the carcinoma in situ than does a below-threshold CAS value. The CAS value may be an independent predictor of relapse-free survival after accounting for potentially confounding factors including at least one of tumor grade, patient age, comedo necrosis, patient treatment with radiotherapy, and receptor status. An above-threshold numerical CAS value may indicate a greater risk of local recurrence of the carcinoma in situ than does a below-threshold numerical CAS value. An above-threshold structural CAS value may indicate a greater risk of local recurrence of the carcinoma in situ than does a below-threshold structural CAS value. An above-threshold total CAS value may indicate a greater risk of local recurrence of the carcinoma in situ than does a below-threshold total CAS value. The total CAS value may stratify patients into those at high risk of recurrence of carcinoma in situ and into those at low risk of recurrence of carcinoma in situ. The total CAS value may stratify patients into those at high risk of recurrence of carcinoma in situ and into those at low risk of recurrence of carcinoma in situ after accounting for confounding factors including at least one of tumor grade, patient age, comedo necrosis, patient treatment with radiotherapy, and receptor status and wherein the stratification provided by the total CAS value is superior to the stratification provided by the Van Nuys Prognostic Index. An above-threshold total CAS value may indicate patients that have had breast conservation surgery for the carcinoma in situ who would benefit from adjuvant radiotherapy.

In an embodiment, a computer program product for determining the risk profile of a patient diagnosed with a carcinoma in situ, the computer program product comprising a non-transitory computer readable storage having program instructions embodied therewith, the program instructions executable by a computer, to cause the computer to perform a method comprising determining severity and frequency of numerical and structural centrosome amplification present within a sample of a carcinoma in situ from the patient, determining at least one centrosome amplification score (CAS) value for the sample based on the determined severity and frequency of numerical and structural centrosome amplification in the sample, wherein the determined at least one CAS value provides a measure of a level of a 10 year risk of local recurrence associated with the carcinoma in situ.

In embodiments, determining severity and frequency may comprise (a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei, (b) determining a volume of each iCTR and mCTR in the ROI, and (c) determining numbers of iCTRs and mCTRs associated with each cell nucleus in the ROI, wherein a centrosome is categorized as an iCTR when the volume of the centrosome is within a range of volumes found in normal tissue, and a centrosome is categorized as an mCTR when the volume the centrosome is greater than the range of volumes found in normal tissue. The range of volumes found in normal tissue may be about 0.20-0.74 cubic microns for breast tissue stained to visualize gamma-tubulin distribution. Determining at least one CAS value may comprise (d) calculating at least one structural CAS value for the sample based on the determined volumes of each iCTR and mCTR in the ROI, wherein the total structural CAS value is an aggregate value of both frequency and severity of structural centrosome amplification, (e) calculating at least one numerical CAS value for the sample based on the determined numbers of iCTRs and mCTRs associated with each cell nucleus in the ROI, wherein the total numerical CAS value is an aggregate value of both frequency and severity of numerical centrosome amplification, and (f) calculating at least one total CAS value for the sample based the at least one structural CAS value and the at least one numerical CAS value, wherein the at least one structural CAS value, the at least one numerical CAS value, and the at least one total CAS value provides a measure of a level of a 10 year risk of local recurrence associated with the carcinoma in situ.

In embodiments, an above-threshold CAS value may indicate a greater risk of local recurrence of the carcinoma in situ than does a below-threshold CAS value. The CAS value may be an independent predictor of relapse-free survival after accounting for potentially confounding factors including at least one of tumor grade, patient age, comedo necrosis, patient treatment with radiotherapy, and receptor status. An above-threshold numerical CAS value may indicate a greater risk of local recurrence of the carcinoma in situ than does a below-threshold numerical CAS value, an above-threshold structural CAS value may indicate a greater risk of local recurrence of the carcinoma in situ than does a below-threshold structural CAS value, an above-threshold total CAS value may indicate a greater risk of local recurrence of the carcinoma in situ than does a below-threshold total CAS value, the total CAS value may stratify patients into those at high risk of recurrence of carcinoma in situ and into those at low risk of recurrence of carcinoma in situ, the total CAS value may stratify patients into those at high risk of recurrence of carcinoma in situ and into those at low risk of recurrence of carcinoma in situ after accounting for confounding factors including at least one of tumor grade, patient age, comedo necrosis, patient treatment with radiotherapy, and receptor status, the stratification provided by the total CAS value may be superior to the stratification provided by the Van Nuys Prognostic Index, and an above-threshold total CAS value may indicate patients that have had surgery for the carcinoma in situ who would benefit from adjuvant radiotherapy. An above-threshold total CAS value may indicate patients that have had breast conservation surgery for the carcinoma in situ who would benefit from adjuvant radiotherapy.

BRIEF DESCRIPTION OF THE DRAWINGS

The details of the present invention, both as to its structure and operation, can best be understood by referring to the accompanying drawings, in which like reference numbers and designations refer to like elements.

FIGS. 2a and 2b are an exemplary flow diagram of semi-automated workflow process to quantify CA in clinical samples in accordance with embodiments of the present techniques.

FIGS. 3a and 3b show descriptive statistics of clinico-pathological characteristics of pure DCIS cases in the discovery cohort (DC) and validation cohort (VC) based on the recurrence status in accordance with embodiments of the present techniques.

FIGS. 4a and 4b show univariate and multivariate Cox proportional regression analysis for the risk of LR in DCIS patients treated with breast conserving surgery (BCS) or mastectomy comparing the influence of common clinico-pathological variables relative to CAStotal in the DC and VC, respectively, in accordance with embodiments of the present techniques.

FIGS. 5a and 5b are exemplary illustrations showing that DCIS cases in the DC with ipsilateral recurrence exhibit higher CAS than recurrence-free cases and showing that CAStotal was considered statistically significant in the VC, in accordance with embodiments of the present techniques.

FIG. 15 is an exemplary illustration showing DCIS cases in the DC and VC with LR exhibit higher frequency and severity of both numerical and structural CA in accordance with embodiments of the present techniques.

FIG. 16 is an exemplary illustration showing means scores and p-values of CASi, CASm and CAStotal in recurrence and recurrence free cases in DC in accordance with embodiments of the present techniques.

FIG. 21 is an exemplary illustration showing the Hazard Ratio and p value for the severity and frequency of CASi and CASm in DC in accordance with embodiments of the present techniques.

FIG. 24 is an exemplary illustration showing univariate Cox proportional regression analysis in accordance with embodiments of the present techniques.

FIG. 25 is an exemplary illustration showing multivariate Cox proportional regression analysis in accordance with embodiments of the present techniques.

FIG. 26 is an exemplary illustration showing a table representing the Hazard Ratios from univariate and multivariate bootstrap analysis for CAStotal (high vs low) in accordance with embodiments of the present techniques.

FIG. 27 is an exemplary illustration showing fitted normal and kernel density curves on the histogram in accordance with embodiments of the present techniques.

FIG. 28 is an exemplary illustration showing descriptive statistics of clinicopathological characteristics for pure DCIS cases in the DC in accordance with embodiments of the present techniques.

FIG. 29 is an exemplary illustration showing descriptive statistics of clinicopathological characteristics for pure DCIS cases in the VC in accordance with embodiments of the present techniques.

FIG. 30 is an exemplary illustration showing multivariate Cox proportional regression analysis for the risk of LR in DCIS treated with BCS or mastectomy comparing the influence of common clinicopathological variables and receptor status relative to CAStotal in (Panel A) DC where recurrence was in DCIS form, (Panel Aii) DC where recurrence was in invasive form (Panel Bi) VC where recurrence was in DCIS form (Panel Bii) VC where recurrence was in invasive form, in accordance with embodiments of the present techniques.

FIG. 31 is an exemplary illustration showing the 2×2 confusion matrix and performance metrics in accordance with embodiments of the present techniques.

FIGS. 39A and 39B are exemplary illustrations showing CAStotal allows deeper stratification of patient subgroups than traditional clinicopathologic parameters alone in accordance with embodiments of the present techniques.

FIG. 40 is an exemplary illustration showing univariate analyses evaluating the impact of CAStotal and VNPI on the RFS of DCIS patients treated with BCS in accordance with embodiments of the present techniques.

FIG. 41 is an exemplary illustration showing multivariate analyses evaluating the impact of CAStotal, VNPI and other clinicopathological parameters on the RFS of DCIS patients treated with BCS in accordance with embodiments of the present techniques.

FIGS. 43a and 43b are exemplary illustrations of representative H&E images, confocal micrographs, and Beeswarm Box plots in accordance with embodiments of the present techniques.

DETAILED DESCRIPTION

Figure 1A:
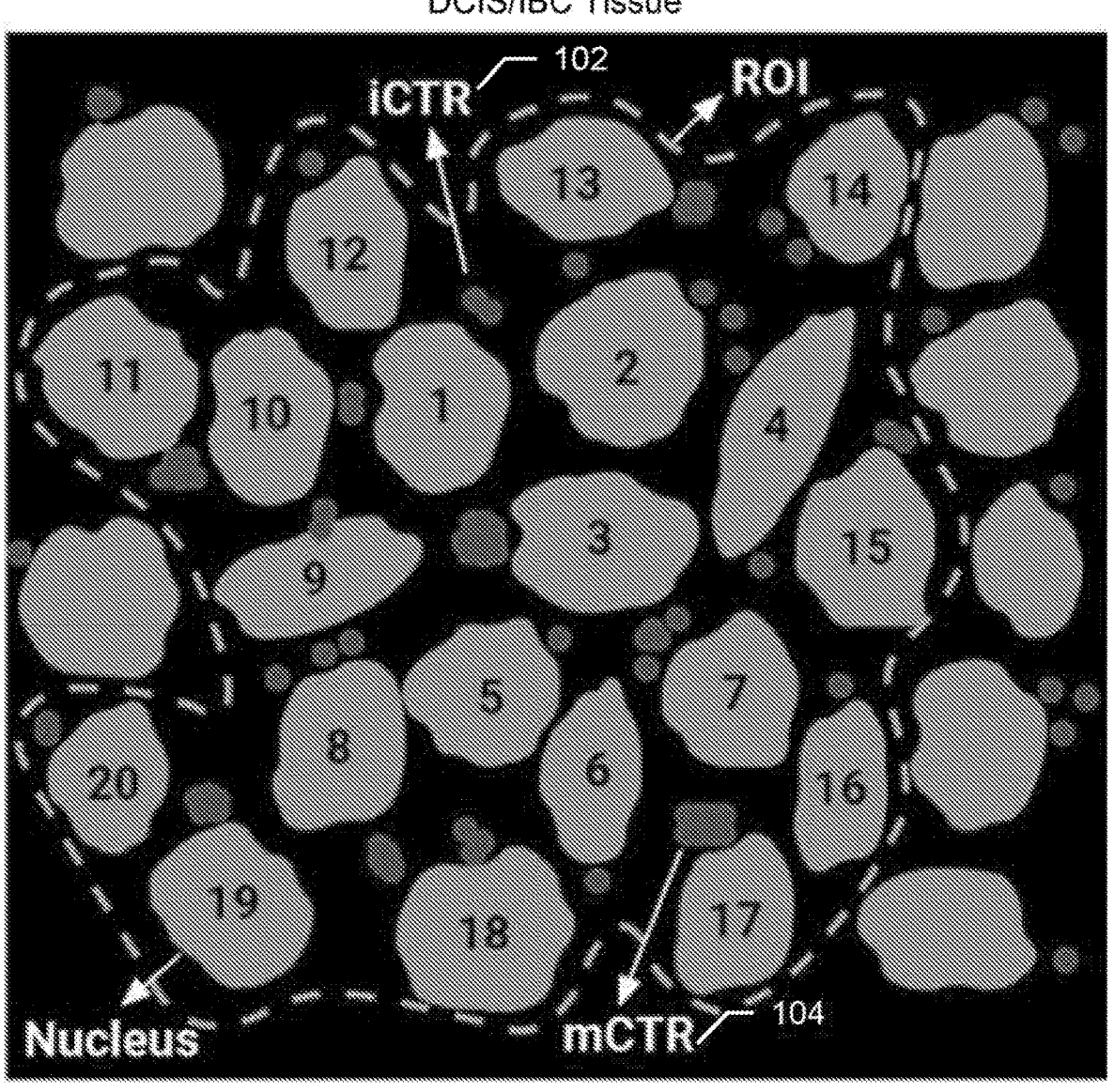
FIG. 1a is an exemplary illustration of centrosomes in breast tissues (normal, DCIS or IBC) that were categorized into individually distinguishable centrosomes (iCTRs) and megacentrosomes (mCTRs) in accordance with embodiments of the present techniques.

Embodiments of the present systems and methods may provide improved capability to predict the risk of recurrence of ductal carcinoma in situ (DCIS) conditions or other non-invasive carcinoma in situ. Embodiments may utilize differences in in the extent and/or type of CA to distinguish recurrent and non-recurrent DCIS. Embodiments may provide a methodology for the rigorous quantitation of CA phenotypes, as well as using the prognostic value of numerical and/or structural CA. Embodiments may utilize the two features of CA-frequency (i.e., percentage of cells showing amplified centrosomes), and/or severity (i.e., how abnormal the number/volume of centrosomes is in a given sample) for prognostic purposes. Although DCIS is used as an example herein, the present techniques may be equally applied to other non-invasive carcinoma in situ, as well as to other conditions, such as evaluation after breast conservation surgery, etc.

In embodiment, the methodology may evaluate the severity and frequency of numerical and structural CA present within DCIS, and may assign a quantitative centrosomal amplification score (CAS) to each sample. For example, analyses were performed in a discovery cohort (DC, n=133) and a validation cohort (VC, n=119).

Embodiments may provide results indicating that DCIS cases with LR exhibited significantly higher CAS than recurrence-free cases. Higher CAS may be associated with a greater risk of developing LR (HR=6.3 and 4.8 for DC and VC, respectively; p<0.001). CAS remained an independent predictor of relapse-free survival (HR=7.4 and 4.5 for DC and VC, respectively; p<0.001) even after accounting for potentially confounding factors (grade, age, comedo necrosis and radiotherapy). Patient stratification using CAS (p<0.0001) may be superior to that by Van Nuys Prognostic Index (VNPI) (HR for CAS=6.2, vs. HR for VNPI=1.1). Among patients treated with breast-conserving surgery alone, CAS identified patients likely to benefit from adjuvant radiotherapy (RT).

For example, in embodiments, CAS predicted 10-year LR risk for patients who underwent surgical management alone and identified patients who may be at low risk of recurrence, and for whom adjuvant RT may not be required. CAS demonstrated the highest concordance among the known prognostic models such as VNPI and clinicopathological variables such as grade, age, and comedo necrosis.

In embodiments, the present techniques quantitated amplified centrosomes using a semi-automated pipeline technology that integrates immunofluorescence confocal microscopy with digital image analysis to generate a quantitative centrosome amplification score (CAS). CAS is a summation of the severity and frequency of centrosomal aberrations in clinical tumor samples. Embodiments may be utilized in developing CAS as a readily quantifiable bio-marker that can predict the risk of local recurrence (LR) in DCIS with higher concordance than existing predictive tools. CAS may stratify lumpectomy cases into "low-CA DCIS" and "high-CA DCIS" wherein "high-CA DCIS" are much more likely to have LR, thereby aiding treatment decision-making. Embodiments may highlight organellar-level differences between recurrent and non-recurrent DCIS. CAS may serve as a promising new clinical tool to aid decision-making and improve treatment recommendations for DCIS patients.

Embodiments may provide a methodology for cen-trosomal phenotyping to quantitate both numerical and structural centrosomal aberrations in clinical tissue samples. Centrosomes may be immunofluorescently stained using an antibody against γ-tubulin, and co-stained nuclei with Hoechst. Embodiments of the analytical procedure may provide robust interrogation of the capacity of centrosomal overload to predict the risk of LR after a lumpectomy. Embodiments may provide an algorithm that quantitates the frequency/prevalence and severity of CA (both numerical and structural) in formalin-fixed paraffin-embedded (FFPE) clinical samples, and computes a centrosome amplification score (CAS) for each sample. Embodiments may use CAS as a metric that may improve treatment recommendations and allow identification of patients at low risk of recurrence for whom adjuvant RT may not be required. CAS demon-strates the highest concordance among the known prognostic models such as VNPI and commonly used clinicopathologi-cal variables such as grade, age, and comedo necrosis.

Embodiments may utilize FFPE full-face sections, tissue microarrays, biopsies, fresh frozen sections and sections fixed with a variety of other fixation protocols, cells in culture, fine needle aspirates, circulating tumor cells, or tumor cells dislodged (from tumor) or isolated or cultured using any other means (including patient-derived xenografts or primary cultures). Likewise, embodiments may utilize staining the nucleus, staining cell boundaries, or otherwise visualizing cell boundaries.

Materials and Methods

Clinical Tissue Samples

Figure 8:
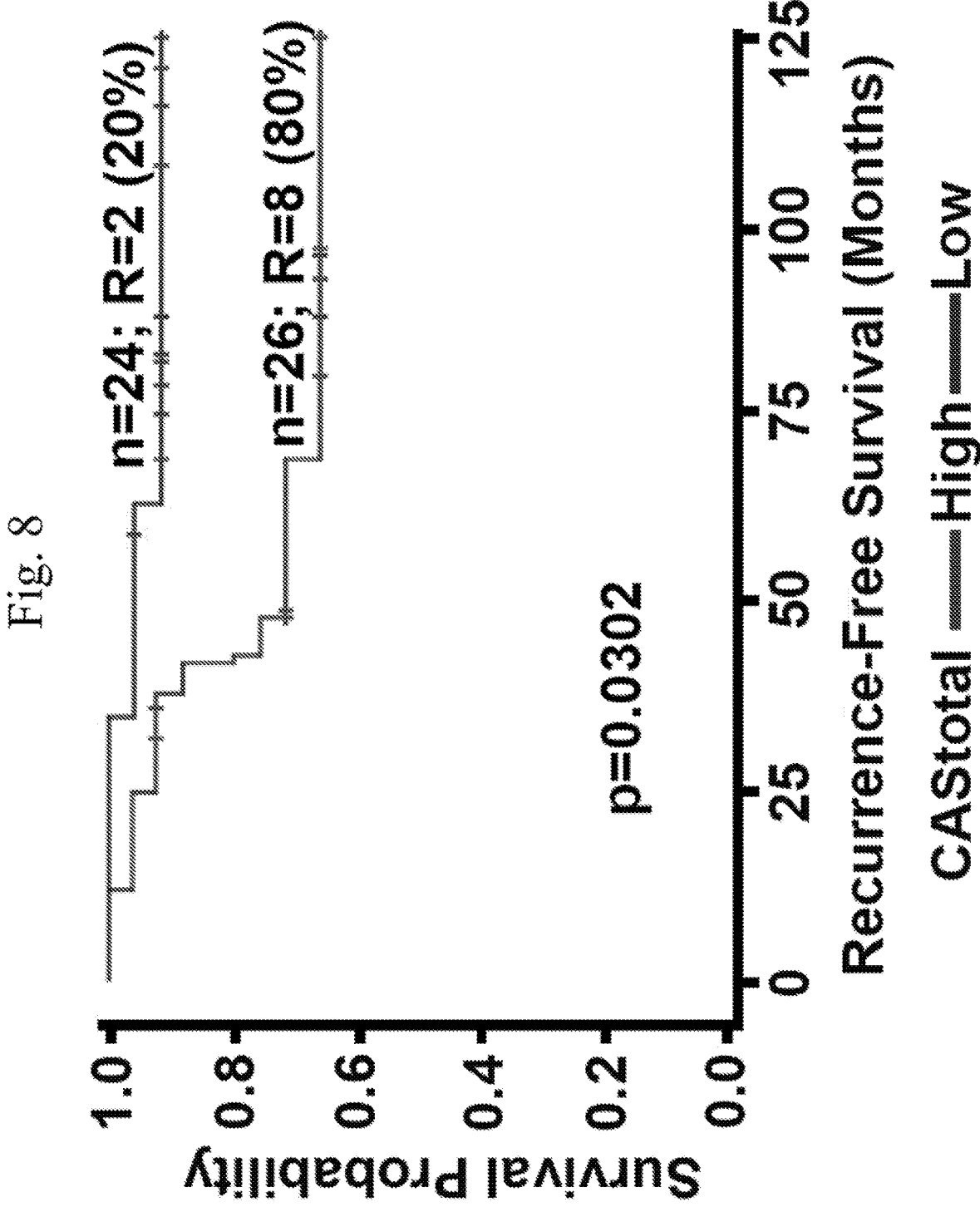
FIG. 8 is an exemplary illustration showing Kaplan Meier survival curves representing the RFS of patients in the DC stratified into "CAStotal" high and low groups in a cohort of 50 patients in accordance with embodiments of the present techniques.

A retrospective study was conducted that included FFPE tissue sections of primary pure DCIS consecutively diag-nosed between 1988 and 2012 that were obtained from Nottingham City Hospital, UK. Tumor tissues were pre-served by standard approved processing methods using formalin fixation and embedding in paraffin. These tumor blocks were stored in the Nottingham tissue bank. Cases that had (a) adequate amount of tissue, (b) all relevant clinico-pathologic data available, and (c) at least 10 years of follow-up were eventually included in the study. The samples for the study were shared in three batches. For the pilot study to estimate the sample size, samples for the first 50 consecutive cases that met inclusion criteria were shared and based upon our findings, the proposed sample size of 116 for each cohort was expected to yield a power of 80% with an alpha of 0.05 (FIG. 8). FIG. 8 shows Kaplan Meier survival curves representing the RFS of patients in the DC stratified into "CAStotal" high and low groups in a cohort of 50 patients.

Subsequently, samples for the next 83 cases were shared which together with the earlier 50 samples formed the discovery cohort (DC). The validation cohort (VC) was received only after the study (staining, imaging, and image analysis) on the DC was completed. To exclude any bias, the

10

Figure 9:
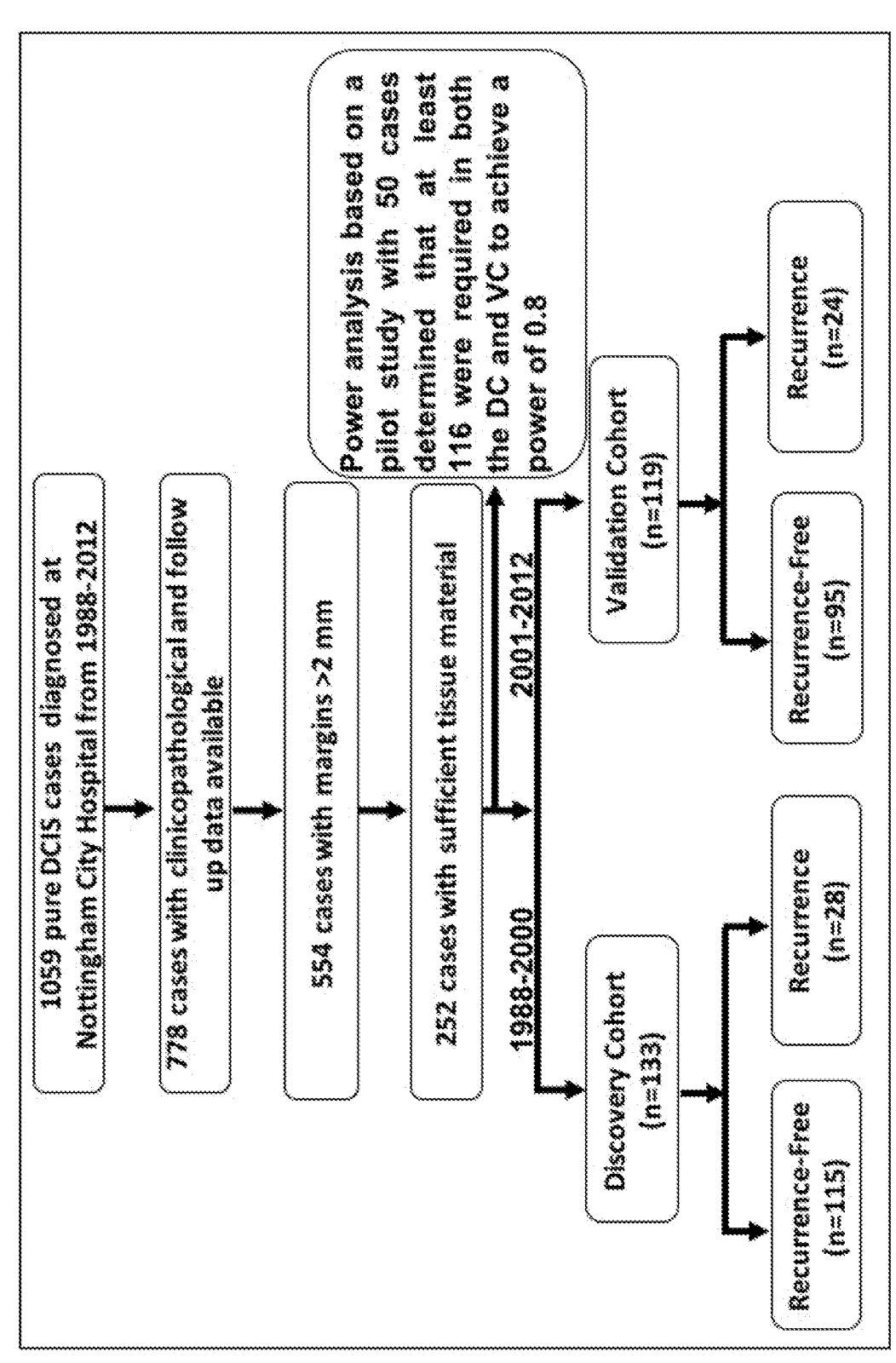
FIG. 9 is an exemplary illustration showing a REMARK diagram describing the flow of patients through the study, including the number of patients included in each stage of the analysis in accordance with embodiments of the present techniques.

GSU research group was totally blinded to clinicopathologic and outcome details of the patients included in the study. These data were not shared with GSU research team who performed the staining, imaging, and image analysis until the CAS scores were generated for each patient in all cohorts. The discovery cohort (DC) (n=133) and validation cohort (VC) (N=119) comprised of consecutive pure DCIS patients (no evidence of microinvasive or invasive breast cancer) with available tissue samples that showed free surgical margins >2 mm (to avoid the effect of this con-founder on the study outcome) and underwent BCS or mastectomy with or without adjuvant radiotherapy (RT) (FIG. 9). FIG. 9 shows a REMARK diagram describing the flow of patients through the study, including the number of patients included in each stage of the analysis.

All cases were histologically reviewed, and diagnoses were confirmed by two independent pathologists, and in case of disagreement between the two reviewing patholo-gists the specialist breast pathologist (EAR) confirmed the diagnosis. All cases were accompanied by data pertaining to their clinicopathologic variables such as age at diagnosis, menopausal status, DCIS size, nuclear grade, presence of comedo-type necrosis, treatment, VNPI, Ki67 proliferation index, and information about treatment (adjuvant RT), recur-rence-free survival (RFS) defined by the time (in months) between 6 months after the first surgery and occurrence of ipsilateral LR in the form of either DCIS or IBC, date of initial diagnosis, date of surgery, and patient status at last contact (23). Patients who underwent completion surgery within the first 6 months after primary resection surgery due to positive/close surgical margins or presence of residual tumor tissue were not considered to have disease recurrence. All patients who developed contralateral breast events were censored at the time of development of the contralateral tumor. None of the patients in our discovery/validation cohorts received adjuvant endocrine therapy.

To determine normal volumes of the centrosomes, full-face sections of normal breast tissue from reduction mam-moplasties (n=40) and breast tumors with extensive regions of adjacent uninvolved tissues (n=40) were obtained from Stavanger University Hospital, Norway, Nottingham City Hospital, UK, and West Georgia Hospital, GA, USA. All study aspects were (a) approved by every Institutional Review Board, and (b) in compliance with guidelines in material transfer and data use agreements for all involved institutions, and Georgia State University. Informed consent was obtained from all subjects.

Figure 1B:
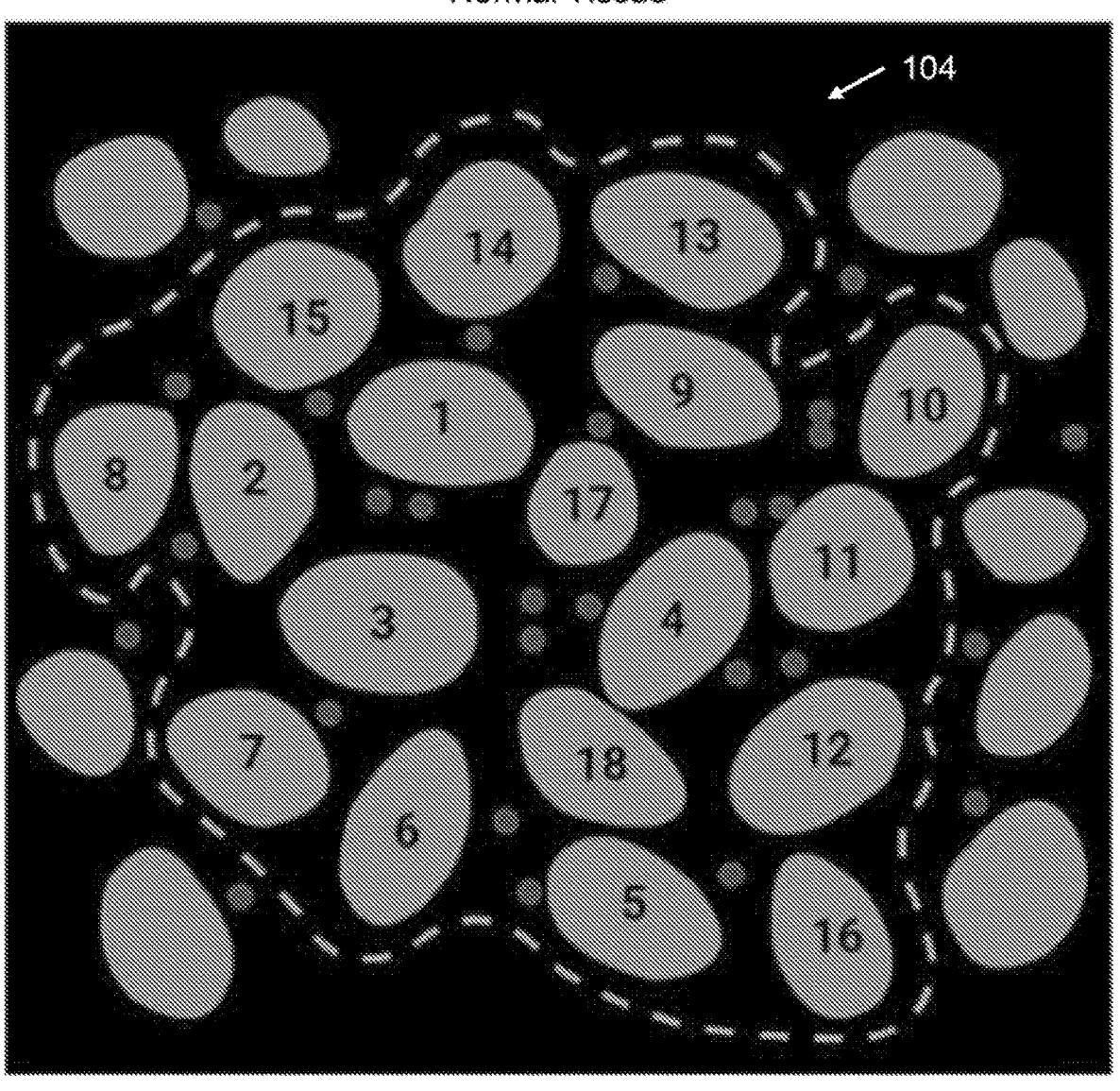
FIG. 1b is an exemplary illustration of centrosomes in normal tissue in accordance with embodiments of the present techniques.

FIG. 1a illustrates centrosomes in breast tissues (normal, DCIS or IBC) that were categorized into individually dis-tinguishable centrosomes (iCTRs 102) and megacen-trosomes (mCTRs 104). iCTRs 102 were defined as cen-trosomes that stain positive for γ-tubulin and whose volumes lie within the range of centrosome volumes found in normal breast tissue stained for γ-tubulin. FIG. 1b illustrates mCTRs 104 that were defined as centrosomes in a neoplastic region that stain positive for γ-tubulin and whose volume is greater than the upper limit of the centrosome volume range found in corresponding normal tissue immunostained for γ-tubulin. Thus, mCTRs are centrosomes with aberrantly large vol-umes and are considered to represent structurally amplified centrosomes.

Figure 2A:
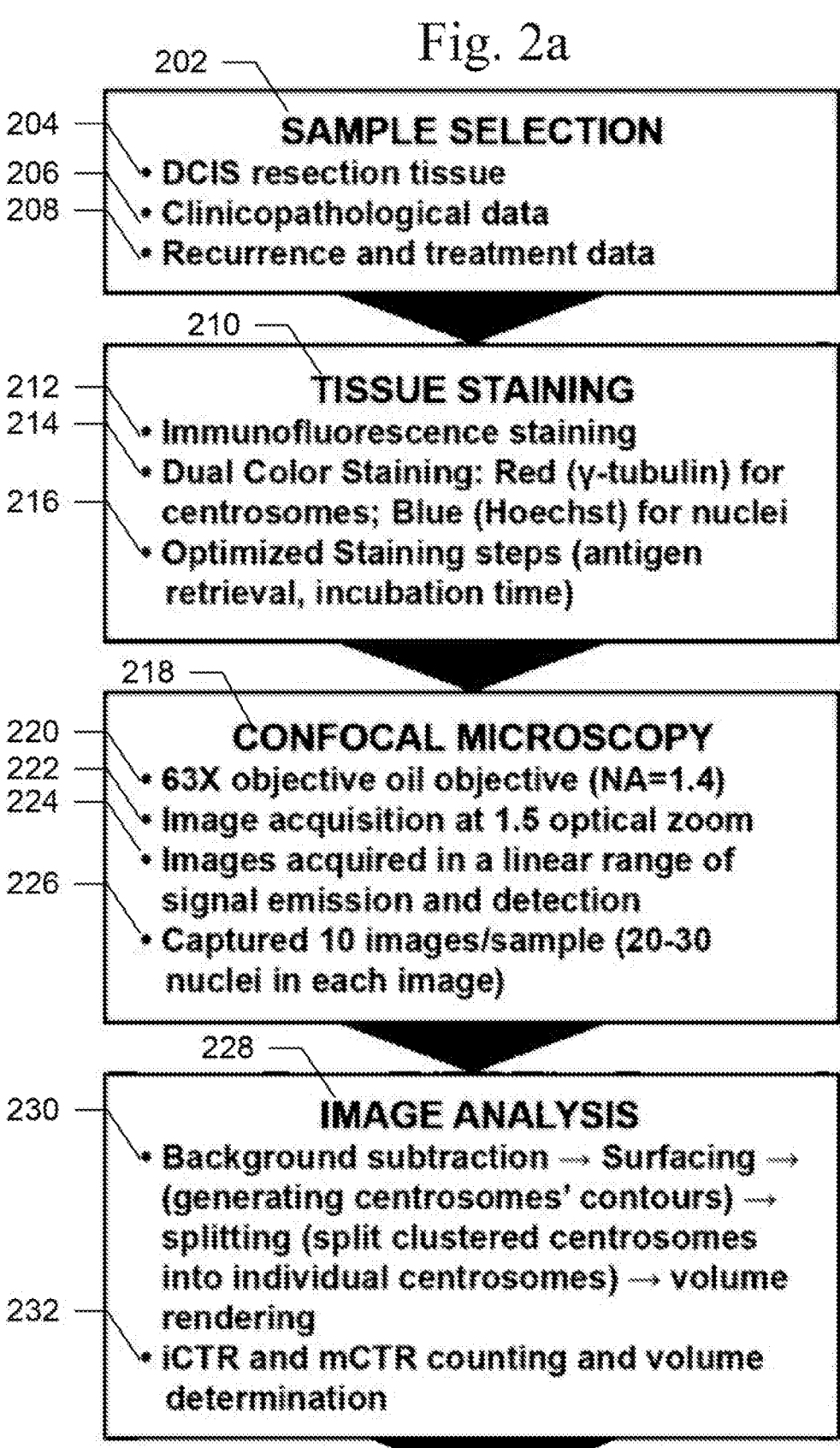

FIGS. 2a and 2b illustrate an example of a semi-auto-mated workflow to quantify CA in clinical samples. At 202, sample selection may be performed. At 204, DCIS resection tissue from patients or subjects may be obtained. Samples may be obtained from surgically removed tumors/biopsies, or fine-needle aspirate or any cell suspension, cells isolated from body fluid samples or cells dislodged from tumor by any other means. At 206, clinicopathological data from the patients or subjects may be obtained. At 208, recurrence and treatment data for the patients or subjects may be obtained.

At 210, tissue staining may be performed. For example, types of normal and cancer tissue samples that may be selected may include Formalin-fixed paraffin-embedded or tissue that was fresh-frozen in OCT compound and sectioned or tissue fixed with methanol or any other appropriate fixative. Centrosomes may be immunofluorescently stained 212 for γ-tubulin (red) and nuclei (with Hoechst) 214 in paraffin embedded sections of DCIS. For dual color staining 214, samples to be used may be stained with, for example, antibodies (or any binding agent) directed against any component of centrosomes or centrioles or the peri-centriolar matrix (PCM) or any protein that shows substantial localization to centrosomes at any or all stages of the cell cycle.

Examples of centrosomal proteins may include Cell division cycle protein 27 homolog (CDC27Hs), Centrosomal protein of 110 kDa (Cep110), Centriolin (110 kDa centrosomal protein), Tubulin gamma-1 chain (GCP-1), Separin, Centrosomal protein of 27 kDa (Cep27), Gamma-tubulin complex component 4 (GCP-4), Serine/threonine-protein phosphatase 4 catalytic subunit (PP4C), Spindle assembly abnormal protein 6 homolog (HsSAS-6), Nucleophosmin (NPM), Serine/threonine-protein kinase PLK1, Aurora C, Centrosomal protein of 290 kDa (Cep290), Ninein (hNinein), Centrin-1, Kinesin-like protein KIF15, Centrosomal protein of 63 kDa (Cep63), A-kinase anchor protein 9 (AKAP 450), Cytoskeleton-associated protein 5 (Colonic and hepatic tumor over-expressed protein: Ch-TOG protein), Breast cancer type 1 susceptibility protein (RING finger protein 53), Serine/threonine-protein kinase Nek2, pericentrin, centrin-2, cenexin.

For example, staining of centrosomes may be performed using antibodies directed against γ-tubulin and centrin may be used for some samples to do the verification.

Likewise, staining of nuclei may be performed using DAPI or any other nuclear stain, or any Ab or binding agent targeted against any nuclear component or nuclear membrane component. For example, Hoechst may be used as nuclear stain.

Optimized staining steps involving antigen retrieval and incubation time may be performed.

Confocal microscopy 218 imaging of clinical samples.

Types of microscopy/analytical method: laser scanning or spinning-disk confocal, electron microscopy, electron microscope tomography, IHC, 3D-SIM, X-ray microscopy or any other kind of microscopy/analysis that allows the volume of centrosomes in individual cells to be determined. For example, the LSM 700 confocal microscope may be used.

Images of tissue samples may be acquired with, for example, a Zeiss LSM 700 confocal microscope 218 (using 63× oil immersion lens with a numerical aperture of 1.4 220 at 1.5× optical zoom 222). All imaging parameters may be fixed across all samples. For optimal results, laser power may be adjusted to the minimum level wherein fluorophore emission was saturated. For detector saturation, the gain (master) may be adjusted such that the detector registers the target fluorophores in each channel within full range of detector settings 224 (8-bit, 12-bit, 16-bit) to prevent over- and under-saturation and maximize accuracy. The offset may be adjusted to minimize the background in the sample. Normal, DCIS and IBC areas premarked by a pathologist were imaged to obtain at least 10 regions of interest (ROIs) each containing 20-30 nuclei and associated centrosomes

226. For example, 10-15 fields of view within the stained tissue may be imaged via laser scanning confocal microscopy and for each field, 9-15 optical sections of 0.45 um thickness each are acquired.

At 228, image analysis and counting may be performed. At 230, background subtraction, surfacing, splitting, and volume rendering may be performed. At 232, iCTR and mCTR counting and volume determination may be performed.

Figure 42:
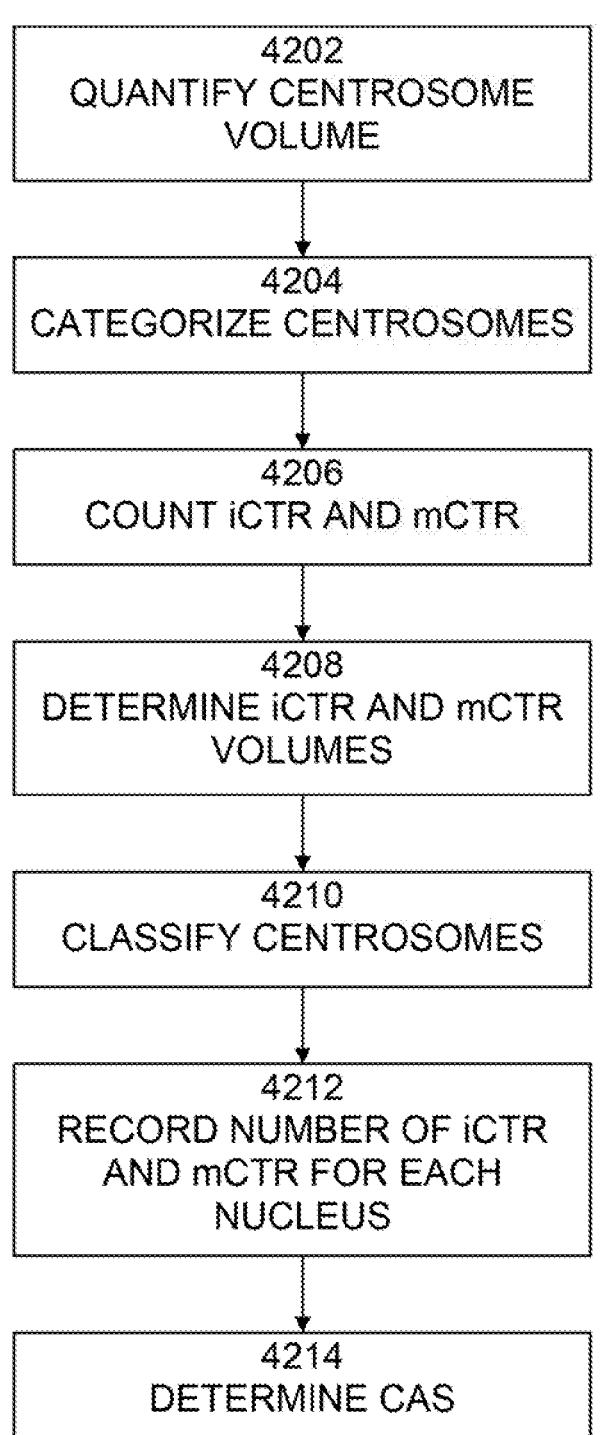
FIG. 42 is an exemplary flow diagram of a process of image analysis and counting in accordance with embodiments of the present techniques.

An example of image analysis and counting 228 is shown in more detail in FIG. 42. Image analysis and counting 228 begins with 4202, in which for each field of view, the raw image may be used to first quantify the volume of each centrosome to determine which are iCTRs and which are mCTRs and to allocate them to related nuclei. If there is any confusion or is not clear from the raw image, then Maximum intensity projection may be used to resolve the image. To do this, the optical sections are stacked to produce a "maximum intensity projection image" and a region of interest (ROI) is defined wherein there are several nuclei (at least 10) and centrosomes and each nucleus can be assigned to a centrosome or centrosome cluster. Any nucleus which is not visible completely is excluded (along with the centrosome(s) associated with it) from the ROI.

At 4204, the centrosomes may be categorized. Centrosomes may be categorized as individual centrosomes (iCTRs) if their numbers and boundaries can be clearly distinguished and their volumes lie within the range of volumes found in normal tissue, for example, (0.2-0.74 cubic microns for breast tissue stained to visualize gamma-tubulin distribution). Centrosomes may be categorized as megacentrosomes (mCTRs) if the volume of a centrosome is greater than the range of volumes found in normal tissue, for example 0.74 cubic micron for breast tissue stained to visualize gamma-tubulin distribution. Note that normal tissues usually have only 1 or 2 iCTRs associated with each nucleus, and no mCTRs.

At 4206, iCTR and mCTR counting may be performed. Within each region of interest, the number of iCTRs and/or mCTRs associated with each individual nucleus may be recorded as 1i, 2i, 3i, etc., for iCTRs and 1m, 2m, 3m, etc., for mCTRs. The total number of iCTRs and mCTRs within the ROI may be calculated.

At 4208, iCTR and mCTR volume determination may be performed. The raw confocal images are then opened in a suitable volume rendering software for determining the volumes of each iCTR and mCTR present in each ROI. For analysis, the IMARIS 8.2 3D volume analysis SOFTWARE may be used, for example. Any suitable volume rendering software may be used for this step. A low fluorescence intensity threshold value may be selected on the basis of smallest visible centrosome in normal samples (the same value is used in tumor samples too). The volume for all the centrosomes in the image may be obtained through this software. The volume range for a normal centrosome may be determined by analyzing the volumes of at least 1000 iCTRs from normal uninvolved breast tissue of, for example, 3 patients. The smallest and the largest value for centrosomal volume may provide the "normal centrosome volume range" for that tissue, for example (0.20-0.74 cubic microns for breast tissue stained to visualize gamma-tubulin). Since, normal samples do not have megacentrosomes, that aspect may be ignored.

For images of tumor samples, volumes of all iCTRs and mCTRs may be determined using the same (i) volume rendering software as for normal tissue, and (ii) fluorescence intensity threshold as for the corresponding normal tissue.

At 4210, using the "normal centrosome volume range" determined for normal samples, centrosomes in the cancer sample may be classified into iCTRs and mCTRs. At 4212, for each ROI in the cancer tissue, the number of iCTRs and mCTRs associated with each nucleus within the ROI may be recorded for analysis. At 4214, also shown as 234 of FIG. 2*b*, a cumulative Centrosome Amplification Score (CAS) may be determined for the cancer sample using, for example, the formula below:

For example, the CAS may have two components, CASi and CASm. CASi may be an aggregate value of both frequency and severity of numerical centrosome amplification, and may be scaled relative to the range found in normal somatic tissue. CASm, may be an aggregate value of both frequency and severity of structural centrosome amplification, and may be scaled relative to the volume range found in normal somatic tissue. Then CAStotal=CASi+CASm Quantitation of Numerical CA:

The numerical centrosome amplification component (i-component) may be determined according to:

$$CASi =$$

$$\text{Average}\left(\frac{N_i - R_{th}}{R}\right) * \frac{\text{percentage}(N_i > R_{th})}{\text{scaling factor } \beta_i} = \left(\frac{\sum_{i=1,N_i>2}^{N}(N_i-2)}{\sum_{i=1}^{N}I(N_i>2)} * \frac{1}{R}\right) * \frac{p_i}{\beta_i}$$

Where $p_i$ is the percentage of cells for which the number of individually-distinguishable centrosomes (iCTRs) exceeds the threshold value of 2. This ensures that only cells whose centrosomal copy number exceeds the upper limit of that seen in most normal somatic cells are included in the CAS analysis. $\beta_i$ is the scaling factor we used to ensure that both CASi and CASm are given equal weight in the formula for CAStotal. This value might change depending on the tissue type being evaluated, the centrosomal marker being used and the data itself. N is the total number of cells analyzed in the sample. The index i takes the values {1, 2, 3, . . . , N}, that is, from 1, 2 all the way up to N. $R_{th}$ is the highest number of centrosomes present in a normal breast cell, i.e., 2. $N_i$ is the number of iCTRs in a cell that contains more than 2 iCTRs. Thus, $(N_i–R_{th})$ indicates the number of excess centrosomes present in a cell with numerical CA. $N_i$ may be used to indicate taking the average over cells with numerical CA. R is the range of values for number of centrosomes present in a normal cell, which is 2 here.

Figure 11:
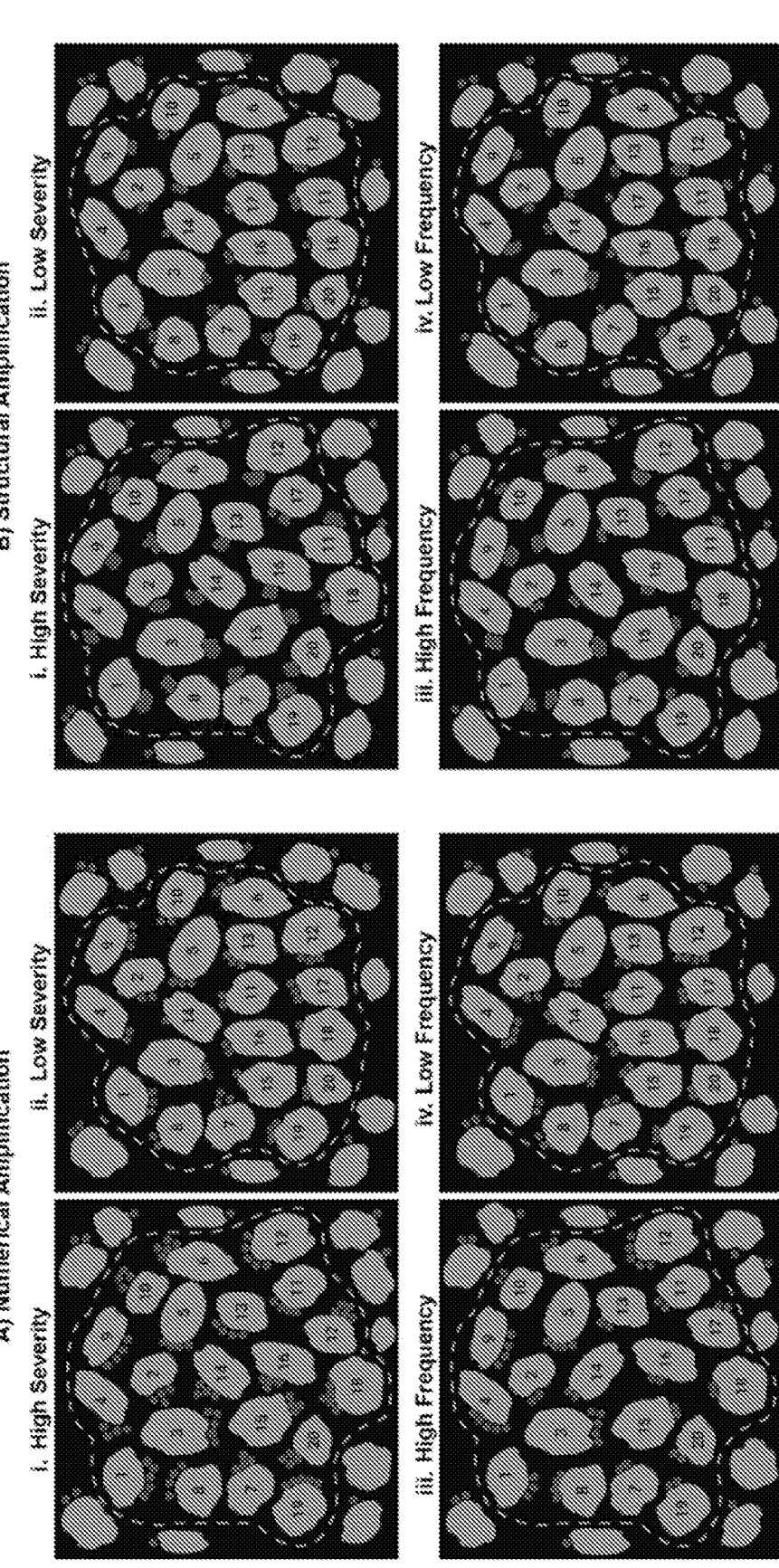
FIG. 11 is an exemplary schematic depicting the high and low severity and frequency of numerical centrosome amplification and structural centrosome amplification in accordance with embodiments of the present techniques.

The "severity" component of CASi, $$\text{Average}\left(\frac{N_i - R_{th}}{R}\right),$$

quantifies how "severe" the numerical CA is, that is, the extent to which the numerical CA exceeds the baseline value of 2 in cells that carry three or more iCTRs (i.e., Ni>2) (FIG. 11, Panels Ai and Aii). Therefore, cancer cells with 1 and 2 iCTRs do not contribute to this component. Since cells with larger numbers of iCTRs represent a more severe numerical CA, a linear measurement was implemented to provide a measure of the number of iCTRs (above the baseline value of 2) in a given cell by computing the score $(N_i–2)$ for each cell. Finally, an average of all these scores is determined. The "frequency" component of the CASi score $(p_i/\beta_i)$ provides the scaled frequency of numerical CA in the sample (FIG. 11, Panels Aiii and Aiv). For example, the value of CASi scaling factor $\beta_i$ used here is 0.1 for breast tissue. FIG. 11 is a schematic depicting the high and low severity and frequency of (Panel A) numerical centrosome amplification and (Panel B) structural centrosome amplification.

The lowest value for the severity term in CASi is one (assuming that all cells demonstrating numerical centrosome amplification have only 3 iCTRs); the maximum value for the severity term can potentially be a very high value, since the number of iCTRs per cell can be very high.

The lowest value of the "frequency" component of CASi is zero (no abnormal cells contribute to the frequency). The highest value (100% of cells are abnormal and contribute to the frequency) of the "frequency" component of CASi for breast tissue is 10.

Note that the values of the "severity" and "frequency" terms of individual tumor samples can be easily compared to each other. For instance, if the value of the severity term of CASi for sample A is twice that in sample B, can we conclude that the severity of numerical amplification in Sample A is twice that in sample B. Similarly, if tissue A and B have the same severity, but the frequency of cells carrying >2 iCTRs in B is half the corresponding frequency in sample A, the CASi of A will be double that of B. Moreover, the effects of both CASi components (severity and frequency of numerical amplification) are multiplicative, meaning that if tissue A had both double severity and frequency compared to a sample B, the CASi value of A will be 4 times larger than CASi value of B.

Although the severity and frequency terms of CASi may be multiplied to obtain the cumulative CASi value, the severity and frequency terms may be recorded separately too since they individually might also have value in risk prognostication in tumor samples.

Quantitation of Structural CA:

The structural centrosome amplification component (m-component) may be determined according to:

$$CASm = \text{Average}\left(\frac{V_{im} - V_{th}}{\sigma_{V_{im}}}\right) * \frac{\text{percentage}(V_{im} > V_{th})}{\text{scaling factor } \beta_m} =$$

$$\frac{\sum_{i=1}^{N}\sum_{m=1}^{N_i}(V_{im}-0.74)*I((V_{im}>0.74)}{\sigma_{V_{im}}} * \frac{p_m}{\beta_m}$$

Where $V_{im}$ is the volume of the $m_{th}$ megacentrosome in the $i_{th}$ nucleus. $p_m$ is the percentage of cells with mCTRs; where a megacentrosome is defined as a centrosome whose volume exceeds the $V_{th}$ critical for that tissue. $V_{th}$ critical for a given tissue is the maximum volume of a normal centrosome in that tissue which was 0.74 μm³ for breast tissue. $\beta_m$ is a scaling factor used to ensure that both CASi and CASm are given equal weight in the formula for CAStotal. For example, the value of $\beta_m$ used here is 0.148. $\sigma_{V_{im}}$ is the standard deviation of the volume of mCTRs.

For each mCTR (centrosome whose volume exceeds the upper limit of the normal centrosome volume range for that tissue), a z-score may computed based on the formula below, reflecting the extent to which the volume of that mCTR exceeds the maximal normal value (the value for $V_{im}–V_{th}$ critical is computed) relative to the baseline (achieved by dividing by the $\sigma_{V_{im}}$ the standard deviation):

$$z = \frac{V_{im} - V_{th}}{\sigma_{V_{im}}}$$

15

Next, this value may be multiplied by the number of mCTRs per nucleus. Finally, all these values are averaged to obtain the severity score for structural CA (FIG. 11, Panel Bi and Bii). The frequency component of CASm has essentially the same overall mathematical formula as the corresponding term in the CASi component (FIG. 11, Panel Biii and Biv). In the present form of the process, the components CASi and CASm, contribute equally to the CAStotal score and are thus given equal weight.

Once a CAS is obtained for a large cohort of breast cancer specimens, we can either:

Use linear discriminant analyses or pair classification to separate CAStotal, CASi and CASm values into, for example, "high-risk" and "low-risk" categories based on detailed statistical analyses of the correlations between CAStotal, CASi and CASm values and clinical outcomes [including progression-free survival (PFS)/overall survival (OS)/metastasis-free survival (MFS)]. For example, the log rank test may be used, but other survival tools may be used as well. For example, using the same cutpoint may achieve significance in discovery and validation.

Alternatively, CAS values may be stratified into discrete classes (for example, into low-, medium- and high-risk categories) and used as a dependent variable in a multiple-group logistic regression analysis where clinical outcomes (PFS/OS/MFS) will be used as an independent variable. In addition, the ROC curve (Receiver Operating Characteristic, non-parametric) may be used to evaluate the cut-off CAS-total, CASi and CASm values based upon PFS/OS/MFS. Finally, a percentage risk may be assigned to each CAS interval thereby establishing CAS as an independent measure of risk. Note that these results/cut-offs/categories may be different for different types of cancer. For example, such results/cut-offs/categories may be established this for pancreatic, prostate, head and neck and colorectal cancers.

Scoring of Centrosomes in Clinical Samples.

Raw 3D image data were processed using IMARIS Bitplane 8.2 3D volume rendering software to determine the volume of each centrosome within each ROI. "Volume rendering" refers to transforming a 2D image stack for 3D visualization and subsequent analysis. To exclude non-specific signals, a common background subtraction was applied to all images. This parameter was derived by first measuring the average diameter of ~100 centrosomes in 10 ROIs (FIGS. 1a and 1b), and then using the background corresponding to this average diameter as the background subtraction threshold. Finally, data from all optical sections were ordered to enable volume measurement for each centrosome. The final data of volumes of all centrosomes were then compared to a maximum intensity projection image and centrosomes for each cell were quantified based on proximity to their associated nuclei. The number and volume of all centrosomes associated with each nucleus in the tumor area were recorded.

Categorization of Centrosomes into iCTRs and mCTRs.

Centrosomes in breast tissue (normal, DCIS or IBC) were categorized into individually distinguishable centrosomes (iCTRs) and megacentrosomes (mCTRs). iCTRs were defined as centrosomes that stain positive for γ-tubulin; iCTR numbers and boundaries were clearly distinguishable, and their volumes lay within the range of centrosome volumes found in normal breast tissue stained for γ-tubulin. The volume range for a normal centrosome was determined by analyzing volumes of centrosomes from both adjacent uninvolved tissue from cancer patients and normal breast tissue from disease-free individuals (FIG. 10).

16

Figure 10:
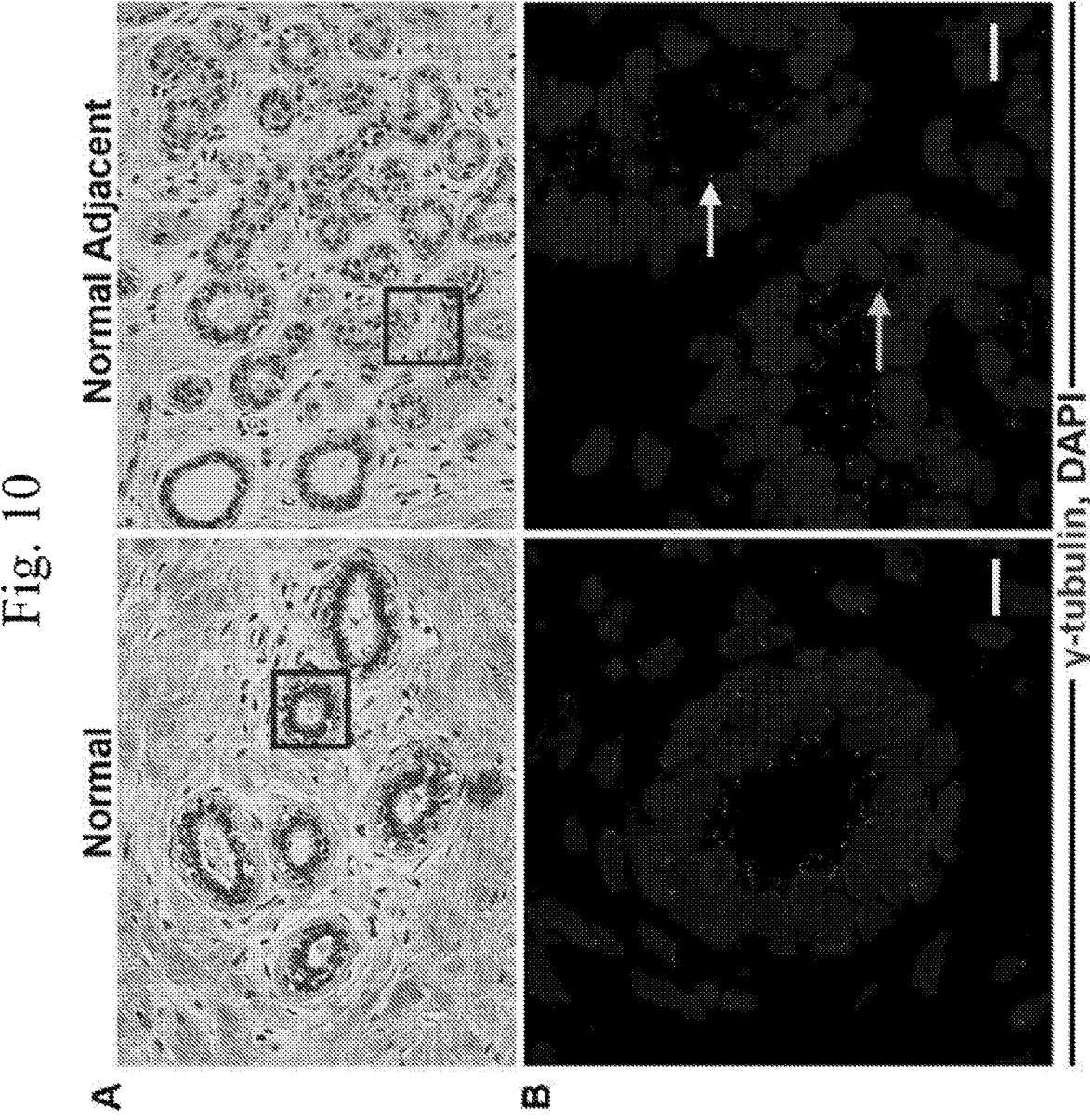
FIG. 10 is an exemplary illustration of representative immunographs of normal and normal adjacent breast tissue sections for centrosomes in accordance with embodiments of the present techniques.

FIG. 10 depicts representative immunographs of normal and normal adjacent breast tissue sections for centrosomes. Panel A depicts representative H&E images of the ducts of the normal and normal adjacent breast tissue sections. (Images were captured at 20× magnification). Panel B depicts confocal micrographs showing numerical and structural CA in normal adjacent breast tissue sections.

Determination of the Normal Volume of Centrosomes

To determine the normal volume range of centrosomes in breast tissue, measurement was made of the volume of 500 centrosomes from adjacent uninvolved tissues from BC patients and from normal breast tissue obtained from reduction mammoplasty (FIG. 10). For adjacent uninvolved tissues, the selected cohort (n=40 patients) had a median age of 53.5 years (age range: 38-69.5 years); 4 patients were grade 1, 17 were grade 2, and 19 were grade 3. Centrosomal volumes in these samples was evaluated as described in the analysis section. The mean centrosome volume for the adjacent uninvolved tissue sections was higher relative to the normal tissue from reduction mammoplasty. Thus, the smallest and largest values for individual centrosome volume from normal tissue was chosen as the "normal centrosome volume range" for breast tissue. The mean volume of centrosomes in normal breast epithelial cells ranged from, for example 0.20-0.74 $\mu m^3$, for breast tissue stained to visualize gamma-tubulin. Centrosomes with volumes greater than the range of volumes found in normal tissue, for example 0.74 $\mu m^3$ for breast tissue stained to visualize gamma-tubulin distribution, were categorized as mCTRs. All centrosomes in each ROI were thus categorized as iCTRs or mCTRs.

Algorithm-Based Analytics 234, Shown in FIG. 2b.

For each sample, a cumulative CAS (CAStotal) was computed based on the formula: CAStotal=CASi+CASm, where CASi and CASm are scores that describe numerical and structural CA phenotypes, respectively. Details on quantitation of numerical and structural CA are added in Supplementary data.

Statistical Analysis.

Figure 12:
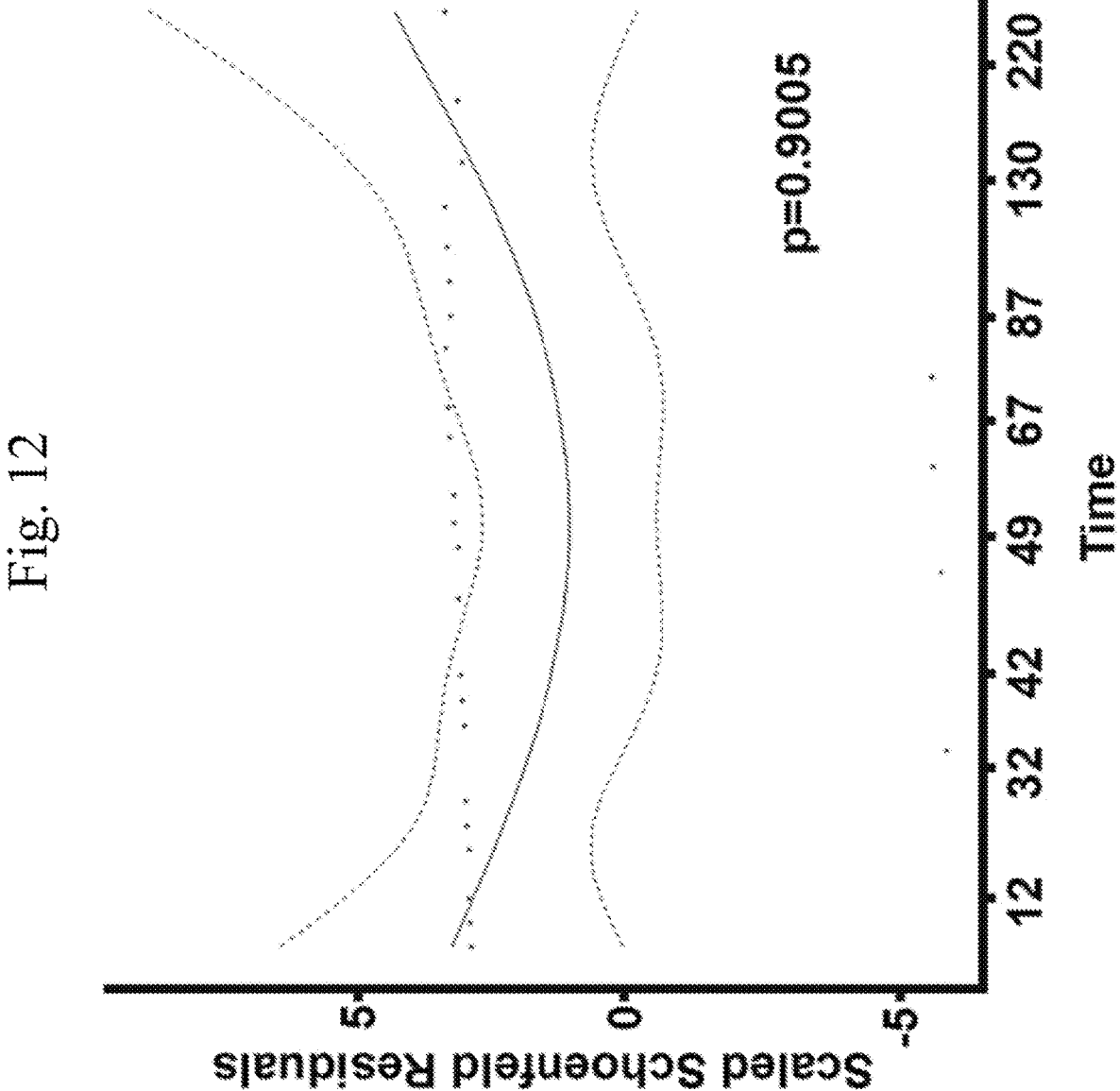
FIG. 12 is an exemplary illustration of graphical checks of the proportional hazards assumption in accordance with embodiments of the present techniques.

Statistical analysis was accomplished with SAS 9.4 software (Cary, NC, USA), and the R-project version 3.4.3 (R Foundation for Statistical Computing, Vienna, Austria, R-project.org/). Raw CA volume data were converted to CASi, CASm and CAStotal according to the algorithm. Scaling factors recommended were used to normalize score of CASi and CASm in the range 0-3. Chi-square tests were performed to check recurrence proportions in patient subgroups. The tests of group mean differences shown in Box Plots were based on nonparametric Wilcoxon Rank Sum Tests and Kruskal-Wallis tests depending on the number of groups used for comparison, where the y-axis reflects the ranks of observations. RFS was used as the endpoint for the survival analysis (restricted to 10 years). The optimal cutoff (threshold used to categorize patients into high- or low-risk of LR subgroups) of the CAStotal value was selected based on the results of 133 log-rank tests. We simply set each possible CAStotal value from 133 cases in the DC as cutoff and then constructed Kaplan-Meier survival estimators for cases classified into high-risk and low-risk groups. For example, the value 1.436 was finalized since it minimized the log-rank p-value. The same CAStotal cutoff was then used for the 119 cases from the VC to validate the model's effectiveness. Both univariate and multivariable Cox proportional hazard models, with age, grade, comedo necrosis, and RT controlled, were built to estimate Hazard Ratios (HRs) and 95% confidence intervals (CIs) between high vs. low CAStotal groups. A non-zero slope was detected in a generalized linear regression of the scaled Schoenfeld residuals on functions of time, which satisfied of the proportional hazards assumption (FIG. 12). A 2×2 confusion matrix and performance metrics was used for sensitivity analysis. The fitted Cox models were also used to predict the approximate 10-year recurrence rate using SAS PROC PHREG module. For all tests p<0.05 was considered to be statistically significant. FIG. 12 shows graphical checks of the proportional hazards assumption: Scaled Schoenfeld residuals against time plotted for CAStotal in the proportional hazards Cox model.

CAS Showed a Significantly Better Predictive Performance.

Figure 43A:
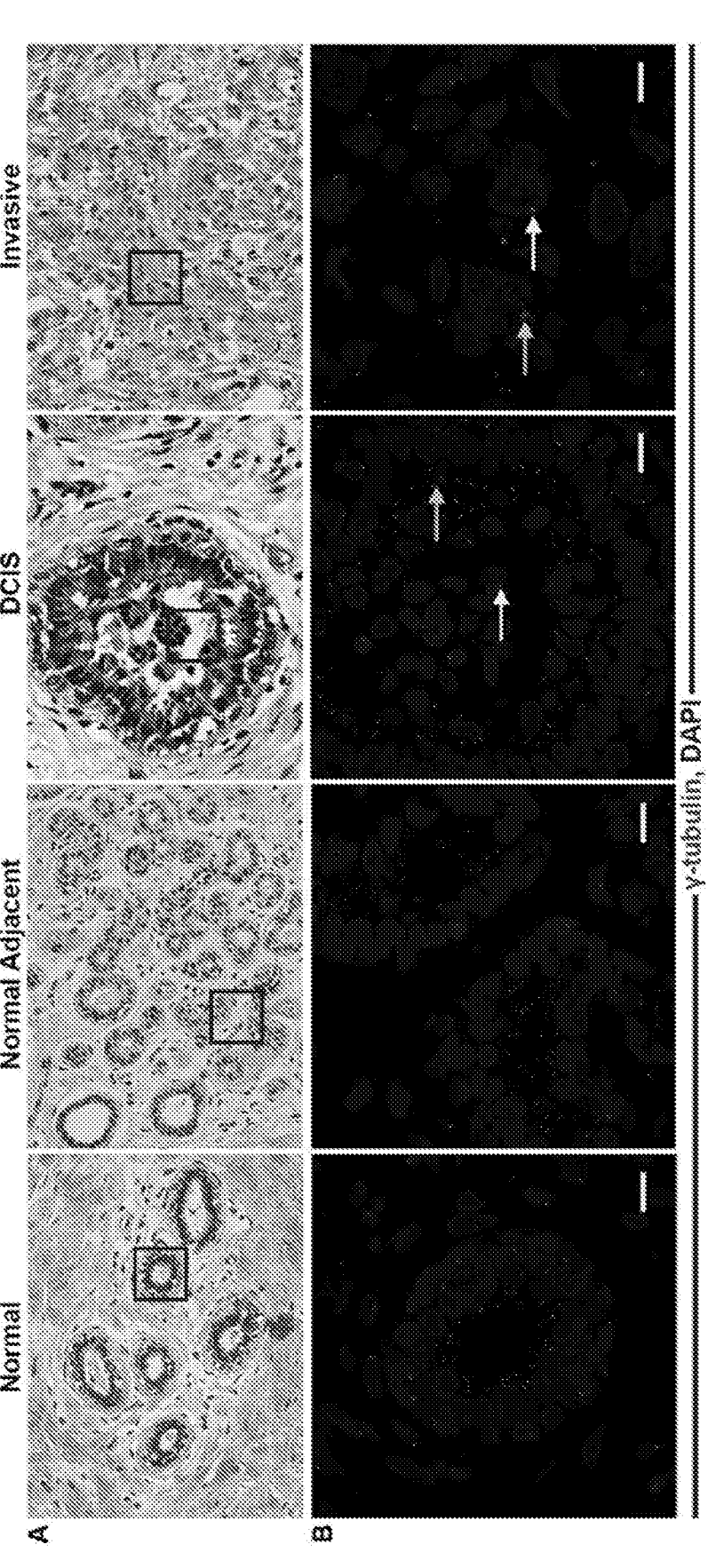

Utilizing CAS, the centrosome aberrations in a cohort of samples including samples from all the stages of BC were analyzed (FIGS. 43a and 43b). Normal epithelial tissue of breast from patients (n=54) who underwent mastectomy; normal adjacent epithelial tissue samples obtained from the tumor blocks with wide margins (n=94); ductal carcinoma in situ (DCIS) cohort from the discovery set (n=133); and invasive tumor lesions from the mixed DCIS cohort (n=64) were stained for CAS estimation. Interestingly, we observed that the Wilcoxon ranked CAS score increased significantly with disease progression, with normal samples exhibiting the lowest CAS values followed by the adjacent normal and DCIS, and finally the highest in invasive lesions. These findings clearly indicate that CA may have a critical role in tumor progression.

Furthermore, we quantified CAS in DCIS tissues and observed that higher CAS was associated with greater risk of recurrence and poor recurrence-free survival (RFS) after adjusting for other confounding factors. In addition, CAS showed a significantly better predictive performance than the Van Nuys Prognostic Index (VNPI) in terms of stratifying patients into the recurrence and recurrence-free groups. These exciting results strongly support the use of CAS as a prognostic biomarker and classifier, and its ability to identify the high-risk patients for personalized therapies.

FIG. 43a, Panel A shows representative H&E images of the normal (54), normal adjacent (n=94), pure DCIS (133) and invasive (n=64) breast tissue sections (20× magnification). FIG. 43a, Panel B) shows confocal micrographs showing numerical and structural CA. DCIS tissue sections are immunostained for centrosomes (γ-tubulin, red) and counterstained with DAPI (blue). Scale bar (white)—20 μm. FIG. 43a, Panels C, D, and E show representative Beeswarm Box plots for the CASi, CASm and CAStotal in all four groups.

Results: Traditional clinicopathological variables have limited capacity to predict recurrence for DCIS patients.

We found that among the 133 patients in the DC (shown in FIGS. 3a and 3b), 28 patients developed ipsilateral LR. The median age at diagnosis was 58 years (age range: 41-84), and median follow-up was 132 months (range: 14-333 months). Out of 133 patients, ~42% (n=55) received RT. Higher nuclear grade, the presence of comedo necrosis and the use of RT were clinicopathological parameters that showed proportional differences between recurring and LR-free patient subgroups (FIG. 3a). FIGS. 3a and 3b show descriptive statistics of clinicopathological characteristics for pure DCIS based on the recurrence status. FIG. 3a shows such characteristics in the DC and FIG. 3b shows such characteristics in the VC. The $\chi^2$p-values were used to determine if the differences in proportions were statistically significant.

However, only high grade and comedo necrosis showed associations with RFS in a univariable Cox regression analysis (FIG. 4a). Intriguingly, none of these clinicopathological variables showed any significant association with RFS in multivariate analyses (FIG. 4a), thereby indicating the limited capacity of traditional clinicopathological variables to predict LR for DCIS in our DC. FIGS. 4a and 4b show univariate and multivariate Cox proportional regression analysis for the risk of LR in DCIS treated with BCS or mastectomy comparing the influence of common clinicopathological variables relative to CAStotal. FIG. 4a shows such data in the DC and FIG. 4b shows such data in the VC.

Figure 13:
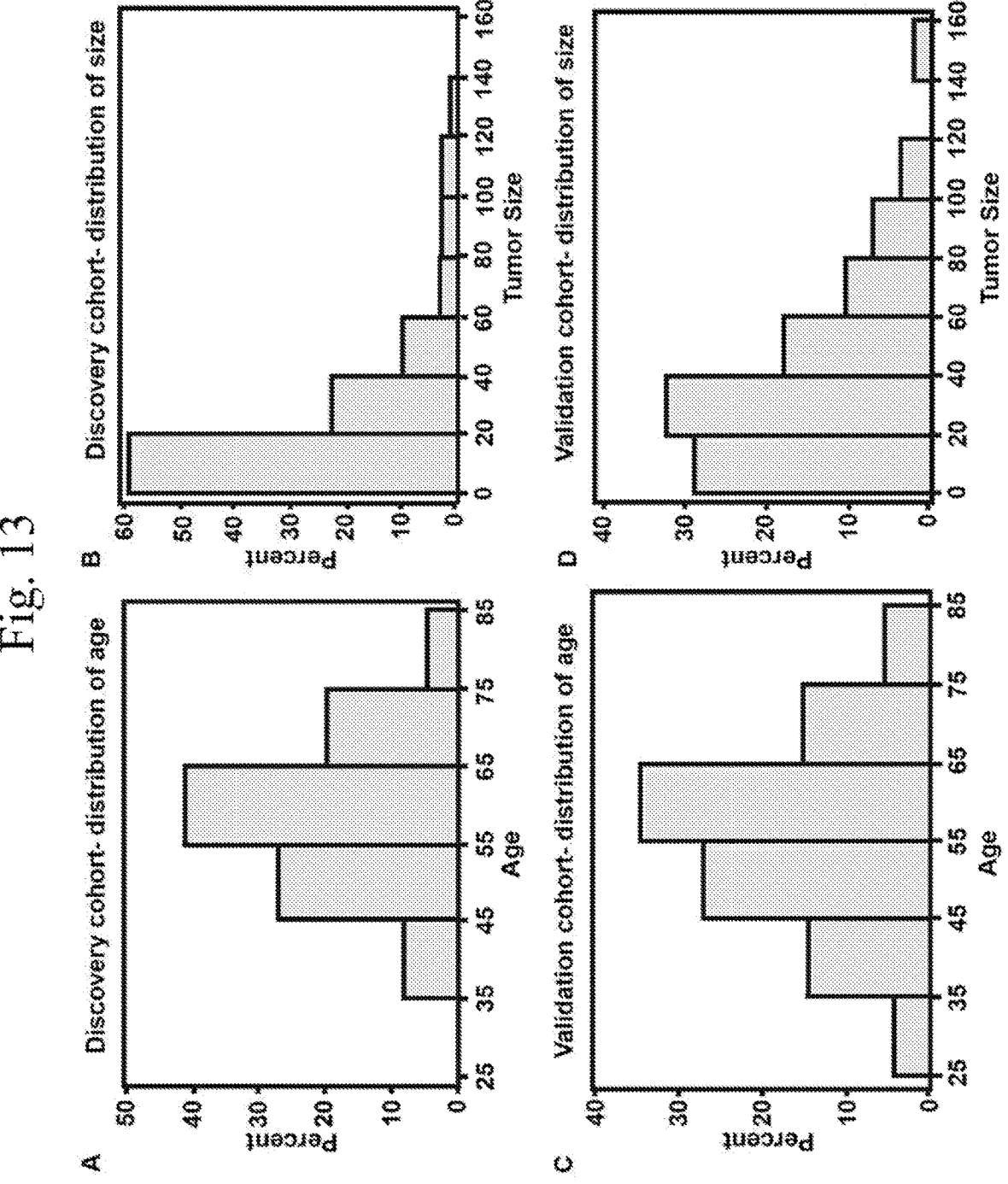
FIG. 13 is an exemplary illustration showing histograms representing the distribution of (Panel A) age in DC, (Panel B) tumor size in DC, (Panel C) age in VC, and (Panel D) tumor size in VC, in accordance with embodiments of the present techniques.
Figure 14:
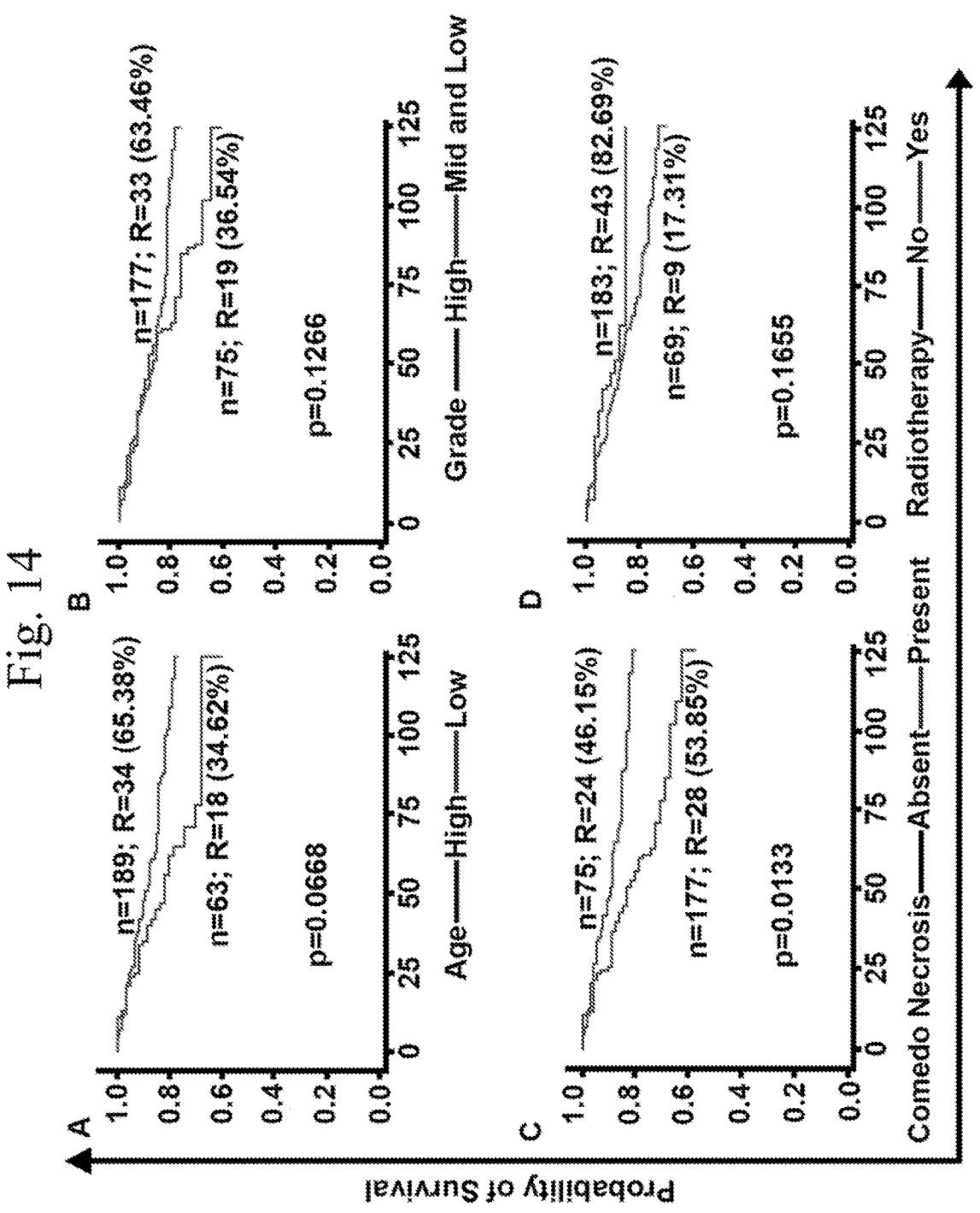
FIG. 14 is an exemplary illustration showing Kaplan Meier survival curves representing the RFS of patients in the DC and VC combined cohort (n=252) stratified into high and low groups based on (A) age, (B) grade, (C) comedo necrosis, and (D) radiotherapy. n: total number of patients in each group; R: number of patients who developed LR; % represents the percentage/proportion of the patients with LR of the total number of patients with LR in both groups combined.

Our VC was also from Nottingham University Hospital, UK (patient characteristics in FIG. 3b) and comprised of 119 DCIS patients out of which 24 patients presented with ipsilateral LR. Median age of these patients was 56 years, and the median follow-up was 121 months. Histograms representing distribution of age and tumor size are added in the supplementary data (FIG. 13). In addition we performed the KM survival analysis to show the effect of standard prognostic markers like age, tumor size, radiotherapy and comedo necrosis on recurrence for the whole dataset (DC and VC, n=252) (FIG. 14). Out of 119 patients, ~12% (n=14) received RT. In the VC, tumor size, presence of the comedo necrosis, and age, showed significant proportional differences between the LR and LR-free subgroups. FIG. 13 shows histograms representing the distribution of (Panel A) age in DC, (Panel B) tumor size in DC, (Panel C) age in VC, and (Panel D) tumor size in VC.

FIG. 14 shows higher CAS is associated with poorer RFS in both DC and VC. Kaplan Meier survival curves representing the RFS of patients in the DC stratified into CAStotal high and low groups in Panel A the DC where recurrence occurred as DCIS. Panel B shows the DC where recurrence occurred as invasive BC, Panel C shows the VC where recurrence occurred as DCIS, and Panel D shows the VC where recurrence occurred as invasive BC. In FIG. 14, n is the total number of patients in each group; R is the number of patients who developed LR; % represents the percentage/proportion of the patients with LR of the total number of patients with LR in both groups combined.

Recurrent DCIS Patients Show Higher CAS Compared to Non-Recurrent DCIS Ones

Figure 5A:
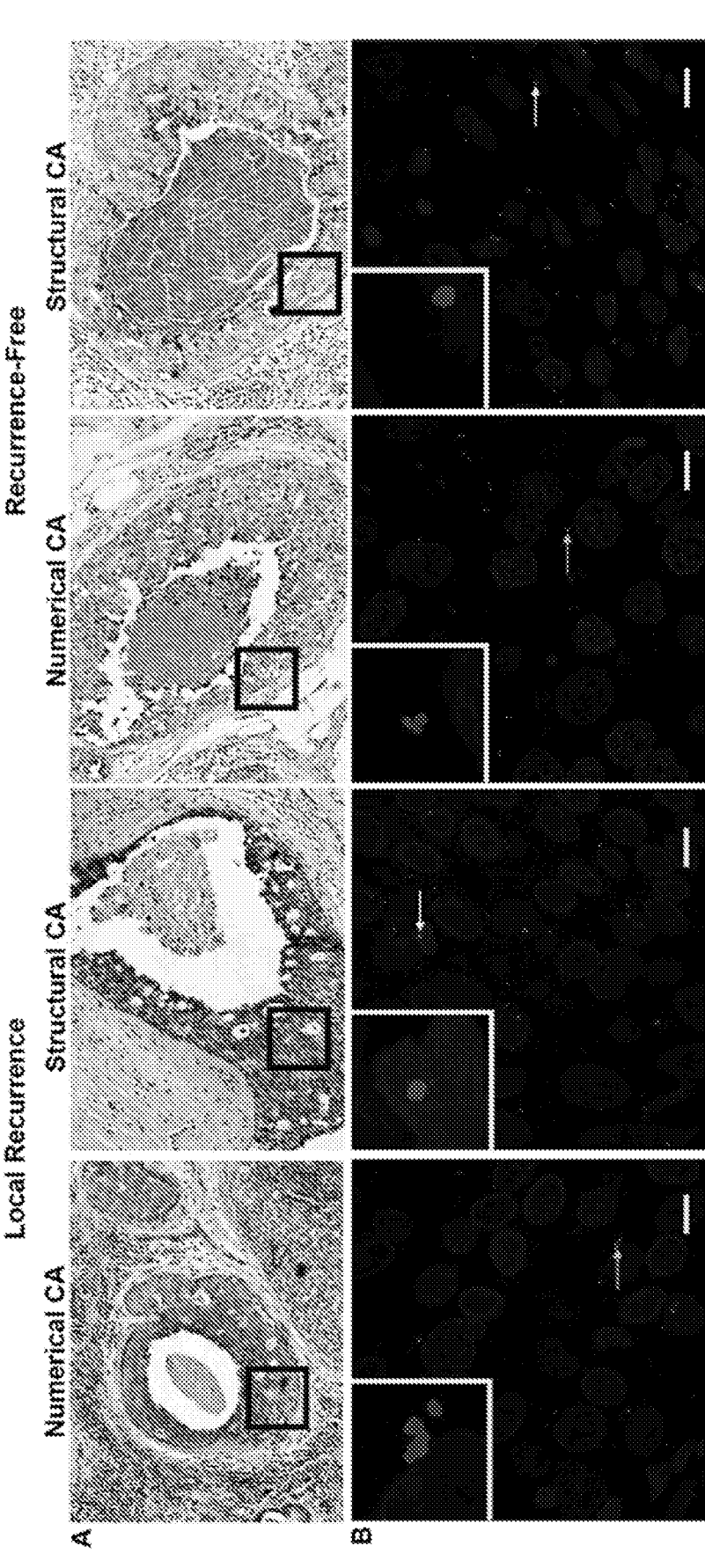
Figure 5B:
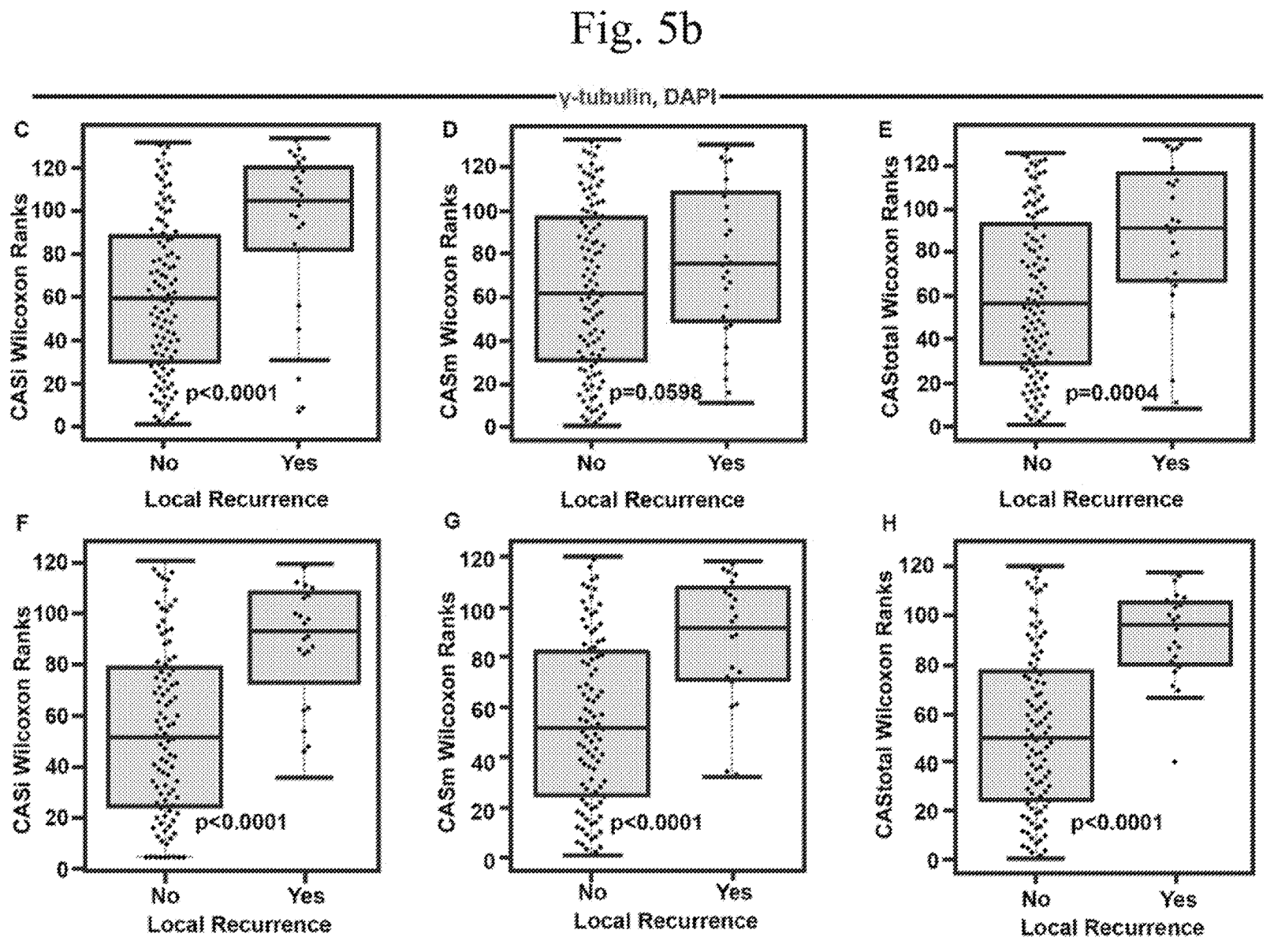

Centrosome numbers and volumes, evaluated and scored for numerical (CASi) and structural (CASm) centrosomal aberrations (as described in methods) were integrated using our algorithm to generate a composite CAStotal value for each sample of the DC (FIG. 5a, Panels A and B). FIGS. 5a and 5b show DCIS cases in the DC with ipsilateral recurrence exhibit higher CAS than recurrence-free cases. FIG. 5a, Panel A shows representative H&E images (20× magnification) of the ducts from DCIS cases with and without LR. Black boxes represent the area magnified in panel B. Panel B shows Confocal micrographs showing numerical (green arrows) and structural (yellow arrows) CA in DCIS with or without recurrence. Tissue sections were immunostained for centrosomes (γ-tubulin, red) and nuclei (Hoechst, blue). Scale bar (white), 20 μm. Beeswarm box plots showing Wilcoxon ranks for pure DCIS cases with LR (n=28) and without LR (n=105). FIG. 5b, Panel C shows CASi, Panel D shows CASm, Panel E shows CAStotal. p<0.05 was considered statistically significant. Beeswarm box plots showing Wilcoxon ranks for pure DCIS cases with LR (n=24) and LR-free cases (n=95) in VC (Panel F) CASi, (Panel G) CASm, and (Panel H) CAStotal. p<0.05 was considered statistically significant.

Interestingly, DCIS patients that developed LR within 10 years showed significantly higher CASi relative to LR-free patients (p=<0.0001; FIG. 5b, Panel C). These patients with LR showed greater severity (CASi severity) (p=0.25; FIG.

Figure 15:
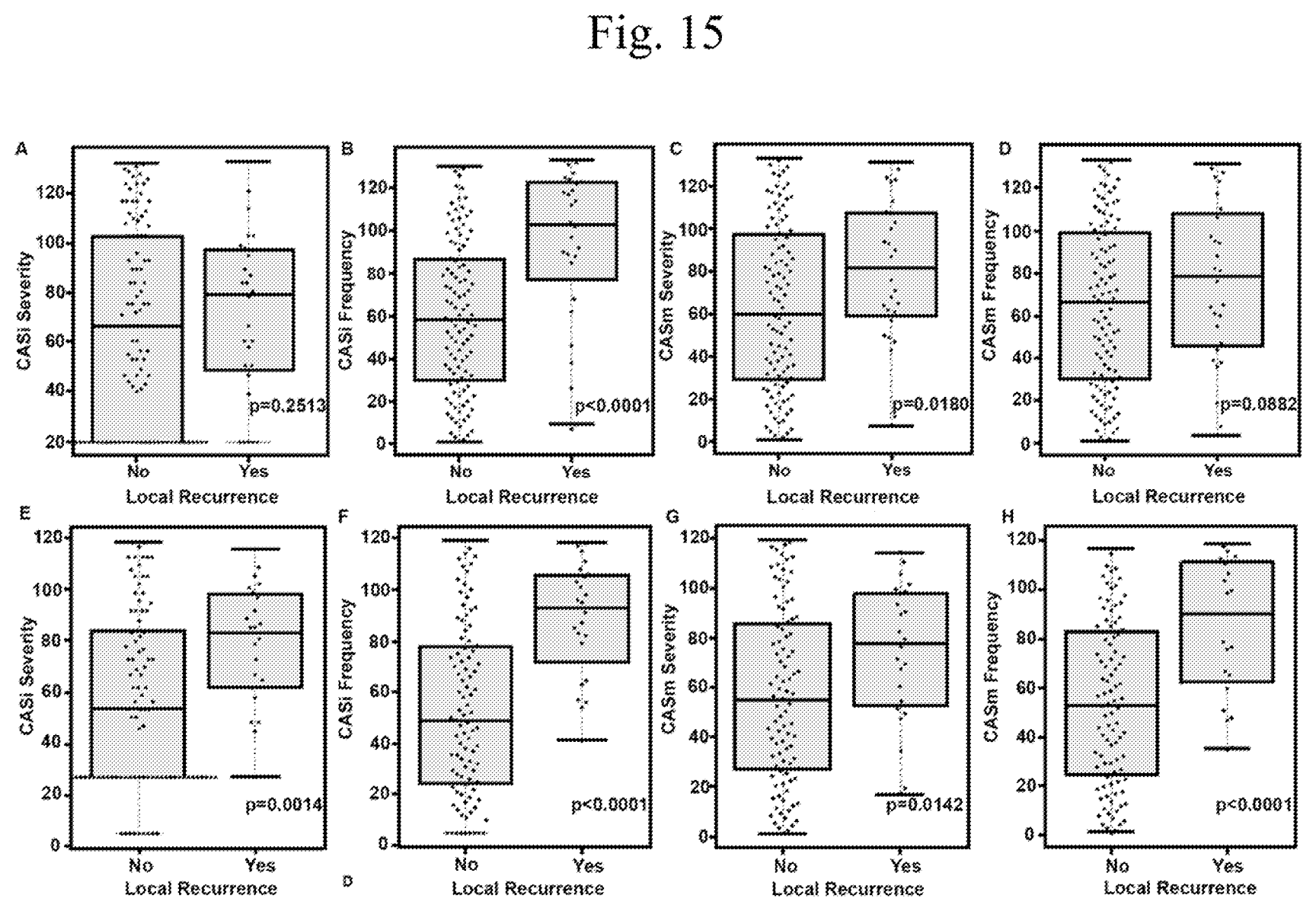

15, Panel A) and higher frequency (CASi frequency) (p<0.0001; FIG. 15, Panel B) of numerical CA compared to LR-free patients. Analysis of structural CA revealed that CASm was significantly higher (p=0.04, FIG. 5b, Panel D) for the LR subgroup relative to LR-free subgroup. DCIS with LR exhibited greater severity (CASm severity) (p=0.01, FIG. 15, Panel C) and frequency (CASm frequency) (p=0.08, FIG. 15, Panel D) of structural CA compared to LR-free DCIS. Cumulatively, a summation of CASi and CASm generated CAStotal, which was significantly higher for DCIS patients with LR relative to LR-free patients regardless of grade (mean scores in FIG. 16) (FIG. 5b, Panel E). FIG. 16 shows means scores and p-values of CASi, CASm and CAStotal in recurring and recurrence-free cases in DC.

Figure 17:
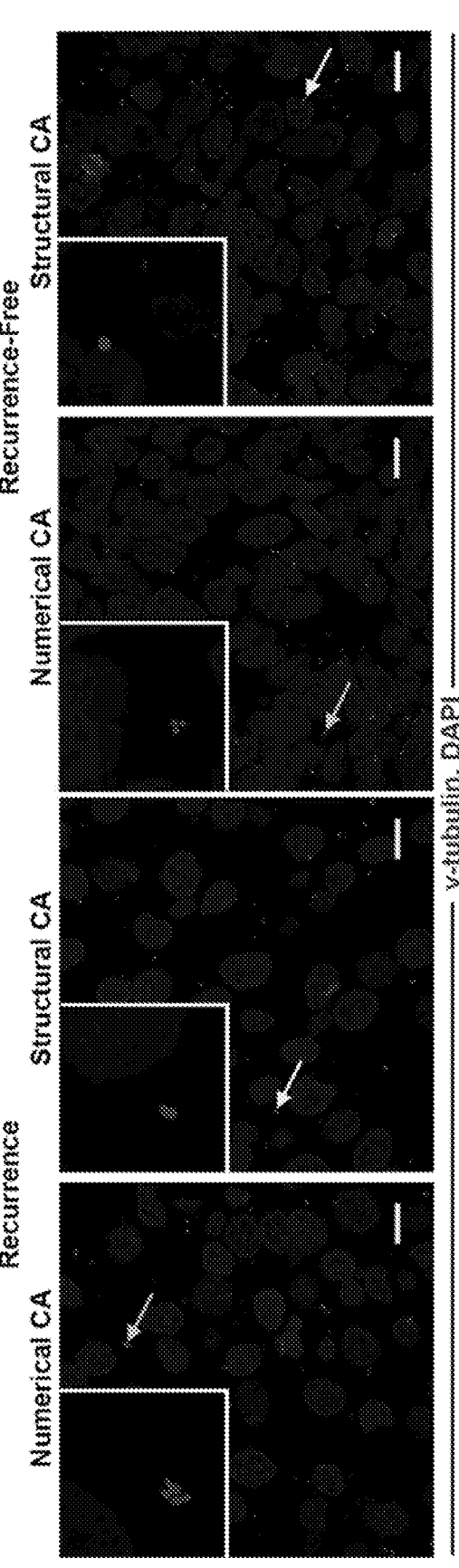
FIG. 17 shows representative confocal micrographs of DCIS tissue sections in the VC immunolabeled for γ-tubulin and Hoechst in recurrence and recurrence free samples in accordance with embodiments of the present techniques.

Employing the same methodology for the VC, we calculated CAS (FIG. 17) and found that irrespective of grade, DCIS cases with LR exhibited higher CAStotal relative to LR-free patients (p<0.0001) (FIG. 5b, Panel F). FIG. 17 shows representative confocal micrographs of DCIS tissue sections from VC immunolabeled for γ-tubulin (red) and Hoechst (blue) in recurrence and recurrence free samples.

Further, similar trends were seen for other CAS subcomponents as observed in the DC; the ranked mean values of CASi (p<0.0001) (FIG. 5b, Panel G) and CASm (p<0.0001) (FIG. 2H), including their severity (CASi severity p=0.0014; CASm severity p=0.014) and frequency (CASi frequency p<0.0001, CASm frequency p<0.0001) components, were higher in the patient subgroup with LR than in the LR-free subgroup (FIG. 15, Panels E, F, G, H).

FIG. 15 shows DCIS cases in the DC with LR exhibit higher frequency and severity of both numerical and structural CA: Beeswarm box plots showing Wilcoxon ranks for different CASs in pure DCIS cases with, LR(n=28) and without LR (n=105) in DC (Panel A) CASi severity, (Panel B) CASi frequency, Panel C) CASm severity, (Panel D) CASm frequency. Beeswarm box plots showing Wilcoxon ranks for different CASs in pure DCIS cases with LR (n=24) and without LR (n=95) in VC (Panel E) CASi severity, (Panel F) CASi frequency, (Panel G) CASm severity, (Panel H) CASm frequency. p<0.05 was considered significant. p<0.05 was considered significant.

Figure 18:
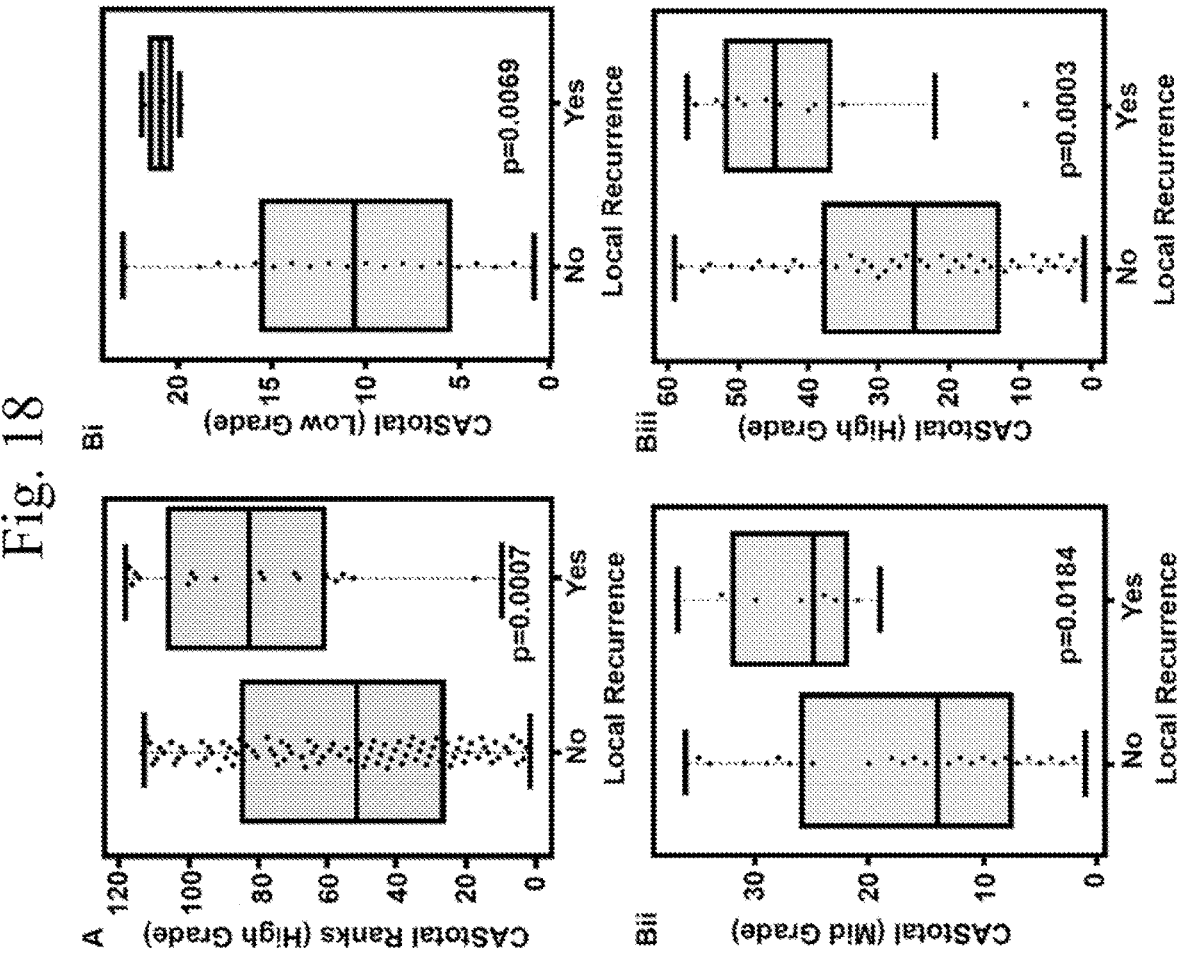
FIG. 18 is an exemplary illustration showing grade matched cases with LR exhibit higher CAS than grade-matched cases without LR in accordance with embodiments of the present techniques.
Figure 19:
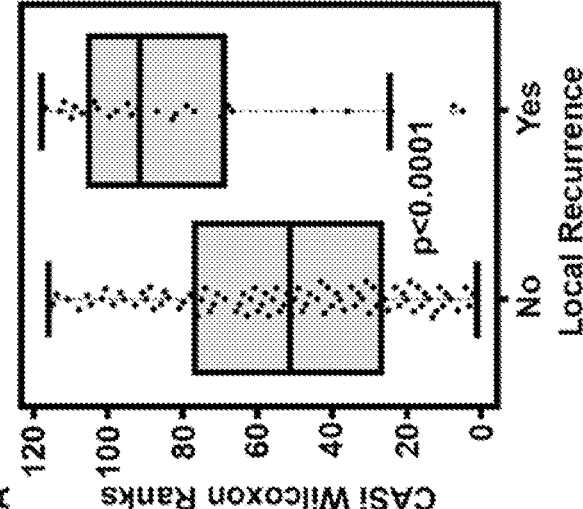
FIG. 19 is an exemplary illustration showing recurrent DCIS cases treated with BCS in the DC exhibit higher CAS than recurrence-free cases in accordance with embodiments of the present techniques.

Similar findings were evident for grade-matched patients in DC and VC (FIG. 18) and patients that were treated only with BCS (FIG. 19). FIG. 18 shows high-grade DCIS (n=118) cases with LR exhibit higher CAS than grade-matched cases without LR: (Panel A) Beeswarm box plots showing CAStotal Wilcoxon ranks for high-grade DCIS with LR (n=21) and without LR (n=97) in DC. (Panel Bi) Beeswarm box plots showing CAStotal Wilcoxon ranks for low-grade pure DCIS (n=23) cases with LR (n=3) and without LR (n=20) in VC. (Panel Bii) Beeswarm box plots showing CAStotal Wilcoxon ranks for intermediate-grade pure DCIS (n=37) cases with LR (n=9) and without LR (n=28) in VC, and (Panel Biii) Beeswarm box plots showing CAStotal Wilcoxon ranks for high-grade pure DCIS (n=59) cases with LR (n=12) and without LR (n=47) in VC. p<0.05 was considered statistically significant. FIG. 19 shows recurrent DCIS cases treated with BCS in the DC exhibit higher CAS than recurrence-free cases: Beeswarm plots showing Wilcoxon ranks for pure DCIS cases with LR (n=27) and without LR (n=91) (Panel A) CASi, (Panel B) CASm, and (Panel C) CAStotal. p<0.05 was considered statistically significant.

Figure 20:
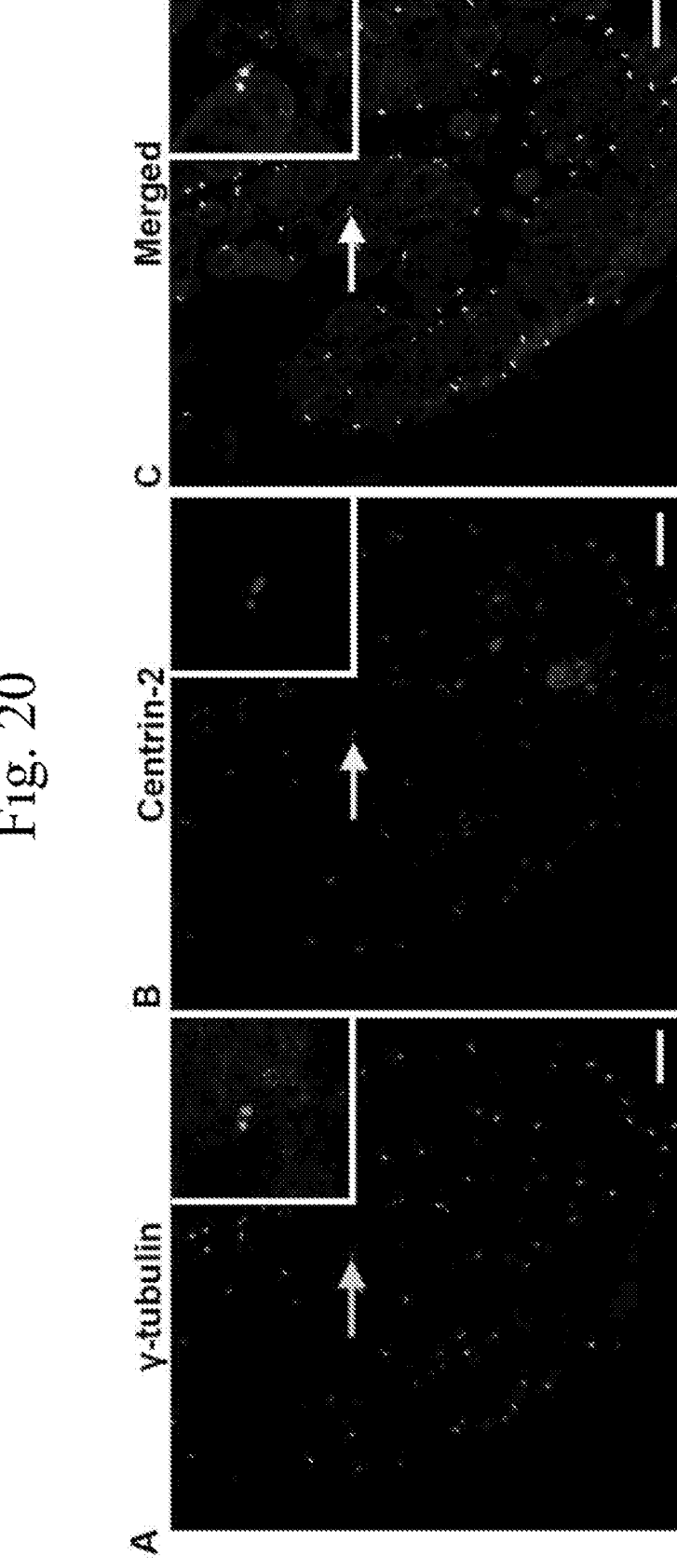
FIG. 20 shows representative confocal micrographs of DCIS tissue sections immunolabeled for centrin-2, γ-tubulin and Hoechst, in accordance with embodiments of the present techniques.

Collectively, our data strongly suggest a stark difference in centrosomal aberrations between DCIS tumors of patients with and without LR. Next, we co-immunolabeled 15 high-grade DCIS samples for both centrosomes (using anti γ-tubulin antibody) and centrioles (using anti-centrin-2 antibody) and generated CAStotal as described before. In all samples, γ-tubulin foci invariably overlapped with centrin-2 foci, confirming that both structurally and numerically amplified centrosomes are bona fide centrosomes and not simply aggregates of pericentriolar material. We also observed that none of the mCTRs had >2 centrin-2 foci, suggesting that enlarged γ-tubulin foci represent structurally augmented centrosomes and not supernumerary centrosomes that are tightly clustered to be indistinguishable (FIG. 20). FIG. 20 shows representative confocal micrographs of DCIS tissue sections immunolabeled for centrin-2 (red), γ-tubulin (green) and Hoechst (blue) in split form.

CAS stratifies DCIS patients into subgroups with high- and low-risk of LR within 10 years of diagnosis.

Figure 6:
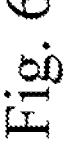
FIG. 6 is an exemplary illustration showing that in the DC and VC, higher CAS is associated with poorer RFS in accordance with embodiments of the present techniques.
Figure 22:
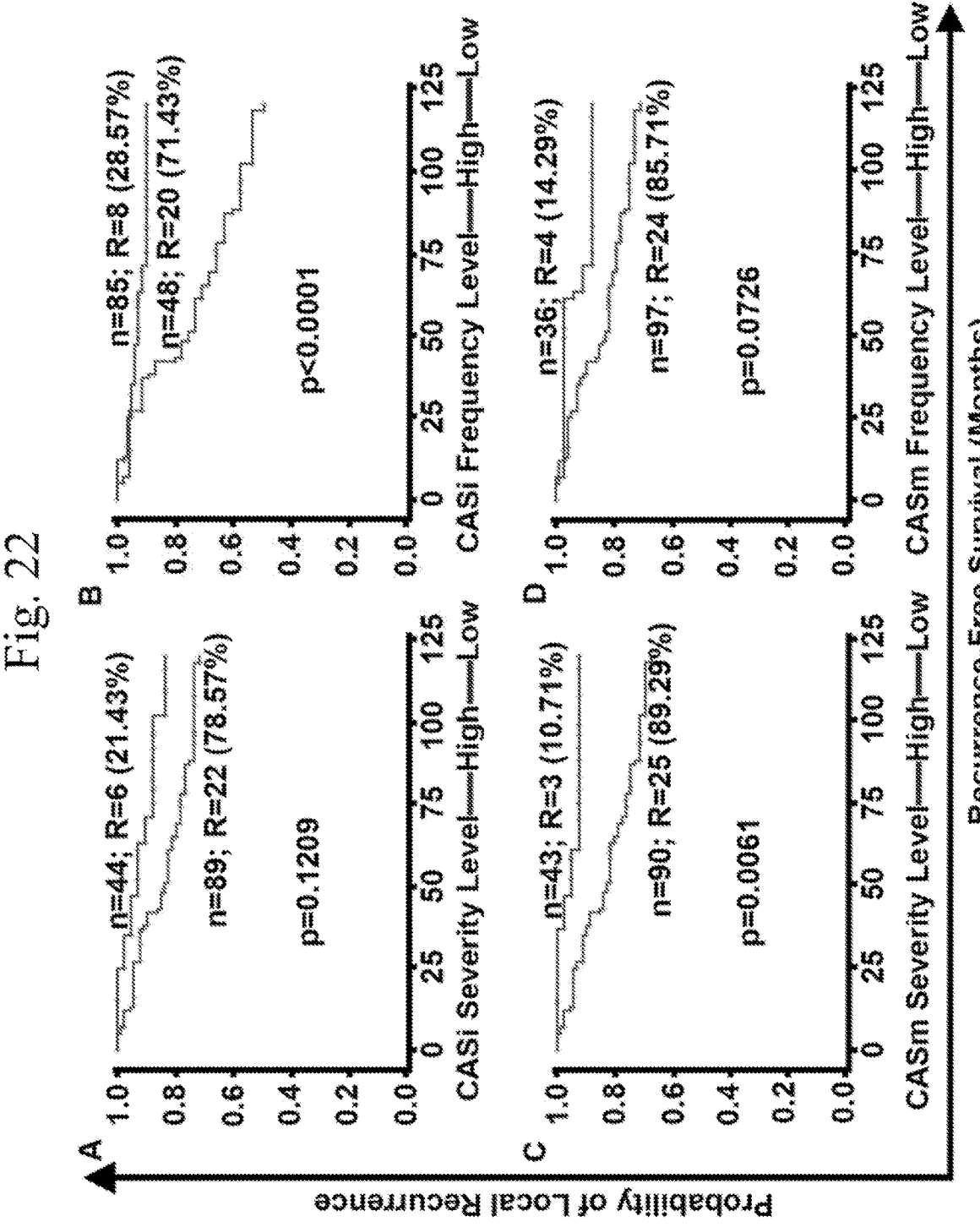
FIG. 22 is an exemplary illustration showing higher severity and frequency of numerical and structural CA are associated with poor RFS in the DC of DCIS cases in accordance with embodiments of the present techniques.

Upon stratification of all DC patients into low- and high-CAS groups (the threshold used was the one that minimized log-rank p-value) (FIG. 6), we found that DCIS patients with high CASi were associated with poorer RFS (p<0.001, HR=4.80) relative to those with low CASi (FIG. 6, Panel A, FIG. 22, Panels A, B, and FIG. 21). FIG. 6 shows that in the DC and VC, higher CAS is associated with poorer RFS. Kaplan Meier survival curves representing the RFS of patients in the DC stratified into (Panel A) CASi high and low groups, (Panel B) CASm high and low groups, (Panel C) CAStotal high and low groups. Kaplan Meier curves representing the RFS of DCIS patients in the VC stratified into (Panel D) CASi high and low groups, (Panel E) CASm high and low groups, and (Panel F) CAStotal high and low groups. N: total number of patients in each group; R: number of patients who developed LR; % represents the percentage/proportion of patients with LR out of the total number of patients with LR in both groups combined. FIG. 21 shows the Hazard Ratio and p value for the severity and frequency of CASi and CASm in DC. FIG. 22 shows higher severity and frequency of numerical and structural CA are associated with poor RFS in the DC of DCIS cases: Kaplan-Meier survival curves representing the RFS of patients in: (Panel A) high and low groups based on the severity component of numerical CA, (Panel B) high and low groups based on the frequency component of numerical CA, (Panel C) high and low groups based on the severity component of structural CA, (Panel D) high and low groups based on the frequency component of structural CA. N: total number of patients in each group; R: number of patients who showed LR. %: percentage/proportion of patients with LR out of the total number of patients with LR in both groups combined.

Similarly, high CASm was associated with poorer RFS (p=0.04, HR=2.396) compared to low CASm (FIG. 6, Panel B, FIG. 22, Panels C and D, and FIG. 21). CAStotal stratified the high-risk and low-risk DCIS patients with high significance and hazard ratio (p<0.001, HR=6.3) (FIG. 6, Panel C). We found that 85.7% of patients with LR were in the high CAStotal group. This association with CAStotal remained significant (p<0.001, HR=7.4) even after accounting for potential confounders, including comedo necrosis, tumor grade, age, RT, and receptor status (FIG. 4a). Although presence of comedo necrosis and CAStotal were associated with RFS in univariate analyses, only CAStotal remained significantly associated with RFS in multivariable analyses (FIG. 4a). Furthermore, when similar cox regression univariate and multivariate analysis was performed for CASi and CASm separately CASi and CASm was the strongest and most significant independent predictor of RFS respectively (FIG. 24 and FIG. 25). FIG. 24 shows univariate Cox proportional regression analysis for the risk of LR in DCIS treated with BCS or mastectomy comparing the influence of common clinicopathological variables relative to CASi and CASm in DC and VC. FIG. 25 shows multivariate Cox proportional regression analysis for the risk of LR in DCIS treated with BCS or mastectomy comparing the influence of common clinicopathological variables relative to CASi and CASm in DC and VC.

Figure 23:
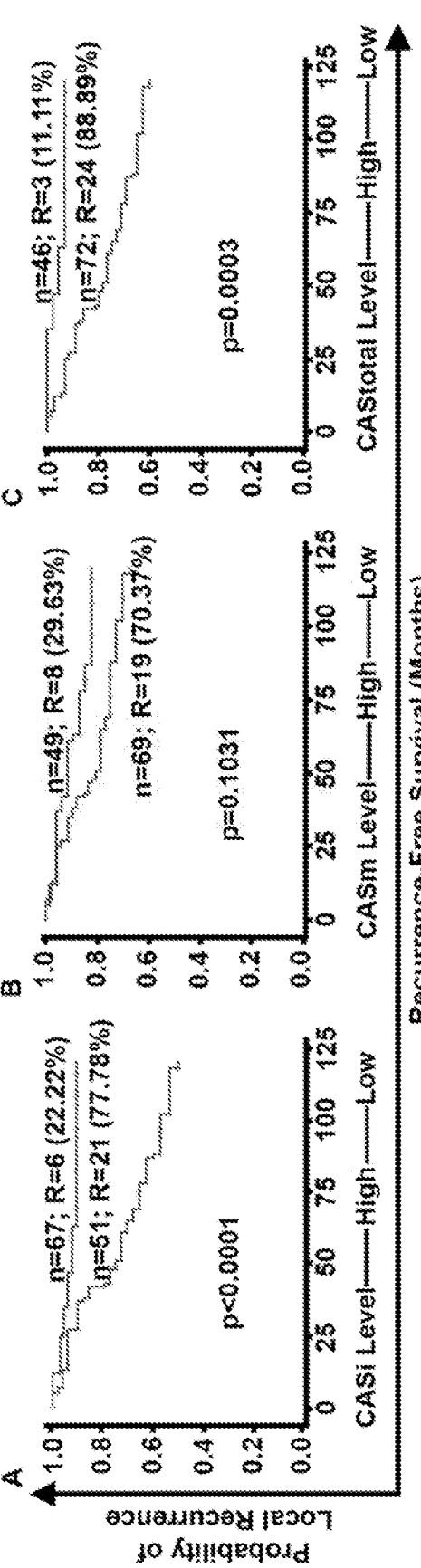
FIG. 23 is an exemplary illustration showing higher CAS is associated with poorer RFS for DCIS patients treated with BCS in the DC in accordance with embodiments of the present techniques.

Similar results were evident for the cases that were treated only with lumpectomy (FIG. 23). FIG. 23 shows higher CAS is associated with poorer RFS for DCIS patients treated with BCS in the DC: Kaplan Meier survival curves representing the RFS of patients in the DC stratified into: (Panel A) CASi high and low groups, (Panel B) CASm high and low groups, (Panel C) CAStotal high and low groups. N: total number of patients in each group; R: number of patients who developed LR; % represents the percentage/proportion of patients with LR of the total number of patients with LR in both groups combined.

To verify whether CAStotal, CASi, and CASm could be used to stratify patients in the VC, we used predetermined CAS cutoffs from the DC (FIG. 6). We found that high CASi, CASm and CAStotal were associated with poorer RFS compared to low CASi, CASm and CAStotal, respectively. Of the patients with LR, 75% were classified into the high CASi group (FIG. 6, Panel D) and ~67% of patients with LR were classified into the high CAStotal subgroups (FIG. 6, Panel E). Of the patients in the recurrence-free group, 87% were classified in the low CASm group (FIG. 6, Panel F). In both univariate and multivariate analyses after adjusting for potentially confounding effects of factors like age, grade, RT and receptor status CAStotal and comedo necrosis was the strongest and most significant independent predictor of RFS (i.e., HRs for CAStotal were higher than HRs of all other clinicopathologic factors (FIG. 4b). Similar to DC we observed that CASi and CASm also independently predicted the RFS (FIGS. 24 and 25).

In addition we performed the bootstrap analysis for the COX regression univariate and multivariate models on the combined (DC+VC=252) dataset and observed that mean HR for the univariate analysis is 5.22 and the multivariate analysis conditional on all other variables is 6.58 (p<0.0001) (FIG. 27 and FIG. 26). FIG. 26 shows a table representing the Hazard Ratios from univariate and multivariate bootstrap analysis for CAStotal (high vs low). FIG. 27 shows fitted normal and kernel density curves on the histogram are estimated based on the bootstrap sample mean and standard deviation. They show that 1000 hazard ratios are nearly normally distributed with light skewness. Panel A shows univariate analysis, and Panel B shows multivariate analysis.

Figure 32:
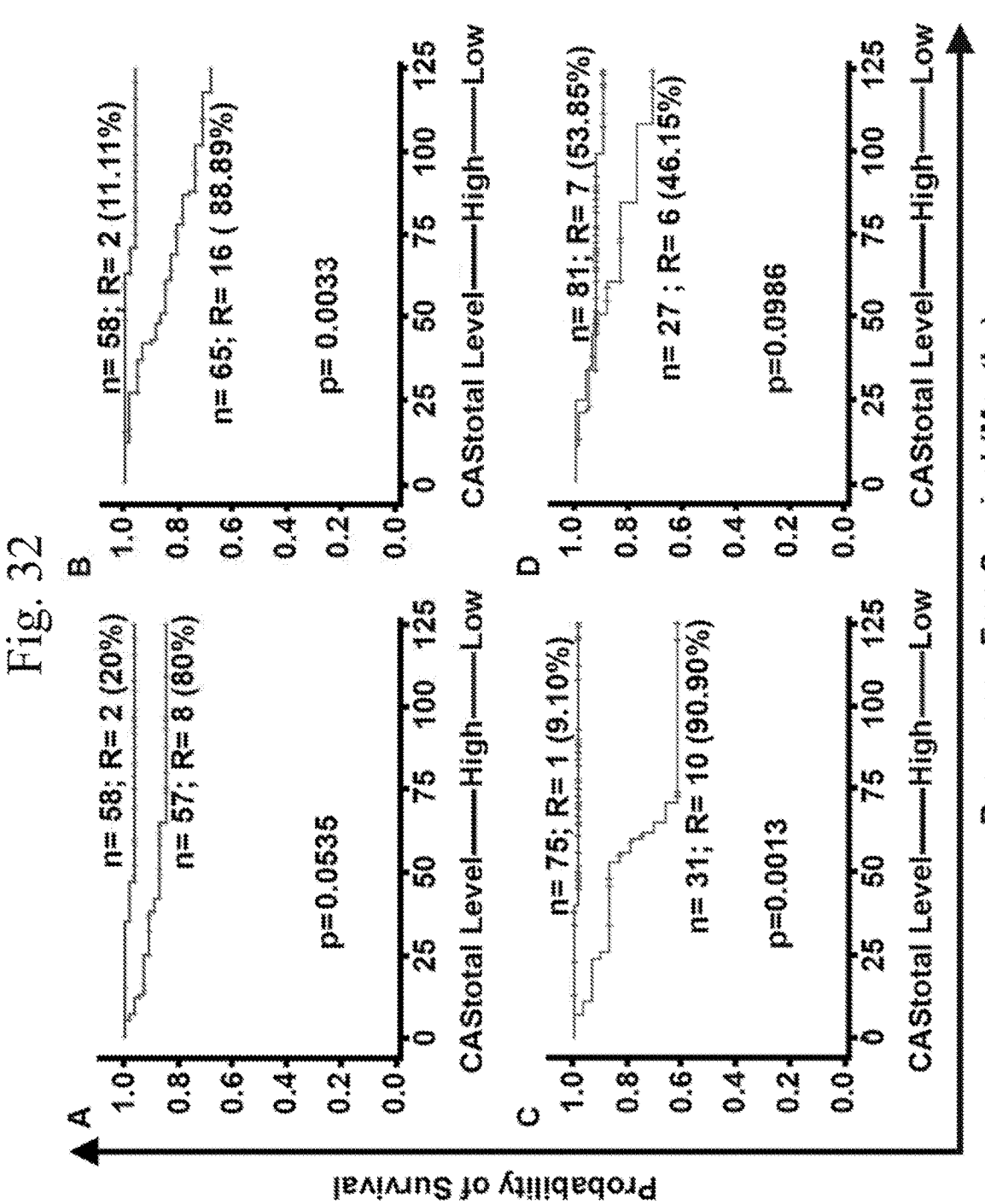
FIG. 32 is an exemplary illustration showing in DC and VC, higher CAS is associated with poorer RFS (regardless of whether the LR was in the form of DCIS or IBC) in accordance with embodiments of the present techniques.

Also, CAStotal was able to identify patients for both DCIS (FIG. 32, Panels A and B, FIG. 30, Panels Ai and Bii) and invasive recurrence even after adjusting for potentially confounding effects of factors like age, grade, and RT (FIG. 32, Panels C and D, FIG. 30, Panels Aii and Bii) in both DC and VC. (clinicopathological characteristics summarized in FIG. 28 and FIG. 29). FIG. 28 shows descriptive statistics of clinicopathological characteristics for pure DCIS based on the recurrence status in the DC (Panel A) where recurrence was in DCIS form and (Panel B) where recurrence was in invasive form. The $\chi^2$ p-values were used to determine if the differences in proportions were statistically significant. FIG. 29 shows descriptive statistics of clinicopathological characteristics for pure DCIS based on the recurrence status in the VC (Panel A) where recurrence was in DCIS form and (Panel B) where recurrence was in invasive form. The $\chi^2$ p-values were used to determine if the differences in proportions were statistically significant. FIG. 30 shows multivariate Cox proportional regression analysis for the risk of LR in DCIS treated with BCS or mastectomy comparing the influence of common clinicopathological variables and receptor status relative to CAStotal in (Panel Ai) DC where recurrence was in DCIS form, (Panel Aii) DC where recurrence was in invasive form (Panel Bi) VC where recurrence was in DCIS form (Panel Bii) VC where recurrence was in invasive form. FIG. 32 shows in DC and VC, higher CAS is associated with poorer RFS. Kaplan Meier survival curves representing the RFS of patients in the DC stratified into CAStotal high and low groups in, (Panel A) DC where recurrence was in DCIS form, (Panel B) DC where recurrence was in invasive form (Panel C) VC where recurrence was in DCIS form (Panel D) VC where recurrence was in invasive form. N: total number of patients in each group; R: number of percentage/proportion of patients with LR out of the total number of patients with LR in both groups combined. %: percentage/proportion of patients with LR of the total number of patients with LR in both groups combined. p<0.05 is considered significant.

Figure 33:
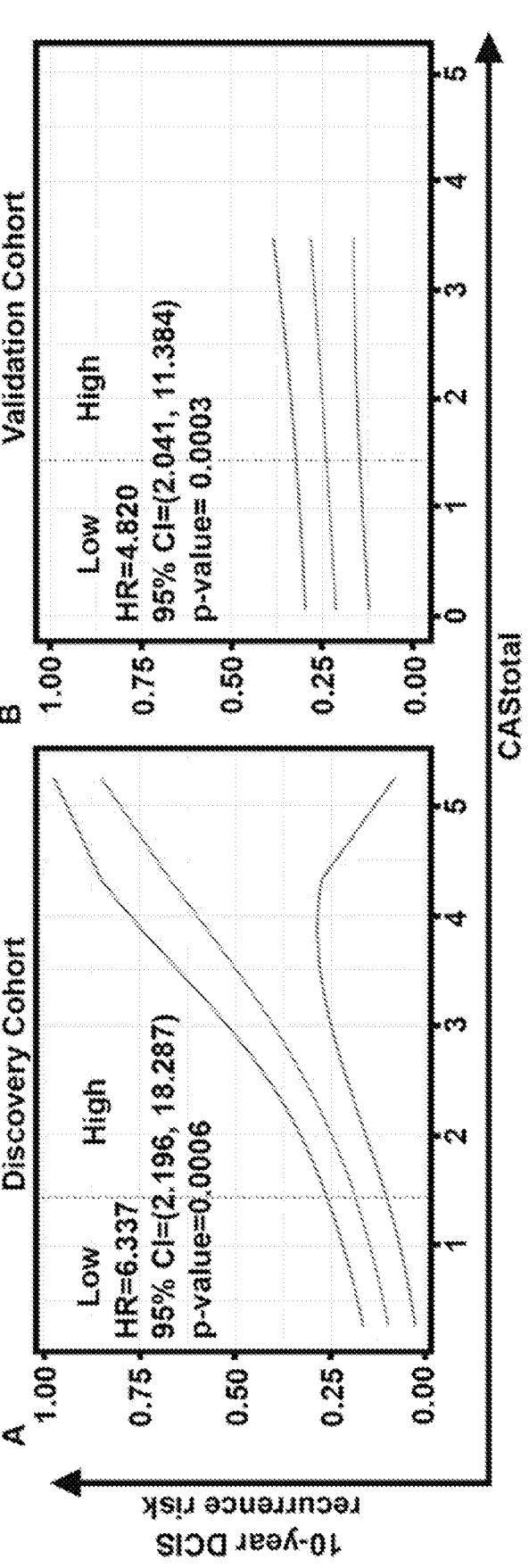
FIG. 33 is an exemplary illustration showing estimated 10-year risk of developing a LR in accordance with embodiments of the present techniques.

Further, in both the DC and VC, the 10-year estimated risk of LR increased continuously as the CAS increased (FIG. 33). FIG. 33 shows estimated 10-year risk of developing a LR as a continuous function using CAS based on a Cox proportional hazards model, including 95% confidence intervals demonstrating the level of precision in the estimates.

Next, we determined if our survival model had high predictive accuracy using the Harrell's concordance index. The higher the concordance index, the better the survival model discriminates between patients who experienced LR versus those who remained LR-free. The results indicated that any patient with a poorer/shorter RFS had a 72.6% probability of being in the high CAStotal group. Also, we created a 2×2 confusion matrix performance metrics to show the accuracy of CAS to predict 10-year LR. To do so, we calculated the sensitivity (Sn), specificity (Sp), positive predictive value (PPV), negative predictive value (NPV) and accuracy (Acc) of CAS and odds ratio (OR which represents the increase in odds of a patient in a high-risk group developing recurrence relative to a patient in a low-risk group), for both cohorts to compare the performance of CAS with that of the traditional clinicopathological variables (those used in the Cox regression analysis). As presented in the tables below, our CAStotal yielded an accuracy (or Acc) of 0.60, sensitivity of 0.85, specificity of 0.53, PPV of 0.32, NPV of 0.93, and OR of 6.8 in the DC (FIG. 31). FIG. 31 shows the 2×2 confusion matrix and performance metrics for CAStotal and common clinicopathological variables in the (Panel A) DC and (Panel B) VC. For each variable, the positive condition was recurrence within 10 years.

We noticed that the CAStotal produced a lower accuracy and specificity compared to comedo necrosis (0.71). However, comparison of the Sp, PPV, NPV, and OR performance metrics showed the overall superiority of CAStotal, in both cohorts, when compared to the clinicopathologic variables. Thus, these results collectively show that CAS can robustly predict 10-year LR risk for DCIS patients from two different cohorts.

CAS can identify patients who could benefit from radiotherapy.

Figure 34:
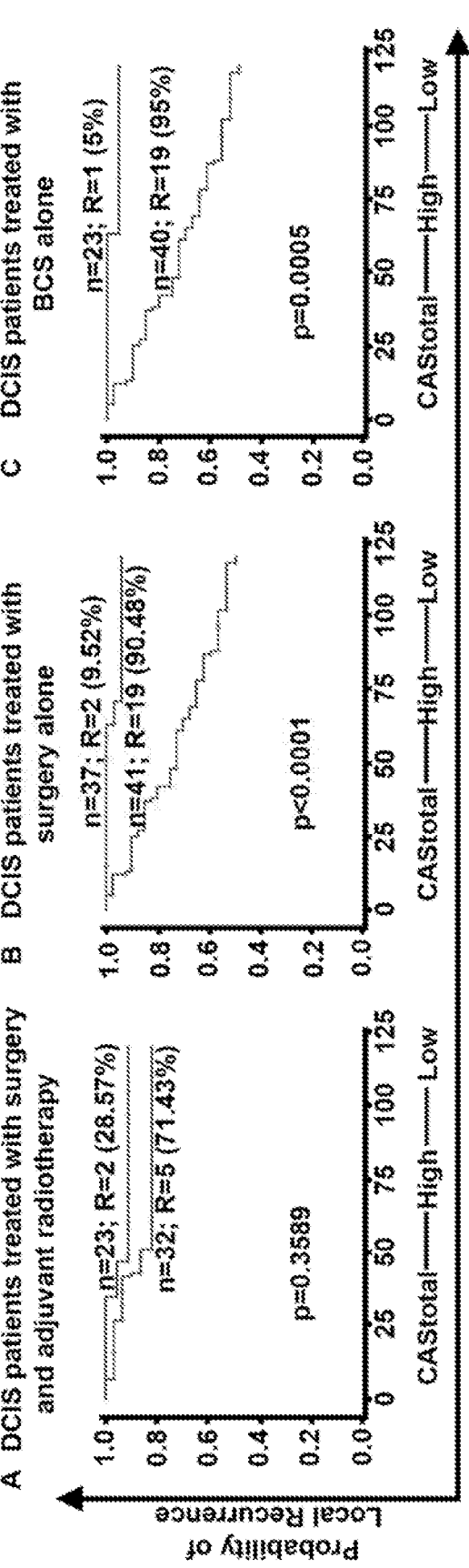
FIG. 34 is an exemplary illustration showing higher CAS is associated with poor RFS for DCIS patients treated with BCS alone in accordance with embodiments of the present techniques.

In the DC, CAStotal stratified DCIS patients treated with surgery (mastectomy/BCS) or BCS alone (FIG. 34, Panels B and C) into subgroups with high and low LR risks with greater significance relative to patients treated with surgery (mastectomy/BCS) and post-operative RT (FIG. 34, Panel A) (HR=11.6, p<0.0001 for surgery alone; HR=17.05, p=0.0005 for BCS alone, and HR=2.4, p=0.3589 for surgery+RT). FIG. 34 shows higher CAS is associated with poor RFS for DCIS patients treated with BCS alone: Kaplan Meier survival curves representing RFS of the DCIS patient subgroups stratified based on high vs. low CAStotal: (Panel A) DCIS patients treated with surgery and adjuvant RT (mastectomy/BCS+RT), (Panel B) DCIS patients treated with surgery alone (mastectomy/BCS), (Panel C) DCIS patients treated with BCS alone. N: total number of patients in each group; R: number of patients who showed LR; %: percentage/proportion of the patients with LR of the total number of patients with LR in both groups combined.

Figure 35:
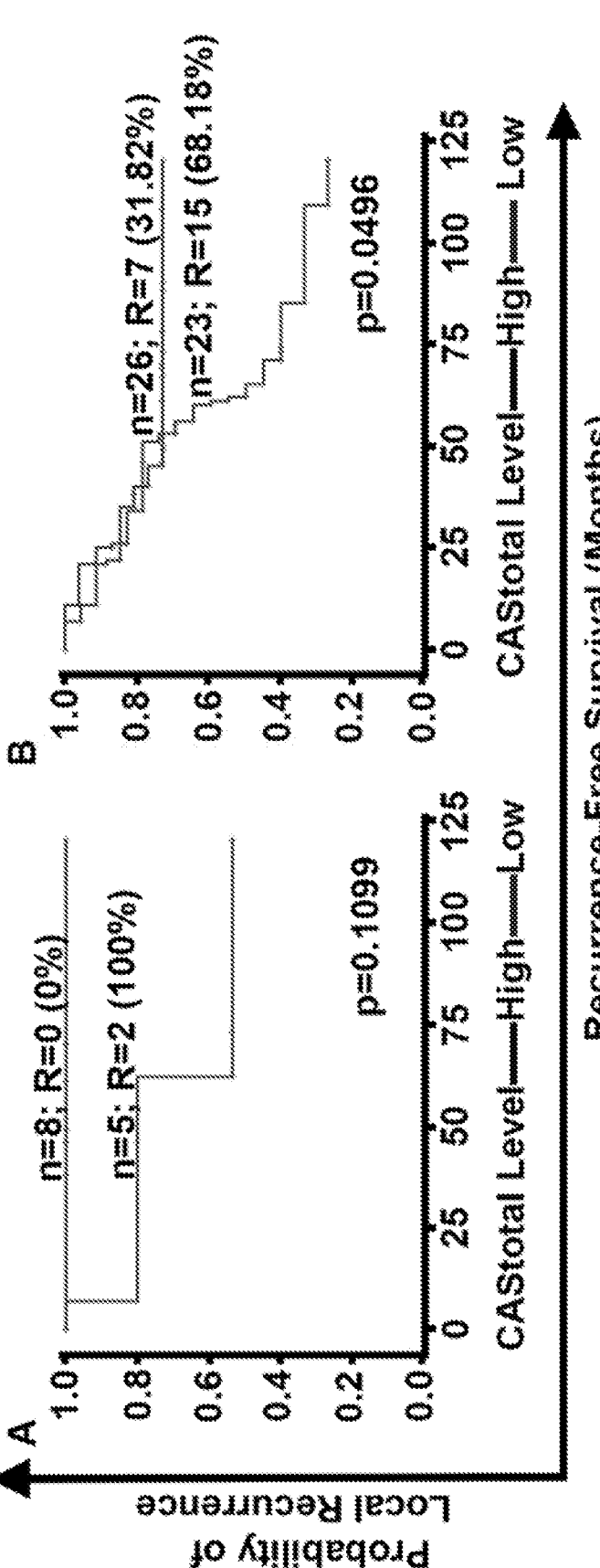
FIG. 35 is an exemplary illustration showing higher CAS is associated with poor RFS for DCIS patients in the VC treated with surgery alone in accordance with embodiments of the present techniques.

Similarly, in the VC, CAS stratified DCIS patients treated with surgery only (FIG. 35, Panels A and B) into subgroups with high and low LR risks with higher significance compared to patients treated with surgery (mastectomy or BCS) and post-operative adjuvant RT (surgery+RT) (HR=3.97, p=0.049 for surgery alone and HR=1.4, p=0.109 for surgery+RT). FIG. 35 shows higher CAS is associated with poor RFS for DCIS patients in the VC treated with surgery alone: Kaplan Meier survival curves representing the RFS of the DCIS patient subgroups stratified based on high vs. low CAStotal (CAStotal cutpoint used was the same as in the DC): (Panel A) DCIS patients treated with surgery (BCS/mastectomy) and adjuvant RT (surgery+RT), (Panel B) DCIS patients treated with surgery alone. N: total number of patients in each group; R: number of patients who showed LR; %: percentage/proportion of patients with LR of the total number of patients with LR in both groups combined. p<0.05 is considered significant.

Figure 36:
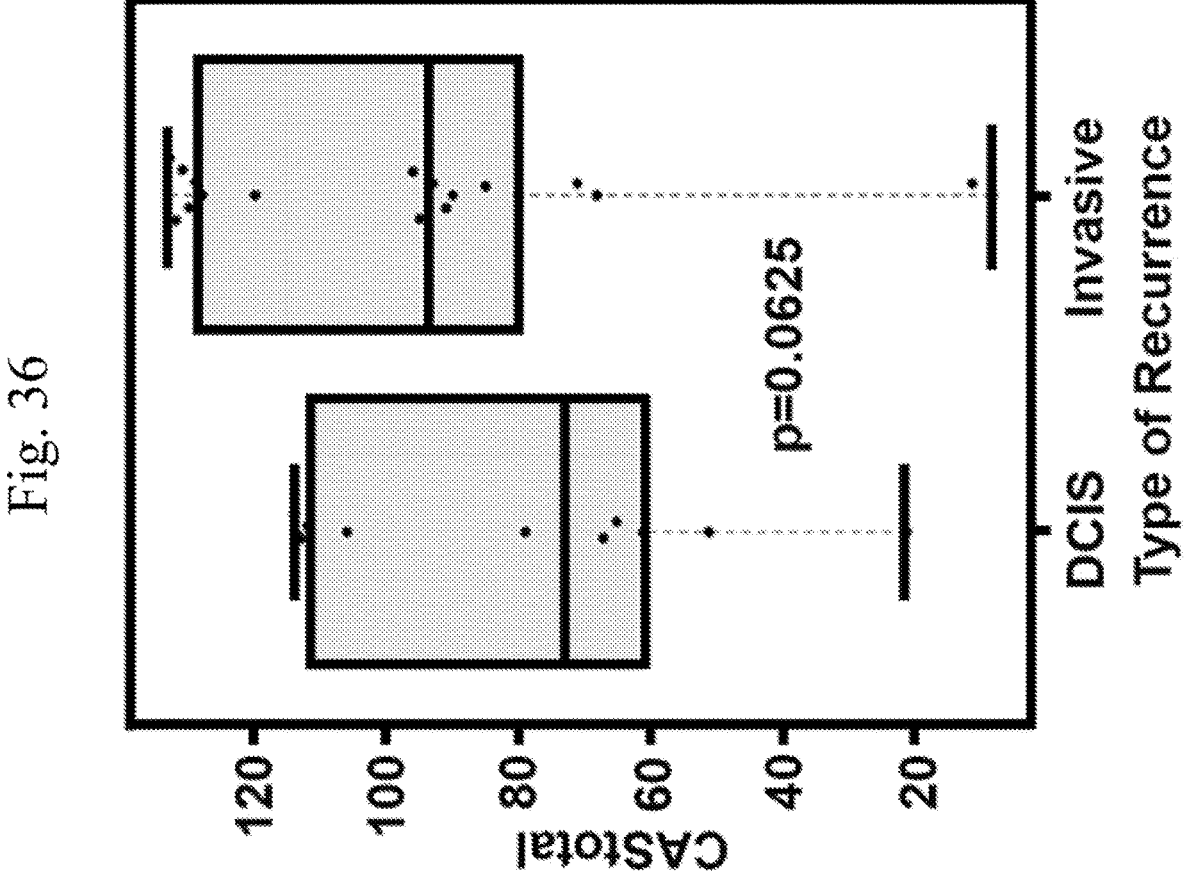
FIG. 36 is an exemplary illustration showing DCIS cases who recurred as IBC exhibited higher CAStotal compared to the patients who recurred as DCIS in accordance with embodiments of the present techniques.

These data suggest that CAStotal can identify LR patients who might benefit from adjuvant RT. In addition, we observed that DCIS patients who recurred as IBC exhibited higher CAStotal (p=0.07) compared to the patients who recurred as DCIS (FIG. 36) in the DC. FIG. 36 shows DCIS cases who recurred as IBC exhibited higher CAStotal compared to the patients who recurred as DCIS. Beeswarm Box plots showing CAStotal Wilcoxon ranks for pure DCIS who recurred as IBC (n=18) or DCIS (n=10).

Figure 37:
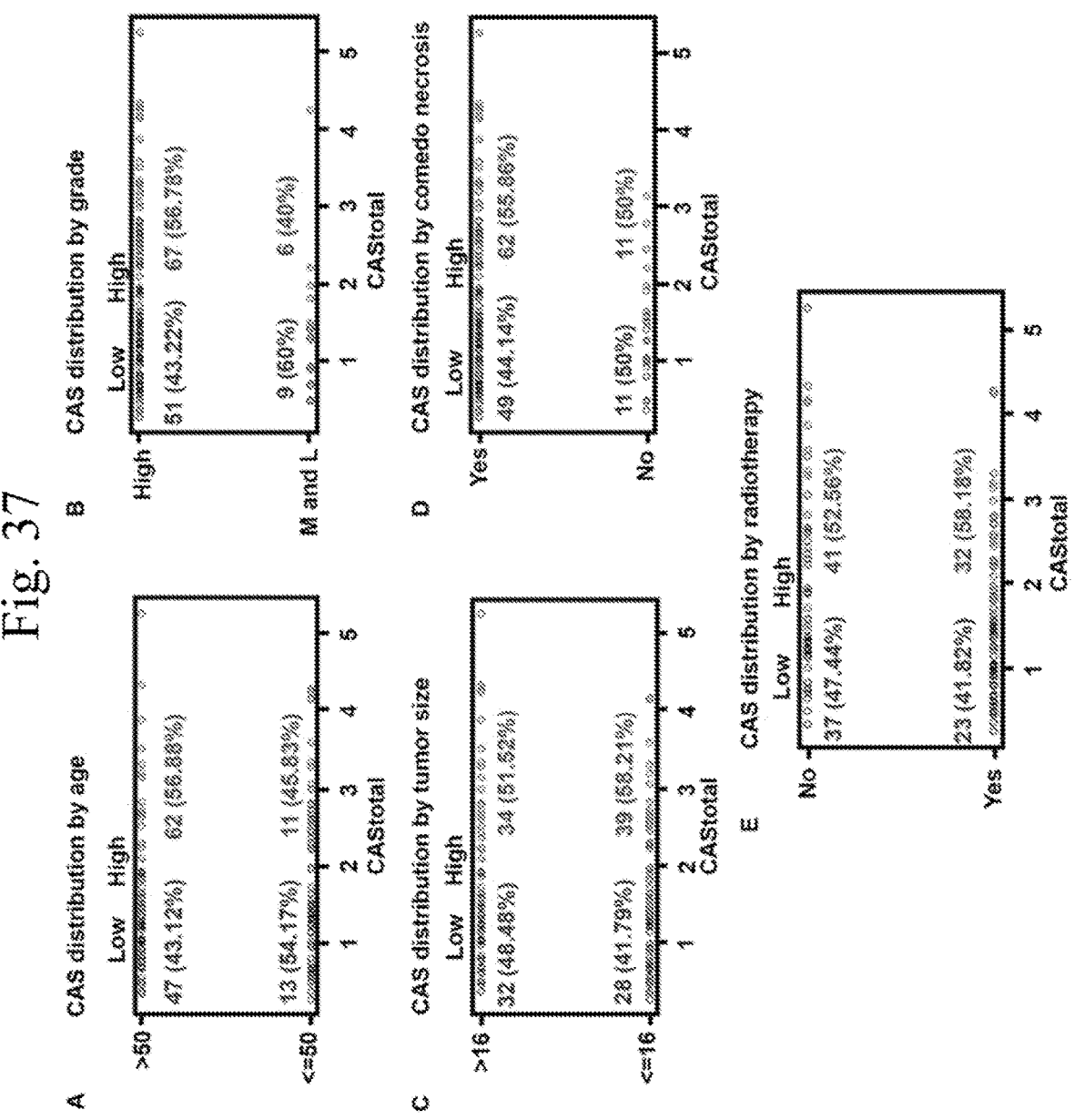
FIG. 37 is an exemplary illustration showing distribution of the CAStotal according to clinical and pathologic characteristics, including scatter plots and the frequency in each prespecified risk group for the DC in accordance with embodiments of the present techniques.
Figure 38:
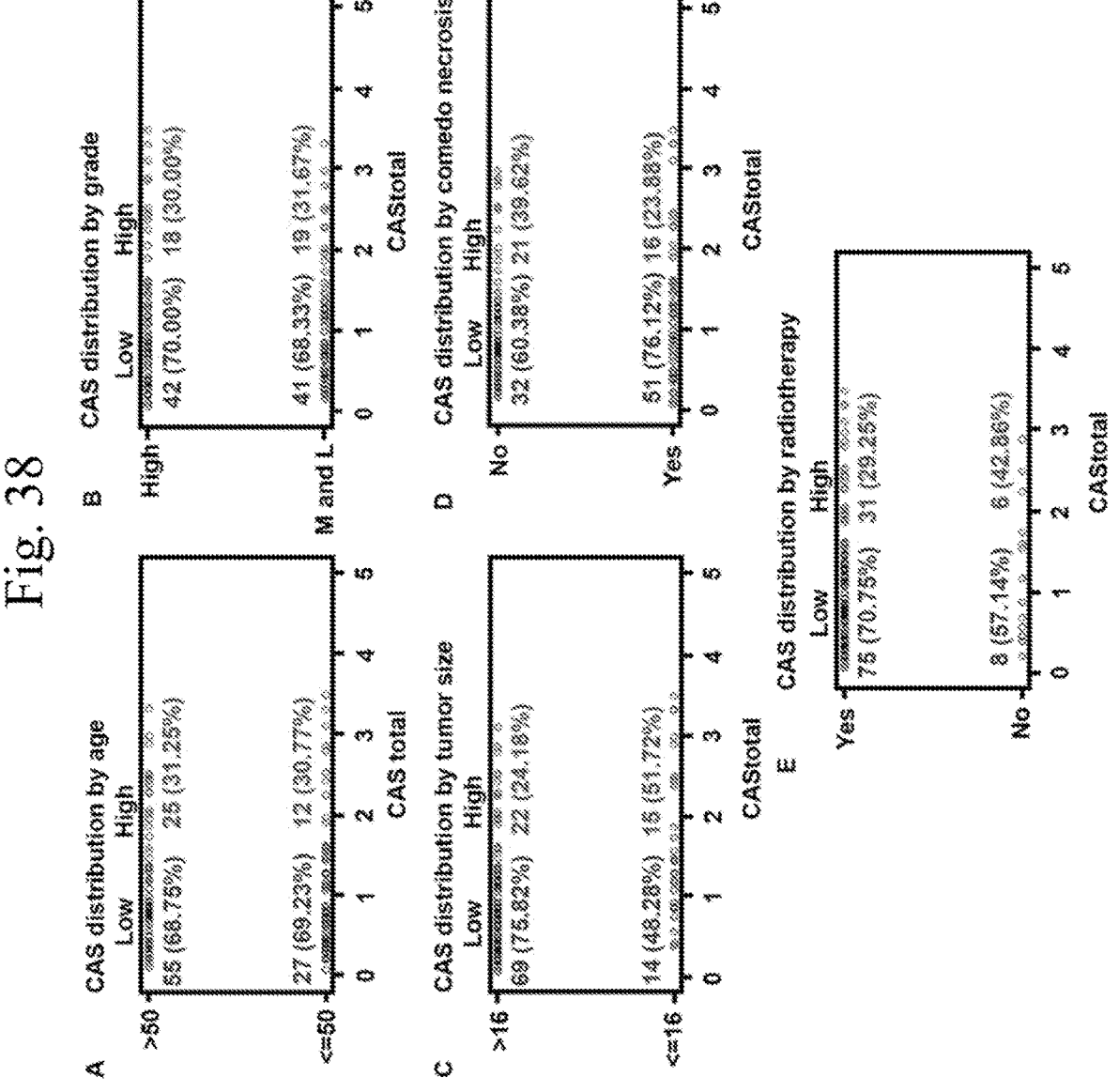
FIG. 38 is an exemplary illustration showing distribution of the CAStotal according to clinical and pathologic characteristics including scatter plots and the frequency in each prespecified risk group for the VC, in accordance with embodiments of the present techniques.

We next evaluated the clinical significance of CAS by examining the associations of CAS with traditionally-employed clinicopathological variables i.e., age, grade, tumor size, comedo necrosis, and RT (FIGS. 37 and 38). FIG. 37 shows distribution of the CAStotal according to clinical and pathologic characteristics, including scatter plots and the frequency in each prespecified risk group for the DC. Distribution of CAStotal according to (Panel A) age, (Panel B) grade, (Panel C) tumor size, (Panel D) comedo necrosis, and (Panel E) RT. Blue: number and percentage of patients in the low-CAStotal subgroup; Red: Number and percentage of patients in the high-CAStotal subgroup. FIG. 38 shows distribution of the CAStotal according to clinical and pathologic characteristics, including scatter plots and the frequency in each prespecified risk group for VC. Distribution of CAStotal according to (Panel A) age, (Panel B) grade, (Panel C) tumor size, (Panel D) comedo necrosis, and (Panel E) RT.

Our data shows that CAStotal provides clinically-relevant prognostic information over and beyond what is provided by current clinicopathologic parameters alone. Given that high CA is associated with more aggressive disease phenotypes, we not only observed the association of high CAStotal with higher recurrence rates (RR), but also found that CAStotal segments patient subgroups more deeply than traditional clinicopathologic parameters (see RR forest plot in FIG. 32). For example, the RR forest plot (FIG. 39A) for high grade DCTS patients in the DC showed that patients with comedo necrosis (red), are at high risk of recurrence (0.59) compared to the overall RR for patients (0.33), regardless of the CAS of their tumors. FIG. 39A shows CAStotal allows deeper stratification of patient subgroups than traditional clinicopathologic parameters alone in the HG DCTS patient subgroups from the DC. Forest plot representing estimates of 10-year RRs (with 95% CTs) within HG DCTS patient subgroups (from the DC) defined by clinical parameters alone, or within the CAStotal high and low risk subpopulations within these subgroups. The CAStotal cutpoint used here was that used for the whole DC patient population (133 patients) and not the optimal cutpoint for the patient subgroup. The black box represents the overall RR observed for the DCTS patients in the DC. The red boxes represents the RR observed among the patients in the specific subgroup defined by the clinical parameter (regardless of their CAStotal). The green boxes represents the RR in the high CAStotal subpopulation and the blue boxes represents the RR in the low CAStotal sub-population within each subgroup.

Figure 39B:

When we further stratified these DCTS patients with comedo necrosis into high (green) and low (blue) CAS groups, we observed that the RR for the high CAS group (green) was 0.83 and RR for the low CAS subgroup (blue) was 0.10. Similar results were observed for VC (see RR forest plot in FIG. 39B). FIG. 39B shows CAStotal enables deeper stratification of patient subgroups than traditional clinicopathologic parameters alone in the VC. Forest plot representing estimates of 10-year RRs (with 95% CTs) within DCTS patient subgroups (from VC) defined by clinical parameters alone, or within the CAStotal high- and low-risk subpopulations within these subgroups. The CAStotal cutpoint used here was the cutpoint used for the entire DC patient population (119 patients) and not the optimal cutpoint for the patient subgroup. The black box represents the overall RR observ2eld for the DCTS patients in the DC. The red boxes represents the RR observed for the patients in the specific subgroup defined by the clinical parameter (and regardless of their CAStotal). The green boxes represent the RRs in the high CAStotal sub-population, and the blue box represent the RRs in the low CAStotal sub-population within each subgroup. Thus, CAS was able to more deeply segment the patients with comedo necrosis into high and low risk LR groups. Similar trends were evident for tumor size, RT, and age.

CAS stratification of DCIS patients into LR and LR-free groups is superior to that afforded by the Van Nuys Prognostic Index (VNPI).

Figure 7:
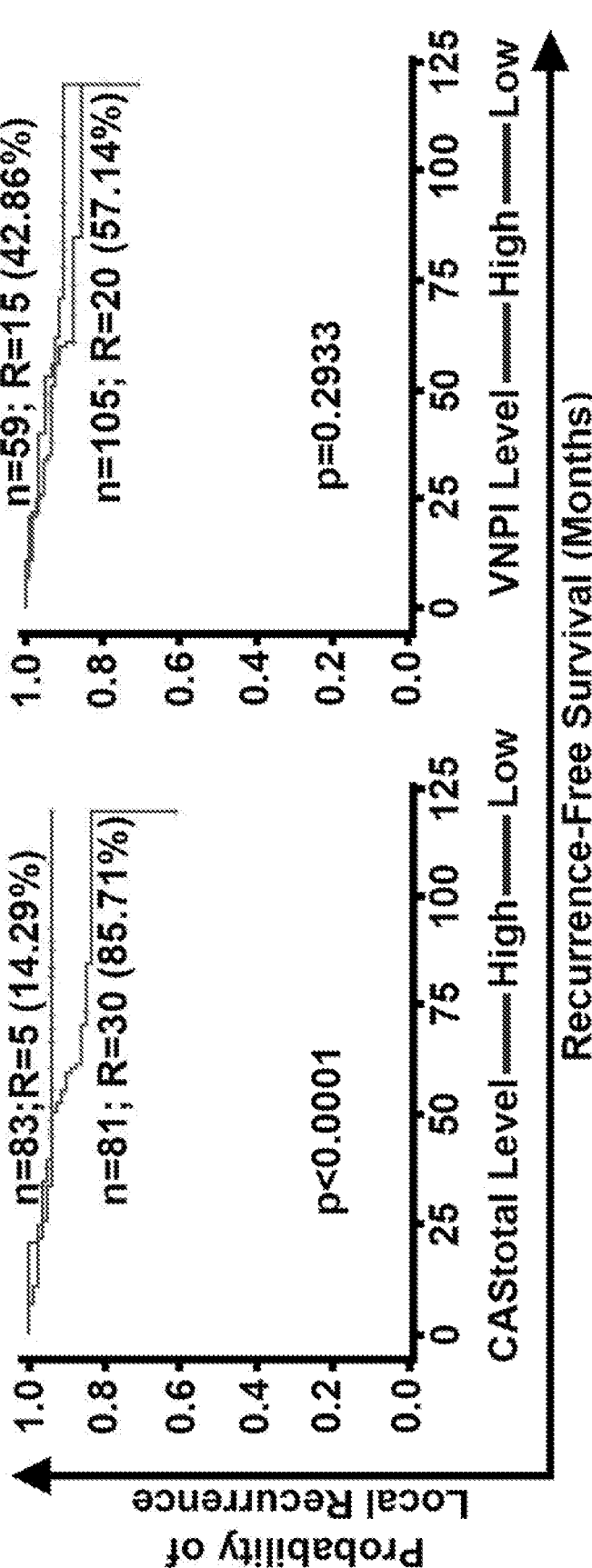
FIG. 7 is an exemplary illustration showing comparison of the stratification of DCIS patients by CAStotal and Van Nuys Prognostic Index (VNPI) in accordance with embodiments of the present techniques.

The widely used VNPI is based on patients' age at diagnosis, tumor size, resection margin width and tumor grade. To test the performance of this index in our (DC and VC combined) cohort, we calculated VNPI based on scoring methods described in the literature. Each of the factors was assigned a score between 1-3, and the sum of scores for the four parameters (i.e., the final VNPI score) was used to stratify patients into high, low and intermediate risk groups for LR, employing the binary cutoff score of [3]8. Next, we compared the performance of VNPI and CAStotal in cases from the DC and VC (n=164) (FIG. 7, Panels A and B) using univariate and Kaplan Meier survival analyses. FIG. 7 shows comparison of the stratification of DCIS patients by CAStotal and Van Nuys Prognostic Index (VNPI). Kaplan Meier survival curves representing the RFS of DCIS patients (n=164) stratified by (Panel A) CAStotal, and (Panel B) VNPI. N: total number of patients in each group; R: number of patients who showed LR; %: percentage/proportion of patients with LR out of the total number of patients with LR in the DC and VC combined.

We found that higher VNPI was not significantly associated with poorer RFS and VNPI did not significantly stratify patients as high and low risk of LR subgroups. By contrast, CAStotal stratified DC and VC patients into subgroups of high and low risk of LR with greater significance and HRs (CAStotal HR=5.6 vs. VNPI HR=0.70) (FIG. 40). FIG. 40 shows univariate analyses evaluating the impact of CAStotal and VNPI on the RFS of DCIS patients treated with BCS.

Multivariable analyses adjusted for other potentially confounding factors, such as tumor size, presence of comedo necrosis, age, and RT along with VNPI and CAS, revealed that CAStotal showed the highest association with RFS, with a HR=6.86 (FIG. 41). FIG. 41 shows multivariate analyses evaluating the impact of CAStotal, VNPI and other clinicopathological parameters on the RFS of DCIS patients treated with BCS. These findings compellingly suggest that the CAS stratification of DCIS patients is superior to that of the traditionally-used VNPI.

DISCUSSION

DCIS exhibits considerable inter-patient heterogeneity and has a poorly understood natural history. A lack of accurate models for prediction of risk of LR results in over- and under-treatment, complicated by the variable prognostic evidence of patient age, tumor margins, DCIS grade, and size. CA is a hallmark of cancers and is observable in >80% of breast tumors including pre-invasive lesions, and is associated with high grade in DCIS and IBC. Amplified centrosomes are present in premalignant cells and increase as the disease progresses to dysplasia, highlighting the potential involvement of CA in neoplastic transformation and progression.

Our laboratory has previously shown that (a) high levels of CA are associated with poor progression free survival in invasive breast tumors, and (b) CA is higher in the aggressive triple-negative breast cancer (TNBC) subtype compared to grade-matched non-TNBCs. This notion was further validated by analysis of the CA20 gene score, which is based on genes associated with CA. Recent studies have reported that higher CA induces high-grade features in BCs; thus, CA has been associated with tumor evolution (29). Although studies have reported that BCs exhibit structurally amplified centrosomes, they have not yet established the prognostic value of this structural CA. This may be due, in part, to the 2D (i.e., cross-sectional) approaches used in these studies, which have limitations to accurately capture the 3D size of the centrosome. Moreso, most studies (31) examining CA in BCs have not rigorously evaluated confounding effects of other clinicopathologic variables on the prognostic value of CA.

Our new semi-automated methodology uses quantitative centrosomal phenotyping and an algorithm to measure both numerical and structural centrosomal aberrations in DCIS tumors. For each sample, a continuous CAS was computed that categorized patients as having a high or low 10-year risk of LR. Findings from our retrospective study, which involved two large, well-characterized cohorts (DC and VC) of DCIS cases, showed that patients with LR within 10 years exhibited higher CAStotal relative to LR-free patients. Our study is the first to show that organellar-level differences distinguish DCIS patients with LR from LR-free patients, and that high levels of both numerical and structural CA are associated with increased 10-year risk of LR in DCIS patients. Our results suggest that aberrant centrosomal homeostasis in DCIS drives pathophysiological alterations that potentially facilitate disease progression through CIN-dependent as well as CIN-independent mechanisms. While CA may drive ITH through CIN, an increased centrosome complement may, via modulation of the microtubule cytoskeleton, enhance directional migration and invasion of malignant cells and thus enhance the risk of LR in the longer term. We have demonstrated that CAStotal is significantly and independently associated with poor RFS, and upon inclusion of both CAStotal and VNPI into multivariable models, we found that CAStotal outperforms VNPI in predicting LR. CAStotal predicts the 10-year risk of LR with higher concordance than VNPI. In DCIS patient subsets, defined based on their clinical and histopathological parameters, stratification by CAStotal prognostically augmented several clinicopathologic parameters in determining rate of recurrence. Among subsets of DCIS patients treated with BCS or those receiving additional adjuvant RT, CAStotal identified patients with high risk of LR. Thus, CAStotal can be used as a clinical tool to identify patients who can be safely treated with BCS/mastectomy alone, and those who will benefit from the inclusion of RT. Our centrosomal profiling methodology, which dichotomizes DCIS patients into high- and low-risk categories, enables clear go/no-go therapeutic decision making, and can substantially augment individualized management of DCIS based upon risk conferred by the patient's centrosomal complement.

CAS, as the linear expression of the severity and frequency of numerical and structural CA, may serve as an indirect measure of ITH in DCIS. Our study, the first to robustly quantify CA in both pure and mixed DCIS samples, has contributed evidence supporting a model of CA-driven DCIS progression into IBC. These findings concur with previous studies wherein we, and others, observed that TNBC, the most aggressive subtype of BC, exhibits highest CA among all BC subtypes. Centrosome profiling can complement clinicopathologic and genomic evaluation to provide a comprehensive portrait of disease status. An exciting avenue for future research is to profile CA in all the stages of tumor progression starting from atypical hyperplasia to invasive and metastatic disease to evaluate if CA can function as a biomarker for tumor evolution.

The commercially available Oncotype Dx DCIS score is applicable mainly to cases with resection margins of at least 3 mm and low/intermediate-grade DCIS measuring ≤2.5 cm, or in high-grade DCIS of ≤1 cm, as this is the set of patients from the ECOG 5194 study upon which the test was initially clinically validated. By contrast, our quantitative centrosomal phenotyping methodology is more broadly applicable and could be refined for other cancer types with rampant CA. The gene signature that comprises the basis of the Oncotype DCIS Score consists mainly of proliferation-related genes. CA is a phenotypic biomarker that serves as a readout of hundreds of deregulated signaling pathways that culminate in numerical and/or structural CA, including dysregulated proliferation-related signaling cascades. Thus, our methodology captures prognostic information from a broader swath of biological pathways that are deregulated in and drive the biology of DCIS. CAS-based risk profiling of core biopsies may reduce the number of re-excisions even in the event of close/positive margins.

However, our study has a few limitations. There are imbalances in the number of patients in different subgroups, in the DC and the VC of the study, which has resulted in better performance of CAS (higher HR) in the DC. While the DC has more high-grade patients, the VC has a balanced number of high, intermediate, and low-grade patients. High-grade patients tend to present with invasive recurrence. A higher number of patients recurred as invasive in the DC and patients with invasive recurrence exhibited higher CAS when compared to patients who recurred as DCIS in DC. Whereas, in VC due to more balanced numbers of high, intermediate, and low-grade patients, no such variation in the type of LR was observed. Furthermore, lack of receptor status in some cases precluded study of the confounding effect of receptors in this dataset. The study cohort did not include any patients treated with endocrine therapy. These limitations in the DC and VC perhaps lead to the slightly different performance of CAS among the two cohorts. Validation studies in external cohorts and mechanistic studies to understand the role of CA-associated proteins in DCIS progression model are warranted.

Figure 44:
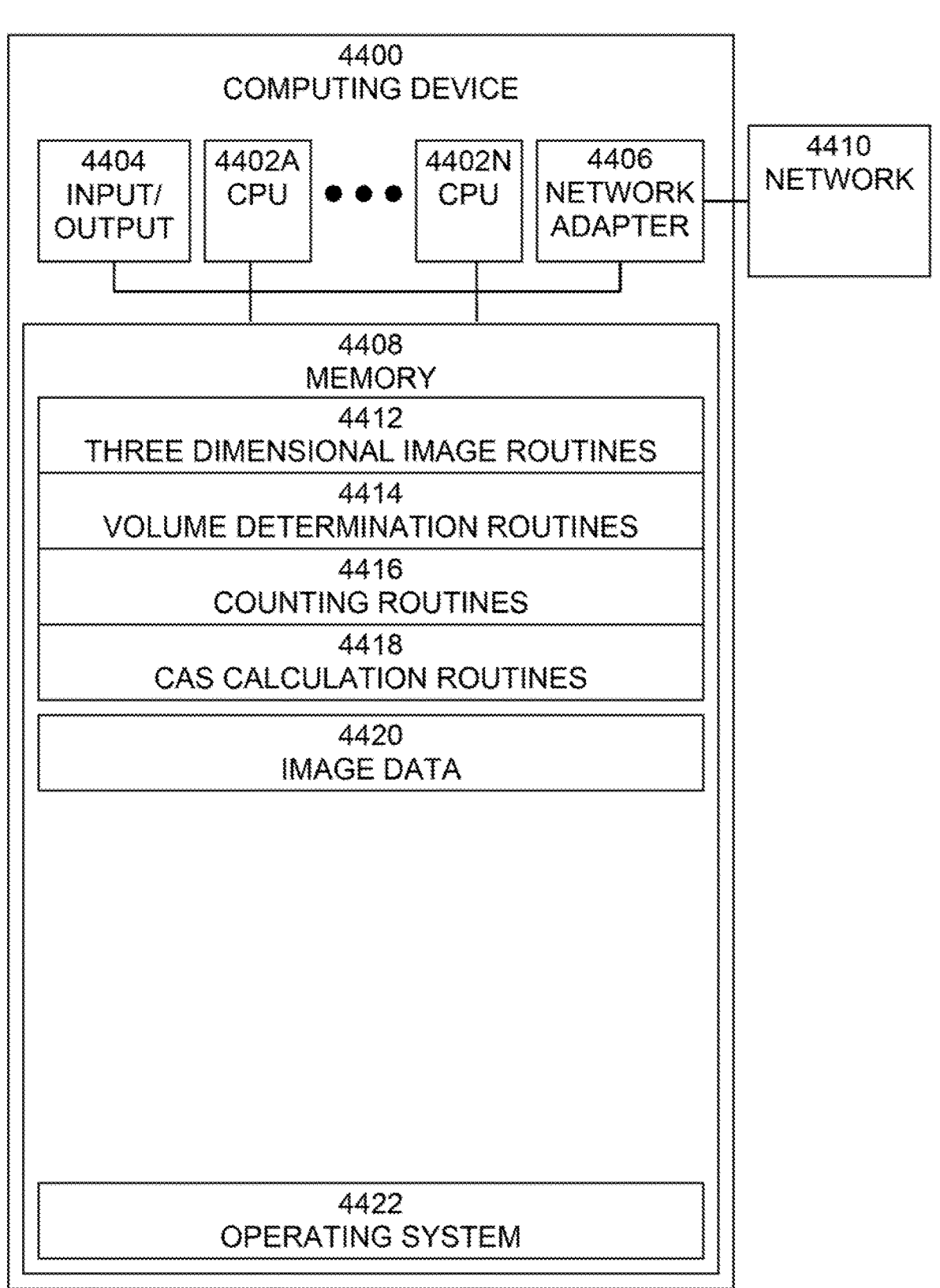
FIG. 44 is an exemplary block diagram of a computer system, in which processes involved in the embodiments described herein may be implemented.

An exemplary block diagram of a computer system 4402, in which processes involved in the embodiments described herein may be implemented, is shown in FIG. 44. Computer system 4402 may be implemented using one or more programmed general-purpose computer systems, such as embedded processors, systems on a chip, personal computers, workstations, server systems, and minicomputers or mainframe computers, or in distributed, networked computing environments. Computer system 4402 may include one or more processors (CPUs) 4402A-4402N, input/output circuitry 4404, network adapter 4406, and memory 4408. CPUs 4402A-4402N execute program instructions in order to carry out the functions of the present communications systems and methods. Typically, CPUs 4402A-4402N are one or more microprocessors, such as an INTEL CORE® processor. FIG. 44 illustrates an embodiment in which computer system 4402 is implemented as a single multiprocessor computer system, in which multiple processors 4402A-4402N share system resources, such as memory 4408, input/output circuitry 4404, and network adapter 4406. However, the present communications systems and methods also include embodiments in which computer system 4402 is implemented as a plurality of networked computer systems, which may be single-processor computer systems, multi-processor computer systems, or a mix thereof.

Input/output circuitry 4404 provides the capability to input data to, or output data from, computer system 4402. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 4406 interfaces device 4400 with a network 4410. Network 4410 may be any public or proprietary LAN or WAN, including, but not limited to the Internet.

Memory 4408 stores program instructions that are executed by, and data that are used and processed by, CPU 4402 to perform the functions of computer system 4402. Memory 4408 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 4408 may vary depending upon the function that computer system 4402 is programmed to perform. In the example shown in FIG. 44, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In embodiments, at least a portion of the software shown in FIG. 44 may be implemented on a current leader server. Likewise, in embodiments, at least a portion of the software shown in FIG. 44 may be implemented on a computer system other than the current leader server.

In the example shown in FIG. 44, memory 4408 may include three dimensional image routines 4412, volume determination routines 4414, counting routines 4416, CAS calculation routines 4418, image data 4420, and operating system 4422. Three dimensional image routines 4412 may include software routines to generate three dimensional image data 4420 sufficient for volume rendering of iCTRs and mCTRs in the ROI, as described above. Volume determination routines 4414 may include software routines to determine the volume of each iCTR and mCTR in the ROI, as described above. Counting routines 4416 may include software routines to support the entry of data, including numbers of iCTRs and mCTRs associated with each cell nucleus in an ROI, and/or to automatically determine numbers of iCTRs and mCTRs per nucleus in the ROI, as described above. CAS calculation routines 4418 may include software routines to calculate one or more centrosome amplification scores (CASs) based on the number of iCTRs associated with each cell nucleus, number and percentage of cell nuclei associated with iCTRs, number and percentage of cell nuclei associated with mCTRs, number of mCTRs associated with each cell nucleus and the volume of each iCTR and mCTR, as described above. Operating system 4422 may provide overall system functionality.

As shown in FIG. 44, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewall s, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method of determining a 10 year risk of local recurrence of a patient diagnosed with a carcinoma in situ, the method comprising:

(a) acquiring three-dimensional optical sections of a sample of tumor tissue or cancer cells from the patient using confocal microscopy, wherein the sample is processed for visualization and demarcation of cell nuclei, individually distinguishable centrosomes (iCTRs) and megacentrosomes (mCTRs) in a region of interest (ROI) defined by a plurality of cell nuclei;

(b) processing the optical sections using volume rendering software to generate three-dimensional volumetric data for each centrosome, wherein background subtraction and fluorescence intensity thresholds are applied to distinguish centrosomes from non-specific signals (c) determining a volume of each iCTR and mCTR in the ROI based on the three-dimensional volumetric data (d) determining numbers of ICTRs and mCTRs associated with each cell nucleus in the ROI, wherein a centrosome is categorized as an iCTR when the volume of the centrosome is within a range of volumes found in normal tissue, and a centrosome is categorized as an mCTR when the volume of the centrosome is greater than the range of volumes found in normal tissue:

(e) determining severity and frequency of numerical and structural centrosome amplification present the sample based on the determined volumes and numbers of iCTRs and mCTRs from the patient; and (f) determining at least one centrosome amplification score (CAS) value for the sample based on the determined severity and frequency of numerical and structural centrosome amplification in the sample, wherein the determined at least one CAS value provides a measure of a level of a 10 year risk of local recurrence associated with the carcinoma in situ.

2. The method of claim 1, wherein determining severity and frequency comprises:

(a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei;

(b) determining a volume of each iCTR and mCTR in the ROI; and (c) determining numbers of iCTRs and mCTRs associated with each cell nucleus in the ROI, wherein a centrosome is categorized as an iCTR when the volume of the centrosome is within a range of volumes found in normal tissue, and a centrosome is categorized as an mCTR when the volume the centrosome is greater than the range of volumes found in normal tissue.

3. The method of claim 2, wherein the range of volumes found in normal tissue is about 0.20-0.74 cubic microns for breast tissue stained to visualize gamma-tubulin distribution.

4. The method of claim 2, wherein determining at least one CAS value comprises:

(d) calculating at least one structural CAS value for the sample based on the determined volumes of each iCTR and mCTR in the ROI, wherein the total structural CAS value is an aggregate value of both frequency and severity of structural centrosome amplification;

(e) calculating at least one numerical CAS value for the sample based on the determined numbers of iCTRs and mCTRs associated with each cell nucleus in the ROI, wherein the total numerical CAS value is an aggregate value of both frequency and severity of numerical centrosome amplification; and (f) calculating at least one total CAS value for the sample based the at least one structural CAS value and the at least one numerical CAS value;

wherein the at least one structural CAS value, the at least one numerical CAS value, and the at least one total CAS value provides a measure of a level of a 10 year risk of local recurrence associated with the carcinoma in situ.

5. The method of claim 4, wherein an above-threshold CAS value indicates a greater risk of local recurrence of the carcinoma in situ than does a below-threshold CAS value, wherein the threshold is an optimal cutoff value determined based on log-rank tests that minimizes the log-rank p-value for stratifying patients into high-risk and low-risk groups.

6. The method of claim 5, wherein the CAS value is an independent predictor of relapse-free survival after accounting for potentially confounding factors including at least one of tumor grade, patient age, comedo necrosis, patient treatment with radiotherapy, and receptor status.

7. The method of claim 5, wherein an above-threshold numerical CAS value indicates a greater risk of local recurrence of the carcinoma in situ than does a below-threshold numerical CAS value, wherein the threshold is an optimal cutoff value determined based on log-rank tests that minimizes the log-rank p-value for stratifying patients into high-risk and low-risk groups.

8. The method of claim 5, wherein an above-threshold structural CAS value indicates a greater risk of local recurrence of the carcinoma in situ than does a below-threshold structural CAS value, wherein the threshold is an optimal cutoff value determined based on log-rank tests that minimizes the log-rank p-value for stratifying patients into high-risk and low-risk groups.

9. The method of claim 5, wherein an above-threshold total CAS value indicates a greater risk of local recurrence of the carcinoma in situ than does a below-threshold total CAS value, wherein the threshold is an optimal cutoff value determined based on log-rank tests that minimizes the log-rank p-value for stratifying patients into high-risk and low-risk groups.

10. The method of claim 9, wherein the total CAS value stratifies patients into those at high risk of recurrence of carcinoma in situ and into those at low risk of recurrence of carcinoma in situ.

11. The method of claim 10, wherein the total CAS value stratifies patients diagnosed with carcinoma in situ into those at high risk of local recurrence of carcinoma in situ and into those at low risk of local recurrence of carcinoma in situ after accounting for confounding factors including at least one of tumor grade, patient age, comedo necrosis, patient treatment with radiotherapy, and receptor status and wherein the stratification provided by the total CAS value is superior to the stratification provided by the Van Nuys Prognostic Index.

12. The method of claim 9, wherein the above-threshold total CAS value indicates patients that have had breast conservation surgery for the carcinoma in situ who would benefit from adjuvant radiotherapy, wherein the threshold is an optimal cutoff value determined based on log-rank tests that minimizes the log-rank p-value for stratifying patients into high-risk and low-risk groups.

13. A computer program product for determining the 10-year local recurrence risk profile of a patient diagnosed with a carcinoma in situ, the computer program product comprising a non-transitory computer readable storage having program instructions embodied therewith, the program instructions executable by a computer, to cause the computer to perform a method comprising:

(a) acquiring three-dimensional optical sections of a sample of tumor tissue or cancer cells from the patient using confocal microscopy, wherein the sample is processed for visualization and demarcation of cell nuclei, individually distinguishable centrosomes (iCTRs) and megacentrosomes (mCTRs) in a region of interest (ROI) defined by a plurality of cell nuclei;

(b) processing the optical sections using volume rendering software to generate three-dimensional volumetric data for each centrosome, wherein background subtraction and fluorescence intensity thresholds are applied to distinguish centrosomes from non-specific signals (c) determining a volume of each iCTR and mCTR in the ROI based on the three-dimensional volumetric data (d) determining numbers of iCTRs and mCTRs associated with each cell nucleus in the ROI, wherein a centrosome is categorized as an iCTR when the volume of the centrosome is within a range of volumes found in normal tissue, and a centrosome is categorized as an mCTR when the volume of the centrosome is greater than the range of volumes found in normal tissue:

(e) determining severity and frequency of numerical and structural centrosome amplification present within the sample based on the determined volumes and numbers of iCTRs and mCTRs from the patient; and (f) determining at least one centrosome amplification score (CAS) value for the sample based on the determined severity and frequency of numerical and structural centrosome amplification in the sample, wherein the determined at least one CAS value provides a measure of a level of a 10 year risk of local recurrence associated with the carcinoma in situ.

14. The computer program product of claim 13, wherein determining severity and frequency comprises:

(a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei;

(b) determining a volume of each iCTR and mCTR in the ROI; and (c) determining numbers of iCTRs and mCTRs associated with each cell nucleus in the ROI, wherein a centrosome is categorized as an iCTR when the volume of the centrosome is within a range of volumes found in normal tissue, and a centrosome is categorized as an mCTR when the volume the centrosome is greater than the range of volumes found in normal tissue.

15. The computer program product of claim 14, wherein the range of volumes found in normal tissue is about 0.20-0.74 cubic microns for breast tissue stained to visualize gamma-tubulin distribution.

16. The computer program product of claim 15, wherein determining at least one CAS value comprises:

(d) calculating at least one structural CAS value for the sample based on the determined volumes of each iCTR and mCTR in the ROI, wherein the total structural CAS value is an aggregate value of both frequency and severity of structural centrosome amplification;

(e) calculating at least one numerical CAS value for the sample based on the determined numbers of iCTRs and mCTRs associated with each cell nucleus in the ROI, wherein the total numerical CAS value is an aggregate value of both frequency and severity of numerical centrosome amplification; and (f) calculating at least one total CAS value for the sample based the at least one structural CAS value and the at least one numerical CAS value;

wherein the at least one structural CAS value, the at least one numerical CAS value, and the at least one total CAS value provides a measure of a level of a 10 year risk of local recurrence associated with the carcinoma in situ.

17. The computer program product of claim 16, wherein an above-threshold CAS value indicates a greater risk of local recurrence of the carcinoma in situ than does a below-threshold CAS value, wherein the threshold is an optimal cutoff value determined based on log-rank tests that minimizes the log-rank p-value for stratifying patients into high-risk and low-risk groups.

18. The computer program product of claim 16, wherein the CAS value is an independent predictor of relapse-free survival after accounting for potentially confounding factors including at least one of tumor grade, patient age, comedo necrosis, patient treatment with radiotherapy, and receptor status.

19. The computer program product of claim 16, wherein at least one of:

an above-threshold numerical CAS value indicates a greater 10-year risk of local recurrence of the carcinoma in situ than does a below-threshold numerical CAS value;

an above-threshold structural CAS value indicates a greater 10-year risk of local recurrence of the carcinoma in situ than does a below-threshold structural CAS value;

an above-threshold CAS value indicates a greater 10-year risk of local recurrence of the carcinoma in situ than does a below-threshold total CAS value;

the total CAS value stratifies patients into those at high 10-year risk of recurrence of carcinoma in situ and into those at low 10-year risk of recurrence of carcinoma in situ;

the total CAS value stratifies patients into those at high 10-year risk of recurrence of carcinoma in situ and into those at low 10-year risk of recurrence of carcinoma in situ after accounting for confounding factors including at least one of tumor grade, patient age, comedo necrosis, patient treatment with radiotherapy, and receptor status;

the stratification provided by the total CAS value is superior to the stratification provided by the Van Nuys Prognostic Index; and an above-threshold total CAS value indicates patients that have had surgery for the carcinoma in situ who would benefit from adjuvant radiotherapy, wherein the threshold is an optimal cutoff value determined based on log-rank tests that minimizes the log-rank p-value for stratifying patients into high-risk and low-risk groups.

20. The computer program product of claim 16, wherein the above-threshold total CAS value indicates patients that have had breast conservation surgery for the carcinoma in situ who would benefit from adjuvant radiotherapy, wherein the threshold is an optimal cutoff value determined based on log-rank tests that minimizes the log-rank p-value for stratifying patients into high-risk and low-risk groups.

* * * * *